US012773043B1

(12) United States Patent
DeNoto

(10) Patent No.: US 12,773,043 B1
(45) Date of Patent: Oct. 27, 2026

(54) TOOTHBRUSH CARE APPARATUS

(71) Applicant: Chris Matthew DeNoto, Boca Raton, FL (US)

(72) Inventor: Chris Matthew DeNoto, Boca Raton, FL (US)

(*) Notice: Subject to any disclaimer, the term of this patent is extended or adjusted under 35 U.S.C. 154(b) by 821 days.

(21) Appl. No.: 17/903,968

(22) Filed: Sep. 6, 2022

Related U.S. Application Data

(60) Provisional application No. 63/333,114, filed on Apr. 20, 2022, provisional application No. 63/285,053, filed on Dec. 1, 2021, provisional application No. 63/241,445, filed on Sep. 7, 2021.

(51) Int. Cl.

| | |
|---|---|
| ***A46B 17/06*** | (2006.01) |
| ***A46B 9/04*** | (2006.01) |
| ***A61L 2/10*** | (2026.01) |
| ***A61L 2/186*** | (2026.01) |

(52) U.S. Cl.
CPC ................ *A46B 17/06* (2013.01); *A61L 2/10* (2013.01); *A61L 2/186* (2013.01); *A46B 9/04* (2013.01); *A46B 2200/1066* (2013.01)

(58) Field of Classification Search
CPC . A61L 2/10; A61L 2/186; A46B 17/06; A46B 9/04; A46B 9/045; A46B 17/065; A26B 17/04
See application file for complete search history.

(56) References Cited

U.S. PATENT DOCUMENTS

| | | |
|---|---|---|
| 2,562,482 A | 7/1951 | Weisser |
| 2,767,830 A | 10/1956 | Levy |
| 2,947,412 A | 8/1960 | Tupper |
| 3,846,862 A | 11/1974 | Botting |
| 5,032,188 A | 7/1991 | Kettle et al. |
| 5,042,107 A | 8/1991 | Gregory et al. |
| 5,048,144 A | 9/1991 | Andrews |
| 5,363,959 A | 11/1994 | Crosby et al. |

(Continued)

FOREIGN PATENT DOCUMENTS

| | | |
|---|---|---|
| CN | 2166675 Y | 6/1994 |
| CN | 2285585 Y | 7/1998 |

(Continued)

*Primary Examiner* — Donald R Spamer
*Assistant Examiner* — Kayla Rose Sarantakos
(74) *Attorney, Agent, or Firm* — Allen D Hertz, P.A.; Allen D. Hertz

(57) ABSTRACT

A toothbrush care system comprising at least one of a toothbrush bristle restoration apparatus and a toothbrush bristle sanitizing apparatus. The bristle restoration apparatus includes at least one bristle restoration and maintenance element and an opposing element where surfaces thereof are arranged to provide a restoration and maintenance force to bristles of a toothbrush. The bristle sanitizing apparatus can include a sanitizing light emitting element which emits sanitizing light to a light pipe, wherein the light pipe is arranged to be inserted between rows of bristles of the toothbrush. Alternatively, a gas emitting chemical can be applied to a sanitizing pad that would be located within an interior of the apparatus. The toothbrush bristle restoration apparatus and a toothbrush bristle sanitizing apparatus can be utilized independently or in combination.

20 Claims, 43 Drawing Sheets

(56) References Cited

U.S. PATENT DOCUMENTS

| | | | | | |
|---|---|---|---|---|---|
| 5,509,168 | A | * | 4/1996 | Butler | A46B 17/04 24/562 |
| 5,645,167 | A | | 7/1997 | Conrad | |
| 5,924,567 | A | | 7/1999 | Wenum | |
| 6,171,559 | B1 | | 1/2001 | Sanders et al. | |
| 6,338,406 | B1 | | 1/2002 | Zagar | |
| 6,753,537 | B2 | | 6/2004 | Woo | |
| 6,757,931 | B2 | | 7/2004 | Nordstrom | |
| 6,972,416 | B2 | | 12/2005 | Huang et al. | |
| 7,213,603 | B2 | | 5/2007 | Pinksy | |
| 7,246,400 | B2 | | 7/2007 | Ryan | |
| 7,987,980 | B1 | | 8/2011 | Hahn | |
| 8,074,796 | B1 | | 12/2011 | Andrews | |
| 8,091,701 | B1 | | 1/2012 | Depietro | |
| 8,607,979 | B1 | | 12/2013 | Cody | |
| 8,668,085 | B1 | | 3/2014 | Oliver | |
| 8,809,807 | B2 | | 8/2014 | Nelson et al. | |
| 9,000,398 | B2 | | 4/2015 | Nelson et al. | |
| 9,944,113 | B2 | | 4/2018 | Depaola, Jr. et al. | |
| 2004/0155201 | A1 | | 8/2004 | Russell et al. | |
| 2007/0200072 | A1 | | 8/2007 | Shin | |
| 2007/0295916 | A1 | | 12/2007 | Reuben | |
| 2008/0060829 | A1 | | 3/2008 | Jansheski | |
| 2008/0286713 | A1 | | 11/2008 | Nanda | |
| 2015/0230597 | A1 | | 8/2015 | Gabbard | |
| 2015/0250298 | A1 | | 9/2015 | Griffiths | |
| 2017/0099942 | A1 | | 4/2017 | Millard | |
| 2017/0273450 | A1 | | 9/2017 | Pulie | |

FOREIGN PATENT DOCUMENTS

| | | | | | |
|---|---|---|---|---|---|
| CN | 1153635 | C | | 6/2004 | |
| CN | 100379371 | C | | 4/2008 | |
| CN | 201070103 | Y | | 6/2008 | |
| CN | 101036794 | B | | 11/2010 | |
| CN | 101926617 | A | | 12/2010 | |
| CN | 204306285 | U | | 5/2015 | |
| CN | 209332773 | U | | 9/2019 | |
| CN | 213587672 | U | * | 7/2021 | |
| DE | 29820966 | U1 | | 4/1999 | |
| DE | 100268869 | | | 6/2001 | |
| DE | 202009015973 | U1 | * | 5/2010 | A46B 17/065 |
| EP | 3031354 | A1 | | 11/2020 | |
| FR | 2818514 | A | | 3/2003 | |
| GB | 2132475 | A | | 7/1984 | |
| JP | S52159765 | U | | 12/1977 | |
| JP | S5938833 | U | | 3/1984 | |
| JP | S6010533 | U | | 1/1985 | |
| JP | H09191938 | A | | 7/1997 | |
| JP | 3047870 | U | | 4/1998 | |
| JP | 3052412 | U | | 9/1998 | |
| JP | 10286123 | A | * | 10/1998 | |
| JP | H10286123 | A | | 10/1998 | |
| JP | 11042117 | | | 2/1999 | |
| JP | H11127958 | A | | 5/1999 | |
| JP | H11178640 | A | | 7/1999 | |
| JP | H11299543 | A | | 11/1999 | |
| JP | 3425334 | | | 5/2003 | |
| JP | 3543110 | B2 | | 7/2004 | |
| JP | 2005334596 | A | | 12/2005 | |
| JP | 2008307344 | | | 12/2008 | |
| JP | 2012035036 | A | | 2/2012 | |
| JP | 3174731 | | | 3/2012 | |
| JP | 2012075755 | A | | 4/2012 | |
| JP | 4977393 | B2 | | 7/2012 | |
| JP | 2013081736 | A | | 5/2013 | |
| JP | 2017046766 | A | | 3/2017 | |
| JP | 2022080718 | | | 5/2022 | |
| KR | 19930011930 | | | 7/1993 | |
| KR | 2000-0001771 | | | 1/2000 | |
| KR | 200427398 | Y1 | | 9/2006 | |
| KR | 100784160 | B1 | | 12/2007 | |
| KR | 20110088874 | A | | 8/2011 | |
| KR | 101139394 | | | 4/2012 | |
| KR | 101216552 | | | 12/2012 | |
| KR | 20130021158 | | | 3/2013 | |
| KR | 20180006567 | A | | 1/2018 | |
| WO | WO1996016750 | A1 | | 6/1996 | |
| WO | WO2006017906 | | | 2/2006 | |
| WO | WO2016/042651 | | | 3/2016 | |
| WO | WO2017/213574 | | | 12/2017 | |

* cited by examiner

TOOTHBRUSH CARE APPARATUS

CROSS-REFERENCE TO RELATED APPLICATIONS

This Non-Provisional Patent Applications Claims Benefit to Each of:

A) U.S. Provisional Patent Application Ser. No. 63/241,445, filed on Sep. 7, 2021;

B) U.S. Provisional Patent Application Ser. No. 63/285,053, filed on Dec. 1, 2021; and C) U.S. Provisional Patent Application Ser. No. 63/333,114, filed on Apr. 20, 2022;

each of which are incorporated herein in their entireties.

FIELD OF THE INVENTION

The present invention relates to an apparatus for care and conditioning of a toothbrush, more specifically bristle restoration, conditioning, and sanitizing.

BACKGROUND OF THE INVENTION

Oral care is primary routine for maintaining health of an individual. Oral care normally includes brushing the individual's teeth and flossing on a regular basis. This care is commonly accomplished at least twice a day. The frequent brushing deforms bristles of the toothbrush. Additionally, the bristles and body of the toothbrush are constantly exposed to bacteria and other harmful pathogens, simply as a result of the function of brushing one's teeth. As one brushes their teeth, the bristles remove the bacteria and other harmful pathogens from the individual's teeth, gums, and tongue. The bristles additionally remove plaque, which can contain and/or entrap the bacteria and other harmful pathogens. The removed contaminants can be at least partially collected in the bristles of the toothbrush. Once collected within the bristles of the toothbrush, the bacteria and other pathogens can cultivate and be returned to one's mouth during future use, contaminate any surface contacted by the bristles, and the like.

Toothbrushes comprise a head located at a distal end of a handle. A shank or neck is commonly formed between the handle and the head of the toothbrush. Groups of bristles or filaments extend outward from the head of the toothbrush. During use of the toothbrush, the bristles tend to become deformed, generally in a directed away from the grouping of bristles. This deformation can be detrimental to the effectiveness of the toothbrush, can potential injure the gums or the tongue of the user, and the like. The deformed bristles can additionally become lodged between adjacent teeth causing other issues.

The bristles can be arranged in any of a variety of geometry arrangements. One prominent design is a series of parallel rows of bristle groups supported by a rectangular head of the toothbrush. A second common toothbrush includes an oval shaped arrangement of bristle groups supported by an oval shaped head of the toothbrush. Another toothbrush includes a round shaped arrangement of bristle groups supported by a round shaped head of the toothbrush. Another common toothbrush includes a diamond shaped arrangement of bristle groups supported by a diamond shaped head of the toothbrush. The bristles can be of a contact height, a differing height, like thickness, different thickness, like stiffness, differing stiffness's, etc.

Each of these distinct designs can further impact providing a solution to provide a device that can provide bristle restoration, conditioning, and sanitizing.

What is desired is a new apparatus and method of use that sanitizes a head of a toothbrush and/or maintains or restores a shape of the bristles or filaments.

BRIEF SUMMARY OF THE INVENTION

The present invention overcomes the deficiencies of the known art and the problems that remain unsolved by providing an apparatus and a respective method which enables sanitizing of a head of a toothbrush and/or maintaining or restoring a shape of the bristles or filaments.

The present invention provides an apparatus for sanitizing the bristles/filaments and head of a toothbrush. The apparatus can include:

a housing having a size and shape that encapsulates bristles of the toothbrush, the housing including a retention feature that is designed to engage with at least one of a head and a body of a toothbrush, wherein the retention feature retains the housing in position over the bristles of the toothbrush, a sanitizing light emitting element powered by a portable power supply; and at least one light transferring member extending in a direction enabling insertion of the at least one light transferring member between sets of bristles.

In a second aspect, the housing can be designed to be secured surrounding the head of the toothbrush. This can be accomplished using any suitable attachment configuration.

In another aspect, the retention feature includes at least one of: a sliding attachment, a clamping attachment, a snap styled attachment, or any other styled attachment that is suitable with the features of the apparatus.

In yet another aspect, the retention feature includes an attachment design that is suitable with the features of the apparatus.

In yet another aspect, the retention feature includes a sliding attachment.

In yet another aspect, the retention feature includes a clamping attachment.

In yet another aspect, the retention feature includes a snap styled attachment.

In yet another aspect, the housing is one of opaque, transparent, translucent.

In yet another aspect, the housing is at least one of opaque, transparent, translucent.

In yet another aspect, the housing is opaque.

In yet another aspect, the housing is transparent.

In yet another aspect, the housing is translucent.

In yet another aspect, the one of the transparent and translucent portion of the cover enables passage of light therethrough.

In yet another aspect, a light emitting element can be integrated into the design. The emitted light is preferably visible to the human eye.

In yet another aspect, a light emitting element can be integrated into the design. The emitted light is preferably distinct from a second, Ultraviolet (UV) light and visible to the human eye.

In yet another aspect, the sanitizing light emitting element is an Ultraviolet (UV) light emitting element.

In yet another aspect, the sanitizing light emitting element is an Ultraviolet (UV) Light Emitting Diode (LED).

In yet another aspect, the sanitizing light emitting element is located in an interior of at least one of: a top panel of the housing, in one or both side panels of the housing, in a rear panel, in a front panel.

In yet another aspect, sanitizing light emitted from the sanitizing light emitting element is emitted in at least one of: a direction directly towards the bristles or be redirected towards the bristles using a light pipe.

In yet another aspect, sanitizing light emitted from the sanitizing light emitting element is emitted in a direction directly towards the bristles.

In yet another aspect, sanitizing light emitted from the sanitizing light emitting element is emitted in a direction towards the bristles using a light pipe.

In yet another aspect, sanitizing light emitted from the sanitizing light emitting element is emitted in one of: a direction directly towards the bristles or be redirected towards the bristles using a light pipe.

In yet another aspect, sanitizing light emitted from the sanitizing light emitting element is emitted towards the bristles using a light pipe.

In yet another aspect, sanitizing light emitted from the sanitizing light emitting element is emitted towards the bristles using a light pipe, wherein the light pipe is fabricated having a wedge shape.

In yet another aspect, sanitizing light emitted from the sanitizing light emitting element is emitted towards the bristles using a light pipe, wherein the light pipe is fabricated having a rectangular block shape.

In yet another aspect, sanitizing light emitted from the sanitizing light emitting element is emitted towards the bristles using a light pipe, wherein the light pipe is fabricated having a cylindrical shape.

In yet another aspect, sanitizing light emitted from the sanitizing light emitting element is emitted towards the bristles using a light pipe, wherein the light pipe is fabricated having a pyramid shape.

In yet another aspect, sanitizing light emitted from the sanitizing light emitting element is emitted towards the bristles using a light pipe, wherein the light pipe is fabricated having a pyramid shape, the light pipe extending in a direction from the sanitizing light emitting element with the largest size being closest to the sanitizing light emitting element.

In yet another aspect, sanitizing light emitted from the sanitizing light emitting element is emitted towards the bristles using a light pipe, wherein the light pipe is fabricated having a pyramid frustum shape.

In yet another aspect, sanitizing light emitted from the sanitizing light emitting element is emitted towards the bristles using a light pipe, wherein the light pipe is fabricated having a pyramid frustum shape, the light pipe extending in a direction from the sanitizing light emitting element with the largest size being closest to the sanitizing light emitting element.

In yet another aspect, sanitizing light emitted from the sanitizing light emitting element is emitted towards the bristles using a light pipe, wherein the light pipe is fabricated having a conical shape.

In yet another aspect, sanitizing light emitted from the sanitizing light emitting element is emitted towards the bristles using a light pipe, wherein the light pipe is fabricated having a conical shape, the light pipe extending in a direction from the sanitizing light emitting element with the largest size being closest to the sanitizing light emitting element.

In yet another aspect, sanitizing light emitted from the sanitizing light emitting element is emitted towards the bristles using a light pipe, wherein the light pipe is fabricated having a conical frustum shape.

In yet another aspect, sanitizing light emitted from the sanitizing light emitting element is emitted towards the bristles using a light pipe, wherein the light pipe is fabricated having a conical frustum shape, the light pipe extending in a direction from the sanitizing light emitting element with the largest size being closest to the sanitizing light emitting element.

In yet another aspect, sanitizing light emitted from the sanitizing light emitting element is emitted towards the bristles using a light pipe, wherein the light pipe is fabricated having a conical frustum shape, the light pipe extending in a direction from the sanitizing light emitting element with the largest size being closest to the sanitizing light emitting element.

In yet another aspect, the light pipe is fabricated having a like cross sectional shape extending in a linear arrangement to accommodate sets of bristles arranged in a linear arrangement.

In yet another aspect, the light pipe is fabricated having a like cross sectional shape extending in an arched arrangement to accommodate sets of bristles arranged in an arched arrangement.

In yet another aspect, the light pipe is fabricated having a like cross sectional shape extending in a diamond shaped arrangement to accommodate sets of bristles arranged in a diamond shaped.

In yet another aspect, the light pipe is arranged to be inserted into the sets of bristles in a direction that is substantially parallel to an elongated direction/axis of the bristles.

In yet another aspect, the light pipe is arranged to be inserted into the sets of bristles in a direction that is substantially parallel to an alignment of sets of bristles.

In yet another aspect, the light pipe is arranged to be inserted into the sets of bristles in a direction that is substantially tangential to an alignment of sets of bristles.

In yet another aspect, the light pipe is preferably molded as a single component.

In yet another aspect, the light pipe is preferably molded as a single component and integral with the housing.

In yet another aspect, the sanitizing light emitting element is located in an interior of at least one of: a top panel of the housing, in one or both side panels of the housing, in a rear panel, in a front panel.

In yet another aspect, the sanitizing light emitting element is located in a top panel of the housing and oriented to emit sanitizing light in an interior direction.

In yet another aspect, the sanitizing light emitting element is located in one or both side panels of the housing and oriented to emit sanitizing light in an interior direction.

In yet another aspect, the sanitizing light emitting element is located in a front panel of the housing and oriented to emit sanitizing light in an interior direction.

In yet another aspect, the sanitizing light emitting element is located in a rear panel of the housing and oriented to emit sanitizing light in an interior direction.

In yet another aspect, power is provided to the sanitizing light emitting element via a portable power supply carried within the housing.

In yet another aspect, power is provided to the sanitizing light emitting element via a portable power supply carried within the handle of the toothbrush.

In yet another aspect, the housing can be positioned in a direction parallel to the bristles (vertically) and snap in position (such as in U.S. Pat. No. 5,048,144), wherein the light pipe can be inserted between sets of bristles during the assembly of the housing onto the toothbrush. This configuration enables use with bristles in any arrangement.

In yet another aspect, in an arrangement of a toothbrush having longitudinally aligned bristles, the housing can slide longitudinally into the head of the toothbrush using a housing design described in U.S. Pat. No. 5,048,144, wherein the light pipe can be inserted between sets of bristles during the assembly of the housing onto the toothbrush.

In yet another aspect, the sanitizing and maintenance circuit can include a heater.

In yet another aspect, the sanitizing and maintenance circuit can include a heater, wherein the heater is operated by a heater circuit operating switch.

In yet another aspect, the sanitizing and maintenance circuit can include a vibrator.

In yet another aspect, the sanitizing and maintenance circuit can include a vibrator, wherein the vibrator can be a linear vibrating motor, an off-balanced rotating motor (such as described as prior art in U.S. Pat. No. 5,107,540A), a pancake motor (such as described in U.S. Pat. No. 5,107,540A), a piezoelectric transducer, and the like In yet another aspect, the sanitizing and maintenance circuit can include a vibrator, wherein the vibrator is operated by a vibrator circuit operating switch.

In yet another aspect, the sanitizing and maintenance circuit can include an air circulating device, such as a fan.

In yet another aspect, the sanitizing and maintenance circuit can include an air circulating device, wherein the air circulating device is operated by an air circulating device circuit operating switch.

In yet another aspect, the housing can be formed in a shape of a tooth.

In yet another aspect, the housing can be formed in a shape of a tooth, wherein a body of the tooth shape is designed to receive the toothbrush and the roots of the tooth shape are designed as grips for opening and closing the body.

In yet another aspect, the housing can be integrated into the toothbrush.

In yet another aspect, the housing can be integrated into the toothbrush, wherein the housing is provided at an end opposite a bristle end thereof.

In yet another aspect, the housing can be integrated into the toothbrush, wherein the housing is provided at an end opposite a bristle end thereof; the toothbrush having a hinge mechanism arranged to pivotally insert the bristles of the toothbrush into a cavity defining the housing.

In yet another aspect, the bristle restoration and maintenance elements are located within the cavity formed at the end of the foldable toothbrush.

In yet another aspect, the bristle restoration and maintenance elements can be selected from a group of differently shaped restoration and maintenance elements, then assembled to an interior surface of the cavity formed at the end of the foldable toothbrush.

In yet another aspect, the bristle restoration and maintenance elements can be selected from a group of differently shaped restoration and maintenance elements, then assembled to an interior surface of the cavity formed at the end of the foldable toothbrush using an adhesive.

In yet another aspect, the sanitizing element is located within the cavity formed at the end of the foldable toothbrush.

In yet another aspect, the sanitizing element as well as the bristle restoration and maintenance elements are located within the cavity formed at the end of the foldable toothbrush.

In yet another aspect, the housing can be designed to accommodate multiple toothbrushes.

In yet another aspect, the housing can be designed to accommodate multiple toothbrushes, at least two of the brushes having toothbrush heads of different shapes.

In yet another aspect, the housing can be designed to accommodate multiple toothbrushes, at least two of the brushes having toothbrush heads of different sizes.

In yet another aspect, the housing can be designed to accommodate multiple toothbrushes, at least two of the brushes having toothbrush heads of different shapes and sizes.

In yet another aspect, the housing can be designed to accommodate multiple toothbrushes, at least two of the brushes having toothbrush heads of at least one of different shapes and different sizes.

In yet another aspect, the housing can be designed to accommodate multiple toothbrushes, at least two of the brushes having toothbrush heads of at least one of different shapes and different sizes by including a series of different shaped cavities, each cavity designed for a head of a toothbrush having a specific shape.

In yet another aspect, the housing can be designed to accommodate multiple toothbrushes, at least two of the brushes having toothbrush heads of at least one of different shapes and different sizes by including a series of different shaped cavities, each cavity designed for a head of a toothbrush having a specific shape, at least one cavity further comprising a surface that engages with the bristles of the toothbrush to restore and/or maintain an original shape of the bristles.

In yet another aspect, the housing can be designed to accommodate multiple toothbrushes, at least two of the brushes having toothbrush heads of at least one of different shapes and different sizes by including a series of different shaped cavities, the housing having a clamshell style design for opening and closing.

In yet another aspect, the housing can be designed to accommodate multiple toothbrushes, at least two of the brushes having toothbrush heads of at least one of different shapes and different sizes by including a series of different shaped cavities, the housing having a clamshell style design for opening and closing, each cavity designed for a head of a toothbrush having a specific shape, at least one cavity further comprising a surface that engages with the bristles of the toothbrush to restore and/or maintain an original shape of the bristles.

In another variation for sanitizing the bristles/filaments and head of a toothbrush. The apparatus can include:

- a housing having a size and shape that encapsulates bristles of the toothbrush, the housing including a retention feature that is designed to engage with at least one of a head and a body of a toothbrush, wherein the retention feature retains the housing in position over the bristles of the toothbrush;
- a sanitizing strip comprising a carrier, an adhesive and a sanitizing solution embedded in the carrier, wherein the sanitizing strip is removably adhesively bonded to an interior surface of the housing.

In a second aspect, the apparatus includes multiple sanitizing strips.

In another aspect, the apparatus includes multiple sanitizing strips, wherein a first sanitizing strip is adhered to a first side of the housing and a second sanitizing strip is adhered to a second side of the housing.

In yet another aspect, the apparatus includes multiple sanitizing strips, wherein a first sanitizing strip is adhered to a first side of the housing at a location adjacent to the bristles of the toothbrush and a second sanitizing strip is adhered to a second side of the housing at a location adjacent to the bristles of the toothbrush.

In yet another aspect, the apparatus includes multiple sanitizing strips, wherein a first sanitizing strip is adhered to a first side of the housing within a first cavity and a second sanitizing strip is adhered to a second side of the housing within a second cavity.

In yet another aspect, the apparatus includes multiple sanitizing strips, wherein a first sanitizing strip is adhered within a first cavity located on a first side of the housing and a second sanitizing strip is adhered within a second cavity located on a second side of the housing.

In yet another aspect, the apparatus includes multiple sanitizing strips, wherein a first sanitizing strip is adhered to a first side of the housing within a first cavity formed at a location adjacent to the bristles of the toothbrush and a second sanitizing strip is adhered to a second side of the housing within a second cavity formed at a location adjacent to the bristles of the toothbrush.

In yet another aspect, each cavity for the sterilizing strip includes an access for ease of removal of the sterilizing strip.

In accordance with a bristle maintenance or bristle restoration function, a bristle maintenance or bristle restoration apparatus can include:

- at least one restoration member configured to enable insertion of bristles of a toothbrush against a contacting surface of the at least one restoration member and subsequently apply a restoration force to the bristles of the toothbrush,
- a restoration force applying component, wherein the restoration force applying component causes the at least one restoration member to apply a restoration force to the bristles of the toothbrush; and
- a toothbrush retention member, wherein the toothbrush retention member retains the bristle maintenance or bristle restoration apparatus upon the toothbrush.

In a second aspect, the at least one restoration member is a flexible member.

In another aspect, the at least one restoration member is a flexible member; more specifically provided in a form of a strap.

In yet another aspect, the restoration force applying component secures a first end of the restoration member and a second end of the restoration member to one another.

In yet another aspect, the restoration force applying component secures a first end of the restoration member (provided in a form of a strap) and a second end of the restoration member to one another.

In yet another aspect, the restoration force applying component secures a first end of the restoration member and a second end of the restoration member to one another wherein the restoration force applying component is a loop.

In yet another aspect, the restoration force applying component secures a first end of the restoration member and a second end of the restoration member to one another wherein the restoration force applying component is a loop and the strap includes embosses designed to engage with the loop.

In yet another aspect, the restoration force applying component secures a first end of the restoration member and a second end of the restoration member to one another wherein the restoration force applying component is a buckle.

In yet another aspect, the restoration force applying component secures a first end of the restoration member and a second end of the restoration member to one another wherein the restoration force applying component is provide as a pair of loops.

In yet another aspect, the restoration force applying component secures a first end of the restoration member and a second end of the restoration member to one another wherein the restoration force applying component is mating sections of a dense hook and loop tape.

In yet another aspect, the at least one restoration member is a clip.

In yet another aspect, the at least one restoration member is a clip.

In yet another aspect, the toothbrush retention member is a biased pair of cantilevered members.

In yet another aspect, the toothbrush retention member is a strap designed to be pass across an exterior surface (surface opposite the bristles) of a head of the toothbrush.

In accordance with another bristle maintenance or bristle restoration function, a bristle maintenance or bristle restoration function apparatus can include:

- a casing having a size and shape that cover bristles of a toothbrush, the casing including a retention feature that is designed to engage with at least one of a head and a body of a toothbrush, wherein the retention feature retains the casing in position over bristles of the toothbrush,
- at least one bristle restoration and maintenance element carried by the casing, each of the at least one bristle restoration and maintenance element comprising a bristle restoration and maintenance surface; and
- a compression system arranged to cause the bristle restoration and maintenance surface to apply a restoration force to the bristles of the toothbrush.

In a second aspect, the casing of the bristle maintenance or bristle restoration apparatus is formed to include a spring biased shape.

In another aspect, the casing of the bristle maintenance or bristle restoration apparatus is formed to include a spring biased shape, wherein plastic properties of a material of the casing create the spring bias force.

In another aspect, the casing of the bristle maintenance or bristle restoration apparatus is formed to include a spring biased shape, wherein plastic properties of a material of the casing create the spring bias force, wherein the spring bias force naturally draws opposing ends of the pair of members towards one another.

In another aspect, the casing of the bristle maintenance or bristle restoration apparatus is formed to include a spring biased shape, wherein plastic properties of a material of the casing create the spring bias force, wherein the spring bias force naturally draws opposing ends of the pair of members towards one another. The opposing ends of the pair of members are moved away from one another by the compression system.

In another aspect, the casing of the bristle maintenance or bristle restoration apparatus is formed to include a spring biased shape, wherein plastic properties of a material of the casing create the spring bias force, wherein the spring bias force naturally draws opposing ends of the pair of members away from one another.

In another aspect, the casing of the bristle maintenance or bristle restoration apparatus is formed to include a spring biased shape, wherein plastic properties of a material of the casing create the spring bias force, wherein the spring bias force naturally draws opposing ends of the pair of members away from one another. The opposing ends of the pair of members are driven towards one another by the compression system.

In yet another aspect, the casing of the bristle maintenance or bristle restoration apparatus includes a pair of members pivotally assembled to one another.

In yet another aspect, the casing of the bristle maintenance or bristle restoration apparatus includes a pair of members pivotally assembled to one another and a biasing member, wherein the biasing member provides a return force. The return force draws opposing ends of the pair of members towards one another.

In yet another aspect, each member of the pair of members further comprising a grip portion, wherein the grip portion enables a user to apply a compression force to each of the pair of grip portions of the pair of members to draw opposing ends of the pair of members away from one another over the return force of the biasing member.

In yet another aspect, the compression system is designed to position a sidewall of the casing to cause the bristle restoration and maintenance surface to apply a restoration force to the bristles of the toothbrush.

In yet another aspect, the compression system is carried by the casing and arranged to cause the bristle restoration and maintenance surface to apply a restoration force to the bristles of the toothbrush.

In yet another aspect, the compression system is arranged to cause one bristle restoration and maintenance surface of one bristle restoration and maintenance element and an opposing surface of the casing to apply a restoration force to the bristles of the toothbrush.

In yet another aspect, the at least one bristle restoration and maintenance element includes at least two restoration and maintenance elements.

In yet another aspect, the compression system is arranged to cause a bristle restoration and maintenance surface of a first bristle restoration and maintenance element of the at least two restoration and maintenance elements and a bristle restoration and maintenance surface of a second bristle restoration and maintenance element of the at least two restoration and maintenance elements to apply a restoration force to the bristles of the toothbrush.

In yet another aspect, the compression system is arranged to cause a bristle restoration and maintenance surface of a first bristle restoration and maintenance element of the at least two restoration and maintenance elements and an opposing bristle restoration and maintenance surface of a second bristle restoration and maintenance element of the at least two restoration and maintenance elements to apply a restoration force to the bristles of the toothbrush.

In yet another aspect, the at least one bristle restoration and maintenance element includes a pair of restoration and maintenance elements.

In yet another aspect, the compression system is arranged to cause a bristle restoration and maintenance surface of a first bristle restoration and maintenance element of the pair of restoration and maintenance elements and a bristle restoration and maintenance surface of a second bristle restoration and maintenance element of the pair of restoration and maintenance elements to apply a restoration force to the bristles of the toothbrush.

In yet another aspect, the compression system is arranged to cause a bristle restoration and maintenance surface of a first bristle restoration and maintenance element of the pair of restoration and maintenance elements and an opposing bristle restoration and maintenance surface of a second bristle restoration and maintenance element of the pair of restoration and maintenance elements to apply a restoration force to the bristles of the toothbrush.

In yet another aspect, the casing of the bristle maintenance or bristle restoration apparatus includes a first sidewall and a second sidewall, wherein a span between the sidewalls is adjustable.

In yet another aspect, the bristle restoration and maintenance elements are integral with the first sidewall and the second sidewall.

In yet another aspect, the bristle restoration and maintenance elements are removably assembled to the first sidewall and the second sidewall.

In yet another aspect, the bristle restoration and maintenance elements are removably assembled to the first sidewall and the second sidewall using a tab and a slot interface.

In yet another aspect, the bristle restoration and maintenance elements are removably assembled to the first sidewall and the second sidewall using a tab and a keyhole slot interface.

In yet another aspect, the bristle restoration and maintenance elements are removably assembled to the first sidewall and the second sidewall using a dense hook and loop tape.

In yet another aspect, the bristle restoration and maintenance elements are removably assembled to the first sidewall and the second sidewall using a snap interface.

In yet another aspect, the bristle restoration and maintenance elements are removably assembled to the first sidewall and the second sidewall using a double sided adhesive.

In yet another aspect, the bristle restoration and maintenance elements are removably assembled to the first sidewall and the second sidewall using a double sided adhesive tape.

In yet another aspect, the casing of the bristle maintenance or bristle restoration apparatus includes a first sidewall and a second sidewall, wherein a span between the sidewalls is adjustable, wherein the adjustment is provided by a ratchet interface.

In yet another aspect, the casing of the bristle maintenance or bristle restoration apparatus includes a first sidewall and a second sidewall, wherein a span between the sidewalls is adjustable, wherein the adjustment is provided by a threaded interface.

In yet another aspect, the bristle restoration and maintenance elements are integral with the first sidewall and the second sidewall.

In yet another aspect, the casing of the bristle maintenance or bristle restoration apparatus includes a first sidewall and a second sidewall, wherein a span between the sidewalls is adjustable, wherein the adjustment is provided by a threaded interface employing a threaded member.

In yet another aspect, the casing of the bristle maintenance or bristle restoration apparatus includes a first sidewall and a second sidewall, wherein a span between the sidewalls is fixed, where in a span between a first bristle maintenance or bristle restoration pad and a second bristle maintenance or bristle restoration pad is adjustable.

In yet another aspect, one bristle maintenance or bristle restoration pad is fixed to a first sidewall and a second bristle maintenance or bristle restoration pad is moveable respective to a second sidewall.

In yet another aspect, one bristle maintenance or bristle restoration pad is moveable respective to the first sidewall and a second bristle maintenance or bristle restoration pad is moveable respective to the second sidewall.

In yet another aspect, movement between a bristle maintenance or bristle restoration pad and the respective sidewall is accomplished using a threaded member.

In yet another aspect, movement between a bristle maintenance or bristle restoration pad and the respective sidewall is accomplished using a threaded member, wherein the threaded member is threadably engaged with a threaded bore formed through the respective sidewall.

In yet another aspect, movement between a bristle maintenance or bristle restoration pad and the respective sidewall is accomplished using a threaded member, wherein the threaded member is detachably assembled to the bristle maintenance or bristle restoration pad.

In yet another aspect, movement between a bristle maintenance or bristle restoration pad and the respective sidewall is accomplished using a threaded member, wherein the threaded member is detachably assembled to the bristle maintenance or bristle restoration pad using a bulbous feature on an end of the threaded member and a receiving socket formed in the bristle maintenance or bristle restoration pad.

In yet another aspect, movement between a bristle maintenance or bristle restoration pad and the respective sidewall is accomplished using a sliding control member retaining a pressure to the bristle maintenance or bristle restoration pad by a biasing element.

In yet another aspect, movement between a bristle maintenance or bristle restoration pad and the respective sidewall is accomplished using a sliding control member retaining a pressure to the bristle maintenance or bristle restoration pad by a biasing element, wherein the biasing element is a coil spring.

In yet another aspect, movement between a bristle maintenance or bristle restoration pad and the respective sidewall is accomplished using a sliding control member retaining a pressure to the bristle maintenance or bristle restoration pad by a biasing element, wherein the biasing element is a compression spring.

In yet another aspect, movement between a bristle maintenance or bristle restoration pad and the respective sidewall is accomplished using a sliding control member retaining a pressure to the bristle maintenance or bristle restoration pad by a biasing element, wherein the biasing element is a compression coil spring.

In yet another aspect, movement between a bristle maintenance or bristle restoration pad and the respective sidewall is accomplished using a sliding control member retaining a pressure to the bristle maintenance or bristle restoration pad by a biasing element, wherein the biasing element is a cantilevered spring.

In yet another aspect, the bristle restoration and maintenance surface is planar in shape.

In yet another aspect, the bristle restoration and maintenance surface has a planar shape when viewed along an axial direction of the bristles.

In yet another aspect, the bristle restoration and maintenance surface has a semi-oval shape when viewed along an axial direction of the bristles.

In yet another aspect, the bristle restoration and maintenance surface has a semi-circular shape when viewed along an axial direction of the bristles.

In yet another aspect, the bristle restoration and maintenance surface has a semi-diamond shape when viewed along an axial direction of the bristles.

In yet another aspect, the bristle restoration and maintenance surface has a v-shape when viewed along an axial direction of the bristles.

In yet another aspect, the bristle restoration and maintenance surface has a c-shape when viewed along an axial direction of the bristles.

In yet another aspect, the bristle restoration and maintenance element is assembled to the casing.

In yet another aspect, the bristle restoration and maintenance element is assembled to the casing in a fixed arrangement.

In yet another aspect, the bristle restoration and maintenance element is moveably assembled to the casing.

In yet another aspect, the bristle restoration and maintenance element is pivotally assembled to the casing.

In yet another aspect, the compression system includes a pair of handles, wherein the pair of handles are arranged to separate opposing ends of the sidewalls of the casing.

In yet another aspect, the compression system includes a pair of handles, wherein the pair of handles are arranged to separate opposing ends of the sidewalls of the casing by attaching an end of each handle to a location proximate an distal free edge or the end of the sidewall and a portion of the handle contacts a point on the sidewall located between the distal free edge of the sidewall and a top section of the casing.

In yet another aspect, the compression system includes a pair of handles, wherein each handle comprising a pair of handle arm sections, at least one handle assembly section, and a handle grip section.

In yet another aspect, the compression system includes a pair of handles, wherein each handle comprising a pair of handle arm sections, a pair of handle assembly sections, and a handle grip section.

In yet another aspect, the compression system includes a pair of handles, wherein each handle comprising a pair of handle arm sections, a pair of handle assembly sections (a first handle assembly section extending in an opposite direction of the second handle assembly section), and a handle grip section.

In yet another aspect, the compression system includes a pair of handles, wherein each handle comprising a pair of handle arm sections, at least one handle assembly section, and a handle grip section, the handle grip section being contiguous with each distal end of the handle arm sections.

In yet another aspect, the compression system includes a pair of handles, wherein each handle is formed of a single rod, the single rod begin shaped to include a pair of handle arm sections, at least one handle assembly section, and a handle grip section, the handle grip section being contiguous with each distal end of the handle arm sections.

In yet another aspect, the compression system includes a pair of handles, wherein each handle is formed of a single rod, the single rod begin shaped to include a pair of handle arm sections, a pair of handle assembly sections, and a handle grip section, the handle grip section being contiguous with each distal end of the handle arm sections.

In yet another aspect, the compression system includes a pair of handles, wherein each handle is formed of a single rod, the single rod begin shaped to include a pair of handle arm sections, a pair of handle assembly sections (a first handle assembly section extending in an opposite direction of the second handle assembly section), and a handle grip section, the handle grip section being contiguous with each distal end of the handle arm sections.

In yet another aspect, the compression system includes a pair of handles, the pair of handles being pivotally assembled to the distal free edge.

In yet another aspect, the compression system includes a pair of handles, the pair of handles being assembled to the distal free edge of the casing by inserting the handle assembly section of the respective handle into a bore of a handle assembly feature provided at the distal free edge of the casing.

In yet another aspect, the compression system includes a pair of handles, the pair of handles being pivotally assembled to the distal free edge of the casing by inserting the handle assembly section of the respective handle into a bore of a handle assembly feature provided at the distal free edge of the casing.

In yet another aspect, the bristle restoration and maintenance element includes a toothbrush bristle restoration pad body assembly member carried by a toothbrush bristle restoration pad body.

In yet another aspect, the bristle restoration and maintenance element includes at least one toothbrush bristle restoration pad body assembly member carried by a toothbrush bristle restoration pad body.

In yet another aspect, the bristle restoration and maintenance element includes a toothbrush bristle restoration pad body assembly member carried by a toothbrush bristle restoration pad body, a bore passing through each of the at least one toothbrush bristle restoration pad body assembly member.

In yet another aspect, the bristle restoration and maintenance element includes at least one toothbrush bristle restoration pad body assembly member carried by a toothbrush bristle restoration pad body, a bore passing through each of the at least one toothbrush bristle restoration pad body assembly member.

In yet another aspect, the bristle restoration and maintenance element is assembled to the casing by assembling the toothbrush bristle restoration pad body assembly member to the casing.

In yet another aspect, the bristle restoration and maintenance element is assembled to the casing by pivotally assembling the toothbrush bristle restoration pad body assembly member to the casing.

In yet another aspect, the bristle restoration and maintenance element is assembled to the casing by pivotally assembling the toothbrush bristle restoration pad body assembly member to the casing using a toothbrush bristle restoration pad assembly pin.

In yet another aspect, the bristle restoration and maintenance element is assembled to the casing by pivotally assembling the toothbrush bristle restoration pad body assembly member to the casing by inserting the toothbrush bristle restoration pad assembly pin through a toothbrush bristle restoration pad body assembly bore/hole formed through the toothbrush bristle restoration pad body assembly member.

In yet another aspect, the bristle restoration and maintenance element can be fabricated of a rigid material.

In yet another aspect, the bristle restoration and maintenance element can be fabricated of a pliant material.

In yet another aspect, the bristle restoration and maintenance element can be fabricated of at least one of a rigid material and a pliant material.

In another aspect, the casing of the bristle maintenance or bristle restoration apparatus is formed to include a spring biased shape, wherein plastic properties of a material of the casing create the spring bias force, wherein the spring bias force naturally draws opposing ends of the pair of members towards one another and the pair of handles are used to overcome the spring biasing force created by the plastic properties of the material of the casing to draw opposing ends of the pair of members away from one another.

In another aspect, the compression system includes a contraction element, wherein the contraction element toggles the casing between an expanded configuration and a compression configuration.

In another aspect, the compression system includes a contraction element, wherein the contraction element toggles the casing between an expanded configuration and a compression configuration based upon a position of the contraction element.

In another aspect, the compression system includes a contraction element; the contraction element includes a pair of contacting surfaces.

In another aspect, the compression system includes a contraction element; the contraction element includes a pair of opposite facing contacting surfaces.

In another aspect, the compression system includes a contraction element, the contraction element includes a pair of opposite facing contacting surfaces, a distance provided between each contacting surface of the pair of opposite facing contacting surfaces.

In another aspect, the compression system includes a contraction element, the contraction element includes a pair of opposite facing contacting surfaces located at a distal, free end of the contraction element, a distance provided between each contacting surface of the pair of opposite facing contacting surfaces.

In another aspect, the compression system includes a contraction element, the contraction element includes a pair of opposite facing contacting surfaces, a distance provided between each contacting surface of the pair of opposite facing contacting surfaces, wherein the distance between each contacting surface of the pair of opposite facing contacting surfaces is used to toggle the casing between an expanded configuration and a compression configuration.

In another aspect, the compression system includes a contraction element, the contraction element includes a pair of opposite facing contacting surfaces, a distance provided between each contacting surface of the pair of opposite facing contacting surfaces, wherein the distance between each contacting surface of the pair of opposite facing contacting surfaces and an angle of the sidewalls of the casing is used to toggle the casing between an expanded configuration and a compression configuration.

In another aspect, the casing includes a pair of sidewalls, the sidewalls having an acute angle between them, the compression system including a contraction element, the contraction element includes a pair of opposite facing contacting surfaces, a distance provided between each contacting surface of the pair of opposite facing contacting surfaces, wherein the distance between each contacting surface of the pair of opposite facing contacting surfaces and the acute angle between the sidewalls of the casing is used to toggle the casing between an expanded configuration and a compression configuration.

In another aspect, the casing includes a pair of sidewalls, the sidewalls having an acute angle between them, wherein the sidewalls are arranged having a first dimension between opposing surfaces at the distal free end of the casing and a second dimension between opposing surfaces at the attached, top end of the casing (proximate the top panel), wherein the first dimension is greater than the second dimension.

In another aspect, the casing includes a pair of sidewalls, the sidewalls having an acute angle between them, wherein the sidewalls are arranged having a first dimension between opposing surfaces at the distal free end of the casing and a second dimension between opposing surfaces at the attached, top end of the casing (proximate the top panel), wherein the first dimension is greater than the second dimension, wherein the contraction element places the casing in an open configuration when the distal free ends are located proximate the top panel and the contraction element places the casing in a closed, compression configuration when the distal free ends are located proximate the distal free ends.

In another aspect, the casing includes a pair of sidewalls, the sidewalls having an acute angle between them, wherein the sidewalls are arranged having a first dimension between opposing surfaces at the distal free end of the casing and a second dimension between opposing surfaces at the attached, top end of the casing (proximate the top panel), wherein the second dimension is greater than the first dimension.

In another aspect, the casing includes a pair of sidewalls, the sidewalls having an acute angle between them, wherein the sidewalls are arranged having a first dimension between opposing surfaces at the distal free end of the casing and a second dimension between opposing surfaces at the attached, top end of the casing (proximate the top panel), wherein the second dimension is greater than the first dimension, wherein the contraction element places the casing in a closed, compression configuration when the distal free ends are located proximate the distal free ends and the contraction element places the casing in an open configuration when the top panel are located proximate the distal free ends.

In another aspect, the compression system includes a cam, wherein the cam rotates to toggle the casing between an expanded configuration and a compression configuration.

In another aspect, the compression system includes a pair of cams, wherein each cam of the pair of cams rotates to toggle the casing between an expanded configuration and a compression configuration.

In another aspect, the compression system includes a pair of cams, wherein each cam of the pair of cams rotates in unison toggling the casing between an expanded configuration and a compression configuration.

In another aspect, the compression system includes a pair of cams, wherein each cam of the pair of cams is connected to a drive member, wherein the drive member causes the pair of cams to rotate in unison toggling the casing between an expanded configuration and a compression configuration.

In yet another aspect, the casing includes a sanitizing assembly attachment feature for assembling the sanitizing assembly and the restoration member to one another.

In yet another aspect, the casing includes a sanitizing assembly attachment feature for assembling the sanitizing assembly and the restoration member to one another, wherein the sanitizing assembly attachment feature includes an aperture passing through the casing.

In yet another aspect, the casing includes a sanitizing assembly attachment feature for assembling the sanitizing assembly and the restoration assembly to one another, wherein the sanitizing assembly attachment feature includes an aperture passing through the top panel of the casing.

In yet another aspect, the casing includes a sanitizing assembly attachment feature for assembling the sanitizing assembly and the restoration assembly to one another, wherein the sanitizing assembly attachment feature is designed to assemble the sanitizing assembly to an underside of the restoration assembly.

In yet another aspect, the casing includes a sanitizing assembly attachment feature for assembling the sanitizing assembly and the restoration assembly to one another, wherein the sanitizing assembly attachment feature is designed to assemble the sanitizing assembly to an underside of the top panel of the restoration assembly.

In yet another aspect, the casing can act as the contraction element. In another description, the contraction element replaces the casing.

In yet another aspect, the casing can act as the contraction element, where the contraction element engages with the compression elements.

In yet another aspect, the casing can act as the contraction element, where the contraction element engages with the compression elements, wherein movement of the contraction element toggles the compression elements between an insertion configuration and a compression configuration.

In yet another aspect, the housing can be designed receive a toothbrush, the housing comprising a cavity designed for a head of the toothbrush having a specific shape, the cavity comprising opposing surfaces that engage with the bristles of the toothbrush to restore and/or maintain an original shape of the bristles.

In yet another aspect, the housing can be designed receive a toothbrush, the housing comprising a cavity designed for a head of the toothbrush having a specific shape, the cavity comprising opposing surfaces that engage with the bristles of the toothbrush to restore and/or maintain an original shape of the bristles, the housing having a clamshell style opening and closing design.

In yet another aspect, the housing can be designed receive a toothbrush, the housing comprising a cavity designed for a head of the toothbrush having a specific shape, the cavity comprising opposing surfaces are shaped to engage with the bristles of the toothbrush to restore and/or maintain an original shape of the bristles, the housing having a clamshell style opening and closing design.

In yet another aspect, the housing can be designed receive a toothbrush, the housing comprising a cavity designed for a head of the toothbrush having a specific shape, the cavity comprising opposing surfaces that engage with the bristles of the toothbrush to restore and/or maintain an original shape of the bristles, the housing having a clamshell style opening and closing design, wherein a bristle restoration pad is provided upon the opposing surfaces. In yet another aspect, the bristle restoration pad is of a pliant material.

In yet another aspect, the bristle restoration pad is of a pliant material that is adhesively bonded to the interior surface of the housing.

In yet another aspect, the housing can be designed receive a toothbrush, the housing comprising a cavity designed for a head of the toothbrush having a specific shape, the cavity comprising opposing surfaces having a shape that follows a contour of the bristles of the toothbrush to restore and/or maintain an original shape of the bristles, the housing having a clamshell style opening and closing design.

In yet another aspect, the housing can be designed receive a toothbrush, the housing comprising a cavity designed for a head of the toothbrush having a specific shape, the cavity comprising opposing surfaces having a shape that follows a contour of the bristles of the toothbrush to restore and/or maintain an original shape of the bristles, the housing having a clamshell style opening and closing design, wherein the opposing surfaces are provided by a pliant material.

In yet another aspect, the housing can be designed receive a toothbrush, the housing comprising a cavity designed for a head of the toothbrush having a specific shape, the cavity comprising opposing surfaces having a shape that follows a contour of the bristles of the toothbrush to restore and/or maintain an original shape of the bristles, the housing having a clamshell style opening and closing design, wherein the opposing surfaces are provided by an interchangeable component, wherein the interchangeable component is provided for a specifically shaped head of a toothbrush.

In yet another aspect, each toothbrush bristle restoration pad is removably attached to a support member.

In yet another aspect, each removably attached toothbrush bristle restoration pad is selectable from at least two differently shaped toothbrush bristle restoration pads, each toothbrush bristle restoration pad being designed for a specifically shaped toothbrush.

In yet another aspect, the removably attached toothbrush bristle restoration pad is selected from a group of differently shaped toothbrush bristle restoration pads, the group comprising at least two of: a linear edged toothbrush; a linear, parallel edged toothbrush; a rounded rectangularly arranged set of bristles; a rounded toothbrush; a tapered toothbrush; an irregularly shaped bristle arrangement; an oval shaped toothbrush; a diamond shaped toothbrush; or any other known toothbrush arrangement or combination thereof.

In yet another aspect, a set of the removably attached toothbrush bristle restoration pad is included with the toothbrush bristle restoration apparatus.

In yet another aspect, a set of the removably attached toothbrush bristle restoration pads is included with the toothbrush bristle restoration apparatus, enabling the user to select a correct removably attached toothbrush bristle restoration pad into the toothbrush bristle restoration apparatus.

In yet another aspect, each toothbrush bristle restoration pad is pivotally attached to a support member.

In yet another aspect, each toothbrush bristle restoration pad is pivotally attached to a support member, wherein the support member extends inward from a sidewall of a housing.

In yet another aspect, each toothbrush bristle restoration pad is pivotally attached to a support member, wherein the support member extends upward from a bottom wall of the housing.

In yet another aspect, each toothbrush bristle restoration pad is pivotally attached to a support member, wherein the support member extends downward from a top wall of the housing.

In yet another aspect, each pivotally attached toothbrush bristle restoration pad is selectable from at least two differently shaped toothbrush bristle restoration pads, each toothbrush bristle restoration pad being designed for a specifically shaped toothbrush.

In yet another aspect, each pivotally attached toothbrush bristle restoration pad is selectable from at least two differently shaped toothbrush bristle restoration pads, each toothbrush bristle restoration pad being designed for a specifically shaped arrangement of bristles on a toothbrush.

In yet another aspect, each pivotally attached toothbrush bristle restoration pad is replaceable with a different toothbrush bristle restoration pad.

In yet another aspect, each pivotally attached toothbrush bristle restoration pad is replaceable with a different toothbrush bristle restoration pad designed for a specifically shaped toothbrush.

In yet another aspect, each pivotally attached toothbrush bristle restoration pad is replaceable with a different toothbrush bristle restoration pad of a different shape, where the different shape is designed for a specifically shaped toothbrush.

In yet another aspect, each pivotally attached toothbrush bristle restoration pad is replaceable with a different toothbrush bristle restoration pad of a different shape, where the different shape is designed for a specifically shaped arrangement of bristles on a toothbrush.

In yet another aspect, the housing can be designed receive a toothbrush, the housing designed to accommodate a head of the toothbrush, the housing comprising a pair of cavities, each cavity being located adjacent to a respective side of the bristles of the toothbrush, an interchangeable component being inserted into each respective cavity, each interchangeable component having a bristle restoring and maintaining surface of a specific shape to accommodate the respective toothbrush head, wherein the unit is provided with multiple interchangeable components, each interchangeable component is provided for a specifically shaped head of a toothbrush, thus enabling use for any of a variety of head shapes and sizes, the housing having a clamshell style opening and closing design.

In yet another aspect, the interchangeable components can be impregnated with a sanitizing composition that is released in a gaseous form.

In yet another aspect, the sanitizing composition can be at least one of: an alcohol based solution, a chlorine based solution, a sodium hypochlorite based solution, a glutaraldehyde based solution, a hydrogen peroxide based solution, an iodophor based solution, an ortho-phthalaldehyde based solution, a peracetic or peroxyacetic acid based solution, a phenol based solution, a quaternary ammonium compound based solution, and the like or any chemically compatible combination thereof.

In yet another aspect, the assembly can include a heating element.

In yet another aspect, the assembly can include a heating element, wherein the heating element is a resistive heating element.

In yet another aspect, the assembly can include a heating element, wherein the heating element provides heat to at least one toothbrush bristle restoration pad body.

In yet another aspect, the assembly can include a heating element, wherein the heating element provides heat to each toothbrush bristle restoration pad body.

In yet another aspect, the housing can be in any suitable shape. The shape can be any geometric shape, rectangular, diamond shaped, arrow shaped, shaped to resemble an object, shaped to resemble a tooth, shaped to resemble an animal, shaped to resemble a vehicle, or any other shape.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 43 presents an end sectioned view of the eleventh exemplary toothbrush bristle restoration apparatus originally introduced in FIG. 42, the illustration presenting the eleventh exemplary toothbrush bristle restoration apparatus in a closed configuration and details bristle restoration and maintenance elements and a sanitizing member.

Like reference numerals refer to like parts throughout the several views of the drawings.

DETAILED DESCRIPTION OF THE PRESENT INVENTION

Figure 1:
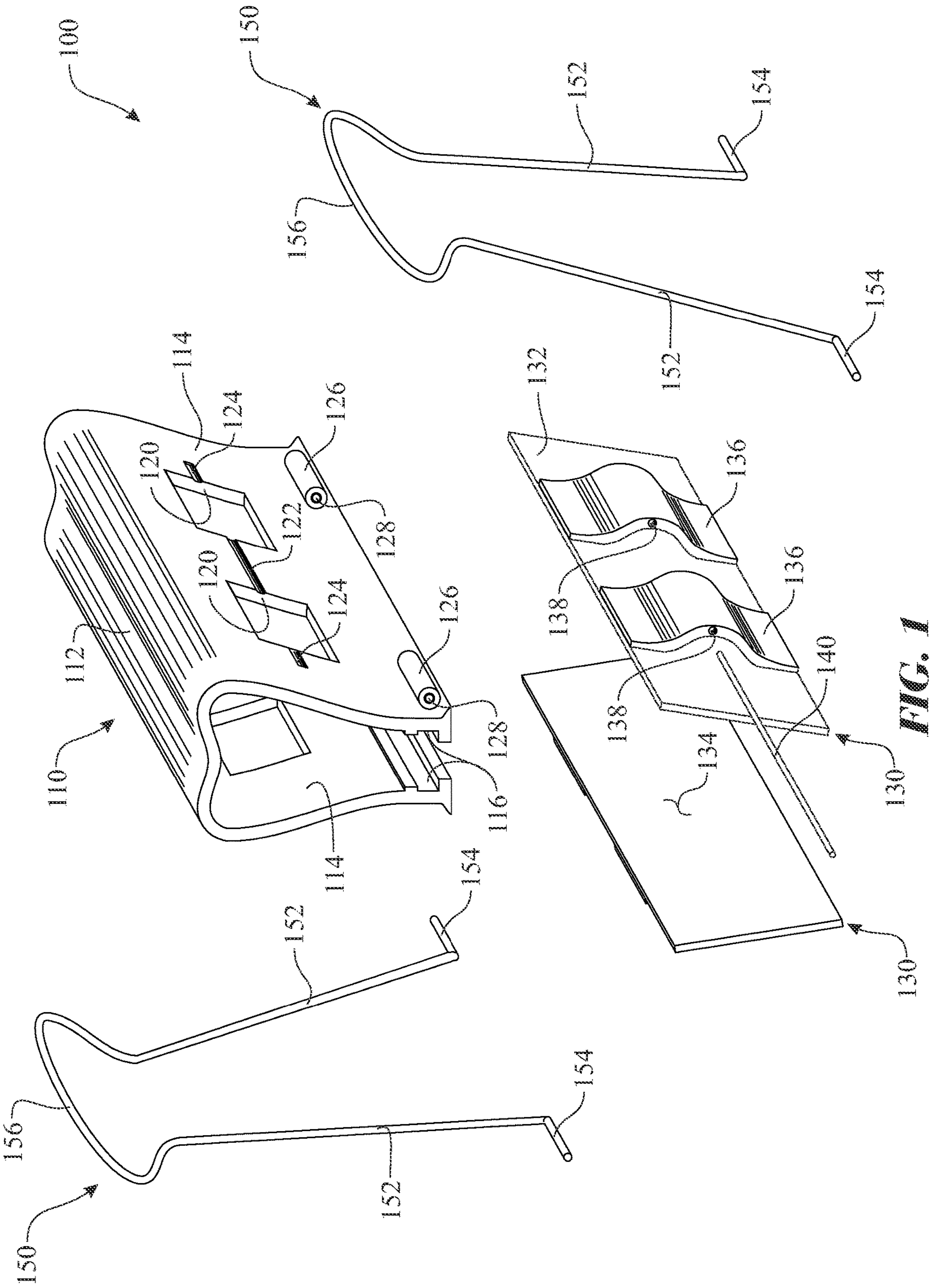
FIG. 1 presents an isometric exploded assembly front, top, side view of a first exemplary toothbrush bristle restoration apparatus.
Figure 2:
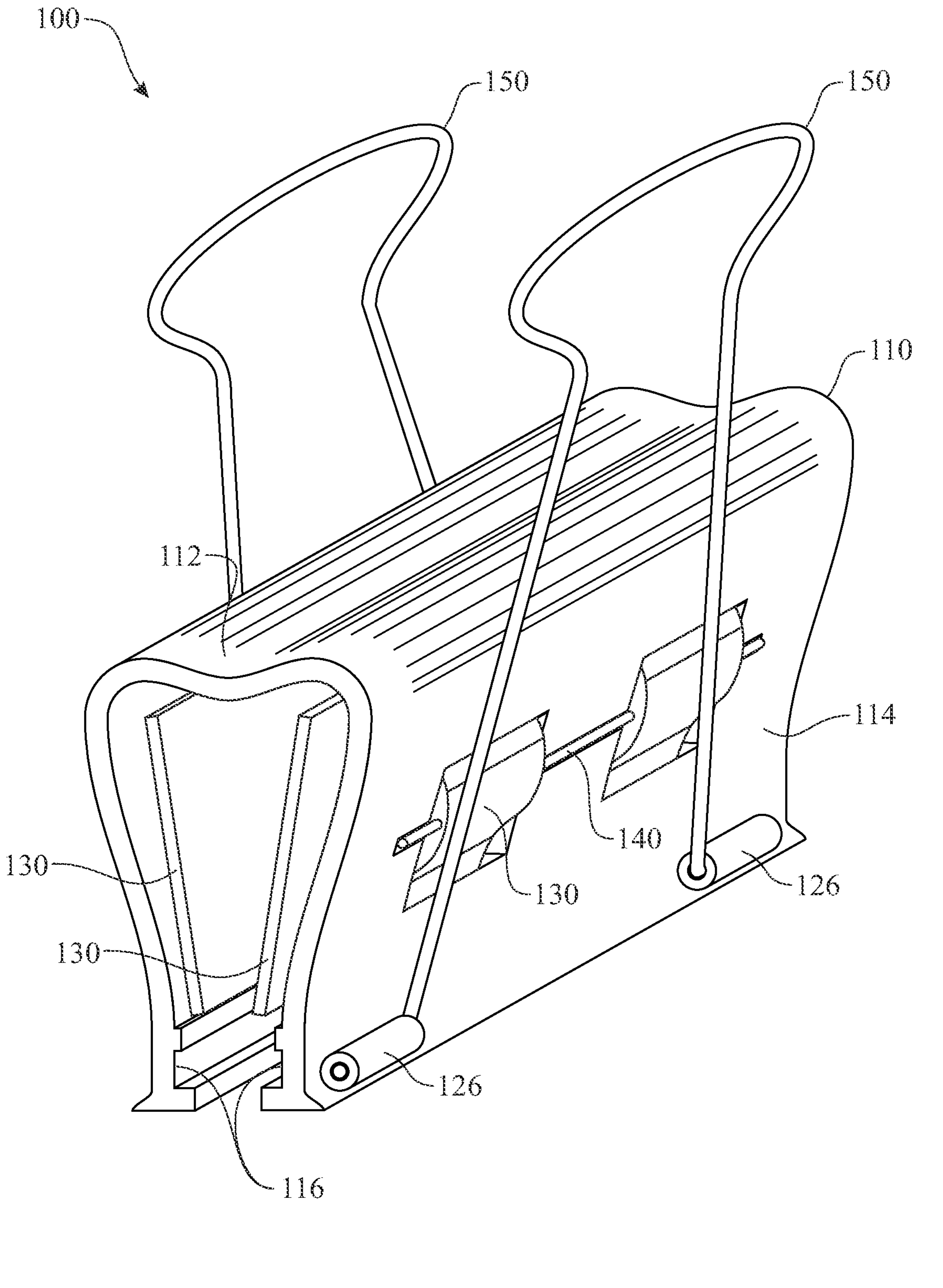
FIG. 2 presents an isometric front, top, side assembled view of the first exemplary toothbrush bristle restoration apparatus originally introduced in FIG. 1.
Figure 3:
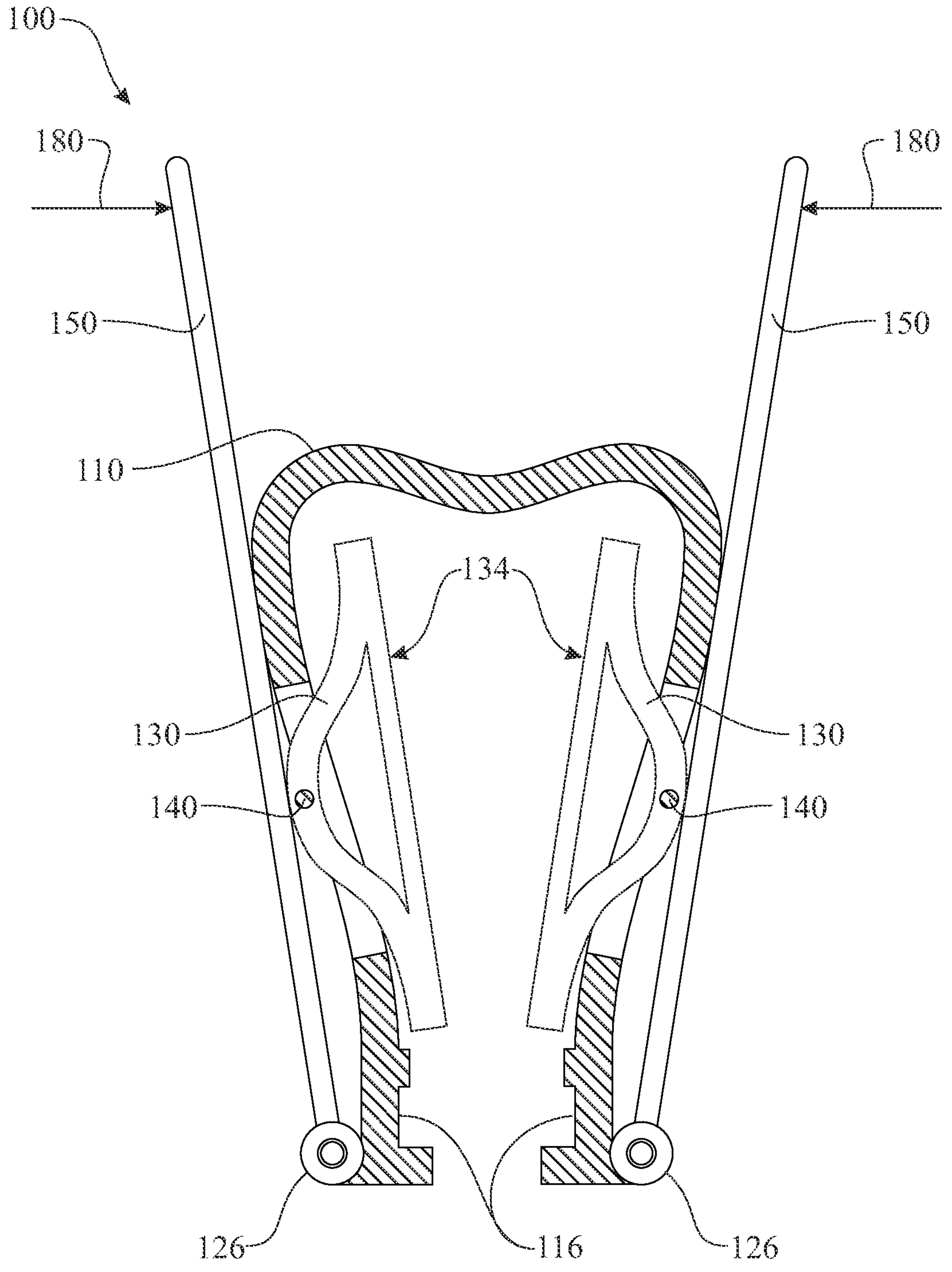
FIG. 3 presents a sectioned end view of the first exemplary toothbrush bristle restoration apparatus originally introduced in FIG. 1, the first exemplary toothbrush bristle restoration apparatus being shown in a relaxed state.

Detailed embodiments of the present invention are disclosed herein. It will be understood that the disclosed embodiments are merely exemplary of the invention that may be embodied in various and alternative forms. The figures are not necessarily to scale, and some features may be exaggerated or minimized to show details of particular embodiments, features, or elements. Specific structural and functional details, dimensions, or shapes disclosed herein are not limiting but serve as a basis for the claims and for teaching a person of ordinary skill in the art the described and claimed features of embodiments of the present invention. The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Oral care is a key to maintaining one's health. A toothbrush, toothpaste, and floss are tools commonly used in maintaining oral hygiene. Toothpaste and floss are consumable items, ensuring sanitary use. Toothbrushes, on the other hand, are reused daily over many months before being replaced. The process of brushing one's teeth transfers plaque, bacteria, and other potentially harmful microbes to bristles of the toothbrush. Additionally, the process of brushing one's teeth deforms the bristles of the toothbrush.

Disclosed herein are two assemblies that can be used independently or in combination for treatment of the toothbrush to improve the lifespan of the toothbrush 400 (FIG. 7) and the quality of oral care. An exemplary toothbrush bristle restoration apparatus 100 is presented in FIGS. 1 through 6. An exemplary toothbrush sanitizing assembly 300 is presented in FIGS. 11 through 15. The toothbrush bristle restoration apparatus 100 and the toothbrush sanitizing assembly 300 can be used independently or in combination. A toothbrush bristle restoration apparatus 200 (a modified version of the toothbrush bristle restoration apparatus 100) and the toothbrush sanitizing assembly 300 can be assembled to one another to collectively treat and maintain the toothbrush assembly 400.

The exemplary toothbrush bristle restoration apparatus 100 includes a toothbrush bristle restoration body 110, a pair of toothbrush bristle restoration pads 130, and a pair of handles 150. The toothbrush bristle restoration body 110 includes a pair of toothbrush bristle restoration body sidewall portion 114 extending in a direction that is generally perpendicular to a toothbrush bristle restoration body top portion 112. The toothbrush bristle restoration body 110 is preferably fabricated of a material having spring properties. Examples of suitable materials include metal, spring copper, spring steel, plastic and the like. The spring properties of the material used to manufacture the toothbrush bristle restoration body 110 enables the toothbrush bristle restoration body 110 to return to an original shape following any application of an outward or an inward force applied to a distal, free end. In the exemplary illustration, the toothbrush bristle restoration body 110 is shaped having an acute angle formed between interior surfaces of each toothbrush bristle restoration body sidewall portion 114 and the toothbrush bristle restoration body top portion 112 respectively. In other variations, the toothbrush bristle restoration body 110 can be shaped having an obtuse angle formed between interior surfaces of each toothbrush bristle restoration body sidewall portion 114 and the toothbrush bristle restoration body top portion 112 respectively. As shown in the exemplary illustration, an arched transition is provided between a proximal edge of each toothbrush bristle restoration body sidewall portion 114 and the respective edge of the toothbrush bristle restoration body top portion 112.

Figure 5:
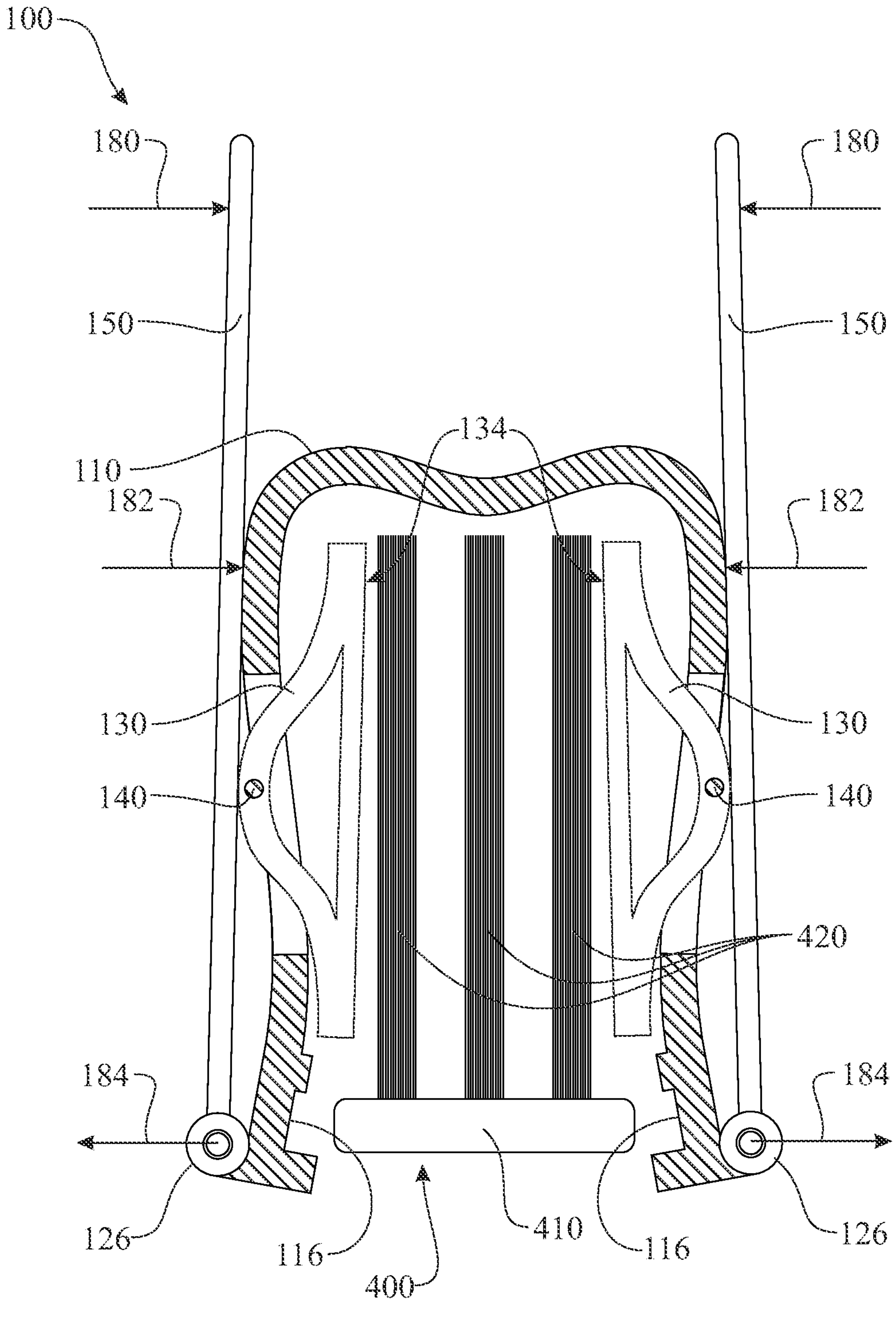
FIG. 5 presents a sectioned end view of the first exemplary toothbrush bristle restoration apparatus originally introduced in FIG. 1, the illustration presenting a toothbrush being inserted into the first exemplary toothbrush bristle restoration apparatus in the expanded state.
Figure 6:
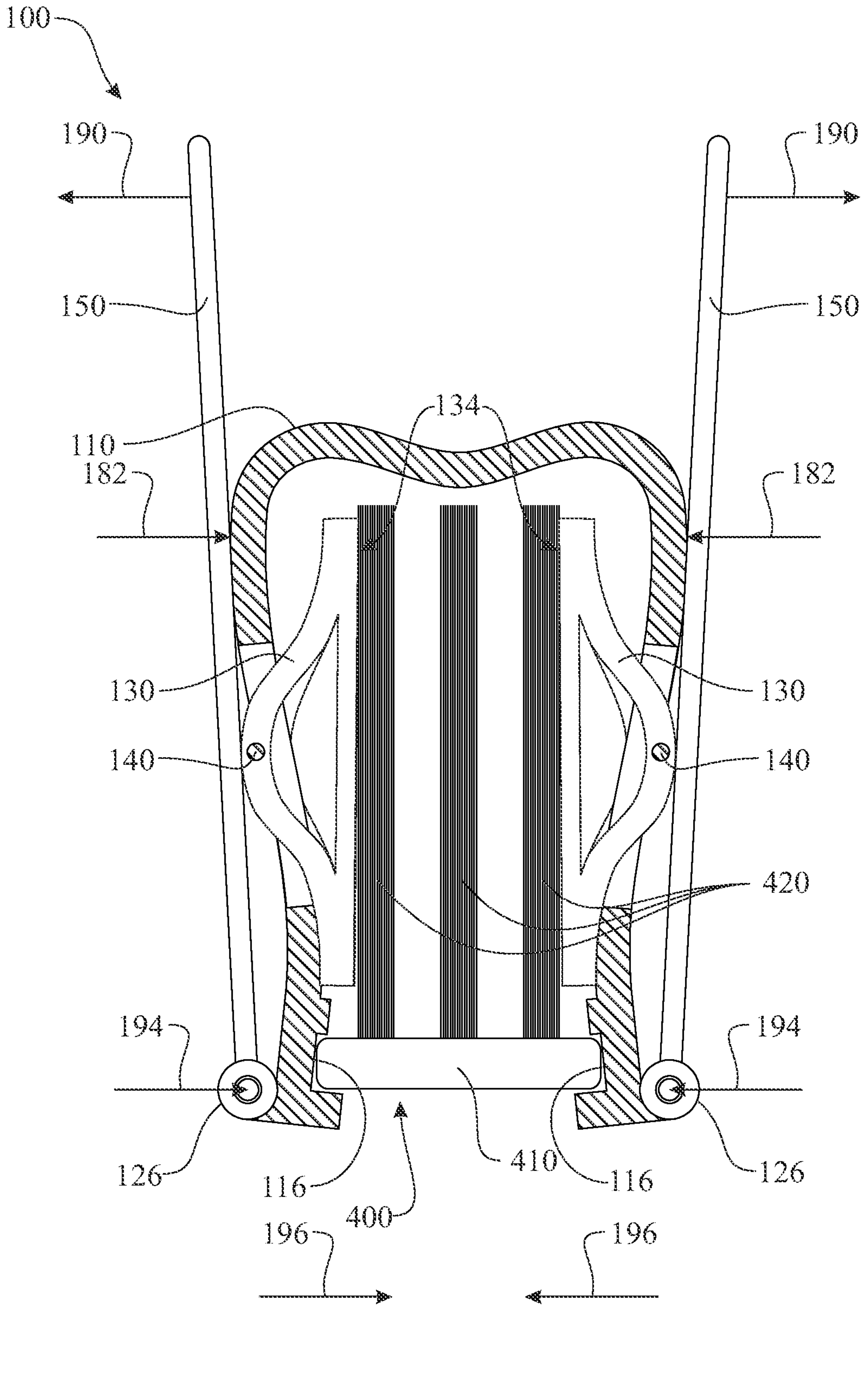
FIG. 6 presents a sectioned end view of the first exemplary toothbrush bristle restoration apparatus originally introduced in FIG. 1, the illustration presenting a toothbrush being gripped by the first exemplary toothbrush bristle restoration apparatus in a bristle restoration and maintenance configuration.
Figure 7:
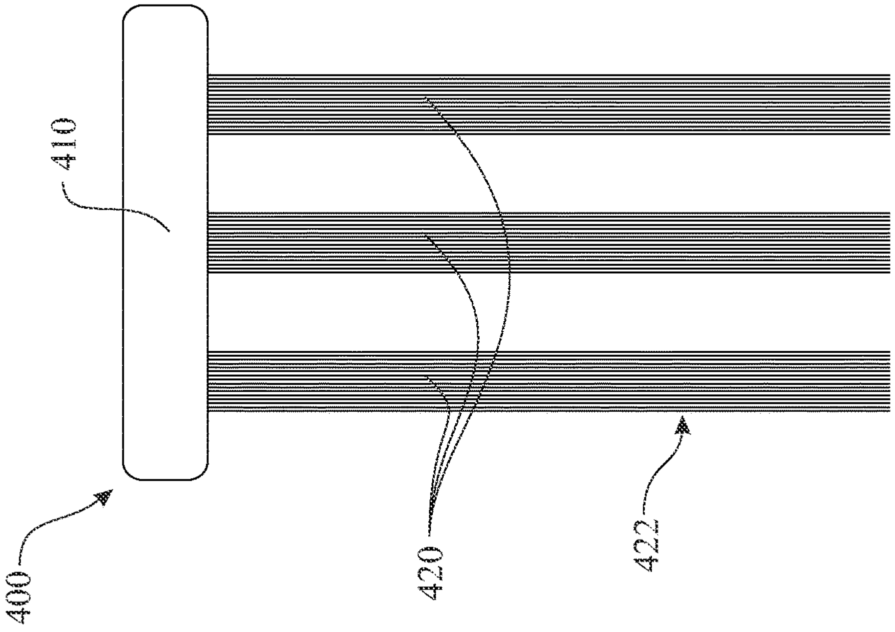
FIG. 7 presents an end view of an exemplary toothbrush originally introduced in FIG. 5, the toothbrush being illustrated in an as manufactured state.

A toothbrush bristle restoration body toothbrush gripping formation 116 is formed in each distal, free end of each respective toothbrush bristle restoration body sidewall portion 114. The toothbrush bristle restoration body toothbrush gripping formation 116 can be of any suitable size and shape to engage with the toothbrush assembly 400, as illustrated in FIGS. 5 and 6. Each toothbrush bristle restoration body toothbrush gripping formation 116 is designed to retain the toothbrush bristle restoration apparatus 100 in position on the toothbrush assembly 400. In the exemplary illustrations, the toothbrush bristle restoration body toothbrush gripping formation 116 is formed as a groove, including a first lateral edge, a second lateral edge and a longitudinal surface extending between the first lateral edge and the second lateral edge. The groove is of a size and shape to receive edges of a toothbrush body 410 of the toothbrush assembly 400, as illustrated in FIG. 6. A depth of each toothbrush bristle restoration body toothbrush gripping formation 116 of the toothbrush bristle restoration body sidewall portion 114 is such to engage with the edge of the toothbrush body 410 while avoiding contact with or abutting an edge of the toothbrush bristles 420. The lower or outer lateral edge of the toothbrush bristle restoration body toothbrush gripping formation 116 retains the toothbrush bristle restoration apparatus 100 from separating from the toothbrush assembly 400. The upper or inner lateral edge of the toothbrush bristle restoration body toothbrush gripping formation 116 retains the toothbrush bristle restoration apparatus 100 from potentially becoming separated from the toothbrush assembly 400. Alternatively, the interior surface of the toothbrush bristle restoration body top portion 112 can be designed to rest against the distal, free ends of the bristles.

In the exemplary illustrations, the toothbrush bristle restoration apparatus 100 includes a pair of toothbrush bristle restoration pads 130. Each toothbrush bristle restoration pad 130 of the pair of toothbrush bristle restoration pads 130 includes at least one toothbrush bristle restoration pad body assembly member 136 carried by a toothbrush bristle restoration pad body 132. Each toothbrush bristle restoration pad body 132 includes a toothbrush bristle restoration pad body bristle contacting surface 134, wherein the toothbrush bristle restoration pad body bristle contacting surface 134 is shaped to follow an outer contour of the sets of bristles toothbrush bristles 420 of the toothbrush assembly 400. In the exemplary illustration, the sets of bristles are arranged in a linear alignment, where the outer edge of the sets of bristles defines a plane. The associated toothbrush bristle restoration pad body bristle contacting surface 134 is planar. In other applications, the arrangement of the bristles can be in an oval shaped pattern, a circular pattern, a diamond shaped pattern, or any other practical pattern, or a combination thereof. To accommodate these arrangements, the toothbrush bristle restoration pad body bristle contacting surface 134 would be of a mirrored shape, including having a partially oval shape, a partially circular shape, a partially diamond shape, or any combination thereof.

The toothbrush bristle restoration pad body assembly member 136 is provided for assembly of each toothbrush bristle restoration pad 130 to the toothbrush bristle restoration body 110. In the exemplary illustration, a toothbrush bristle restoration pad body assembly bore/hole 138 is formed through each toothbrush bristle restoration pad body assembly member 136. A toothbrush bristle restoration body restoration panel aperture 120 is provided through the respective toothbrush bristle restoration body sidewall portion 114 for each toothbrush bristle restoration pad body assembly member 136. A toothbrush bristle restoration body restoration panel aperture pin central groove 122 and a pair of toothbrush bristle restoration body restoration panel aperture pin end grooves 124 are formed in an exterior surface of the respective toothbrush bristle restoration body sidewall portion 114. A toothbrush bristle restoration pad assembly pin 140 is inserted through each toothbrush bristle restoration pad body assembly bore/hole 138 of each toothbrush bristle restoration pad body assembly member 136 and seated within the toothbrush bristle restoration body restoration panel aperture pin central groove 122 and pair of toothbrush bristle restoration body restoration panel aperture pin end grooves 124. The toothbrush bristle restoration pad assembly pin 140 provides a pivotal assembly between the respective toothbrush bristle restoration pad 130 and the toothbrush bristle restoration body sidewall portion 114. The toothbrush bristle restoration pad 130 can be assembled to the toothbrush bristle restoration body 110 using any other suitable assembly interface. Design considerations for the assembly interface include any of the following arrangements: the toothbrush bristle restoration pad 130 can be rigidly assembled to the toothbrush bristle restoration body 110, the toothbrush bristle restoration pad 130 can be pivotally assembled to the toothbrush bristle restoration body 110, the toothbrush bristle restoration pad 130 can be slideably assembled to the toothbrush bristle restoration body 110, or the toothbrush bristle restoration pad 130 can be assembled to the toothbrush bristle restoration body 110 using any other suitable assembly interface. In yet another assembly arrangement, each toothbrush bristle restoration pad 130 can be assembled to an intermediary member, where the intermediary member is then assembled to the toothbrush bristle restoration body 110.

Each handle 150 of the pair of handles 150 is designed and configured to apply a force to the distal, free end of the respective toothbrush bristle restoration body sidewall portion 114. A distal, free end of each handle 150 is assembled to the respective distal free end of the toothbrush bristle restoration body sidewall portion 114. A proximal end of each handle 150 is designed to be gripped by the user. An intermediary section is of a size and shape to engage with a region on the toothbrush bristle restoration body 110 creating a fulcrum or pivot point 182 for converting a compression force 180 applied to the proximal end of the handle 150 to a tensile force 184 provided at the distal, free end of the handle 150. In the exemplary illustration, the handle 150 is formed of a continuous rod, preferably of a rigid metal material. The handle 150 is formed including a pair of handle arm sections 152. A handle hinge assembly section 154 is formed at each distal, free end of the handle arm section 152. A handle grip section 156 if formed as a section that is continuous between each proximal end of the handle arm section 152. The handle 150 is preferably fabricated by forming a metal rod.

Each handle 150 is assembled to the toothbrush bristle restoration body 110 by inserting the handle hinge assembly section 154 into a respective handle assembly feature bore/hole 128 extending into or through a handle assembly feature 126 provided at the distal, free end of the toothbrush bristle restoration body sidewall portion 114. The cross section of the rod used to fabricate the handle 150 is preferably circular in shape. This creates a pivot between the handle 150 and the handle assembly feature bore/hole 128. A central region of each handle arm section 152 would rest against a transition between the toothbrush bristle restoration body top portion 112 and the toothbrush bristle restoration body sidewall portion 114, as shown in FIGS. 3 through 6.

One function of the toothbrush bristle restoration apparatus 100 is to maintain the quality of toothbrush bristles 420 of the toothbrush assembly 400. A toothbrush assembly 400, as manufactured, is presented in FIG. 7. Sets of bristles 420 are inserted into one side of a toothbrush body 410 of a toothbrush assembly 400 and remain cantilevered out. The bristles are inserted in groupings. The bristles of each group are tightly packed against one another and are substantially parallel with one another as illustrated. The bristles can be of like lengths or of different lengths. The bristles can be of a like cross sectional shape and size or of differing cross sectional shapes and/or of differing cross sectional sizes. It is desirable to maintain the bristles 420 in a parallel, tightly grouped arrangement. It is also desirable to decontaminate the bristles 420 of any unwanted micro-organisms, such as bacteria, fungi, and viruses.

Figure 8:
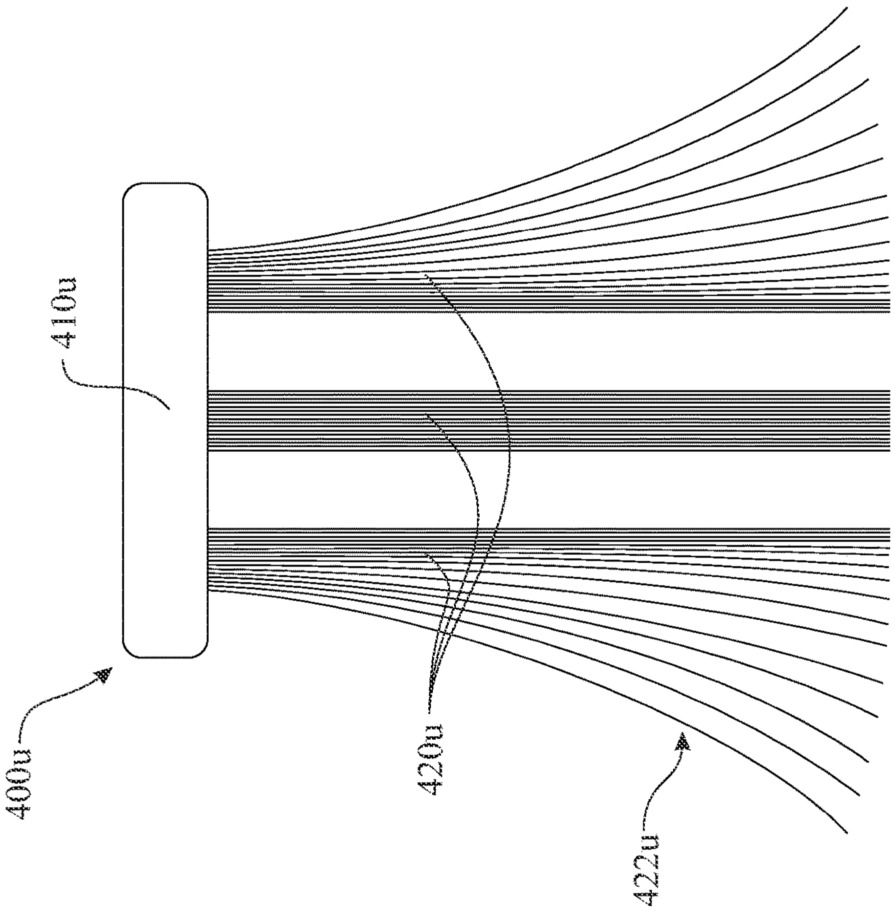
FIG. 8 presents an end view of the exemplary toothbrush originally introduced in FIG. 5, the toothbrush being illustrated in a well used state.

An exemplary toothbrush 400*u* is illustrated in FIG. 8. The used toothbrush 400*u* is the same as the new toothbrush 400, just illustrated after a number of uses. Like elements of the used toothbrush 400*u* and the new toothbrush 400 are the same, wherein the elements of the used toothbrush 400*u* are identified by a suffix "u" "following the reference numeral. Bristles 420*u* of used toothbrushes 400*u* that are not maintained tend to bend and separate from the groupings, as shown in FIG. 8.

Figure 4:
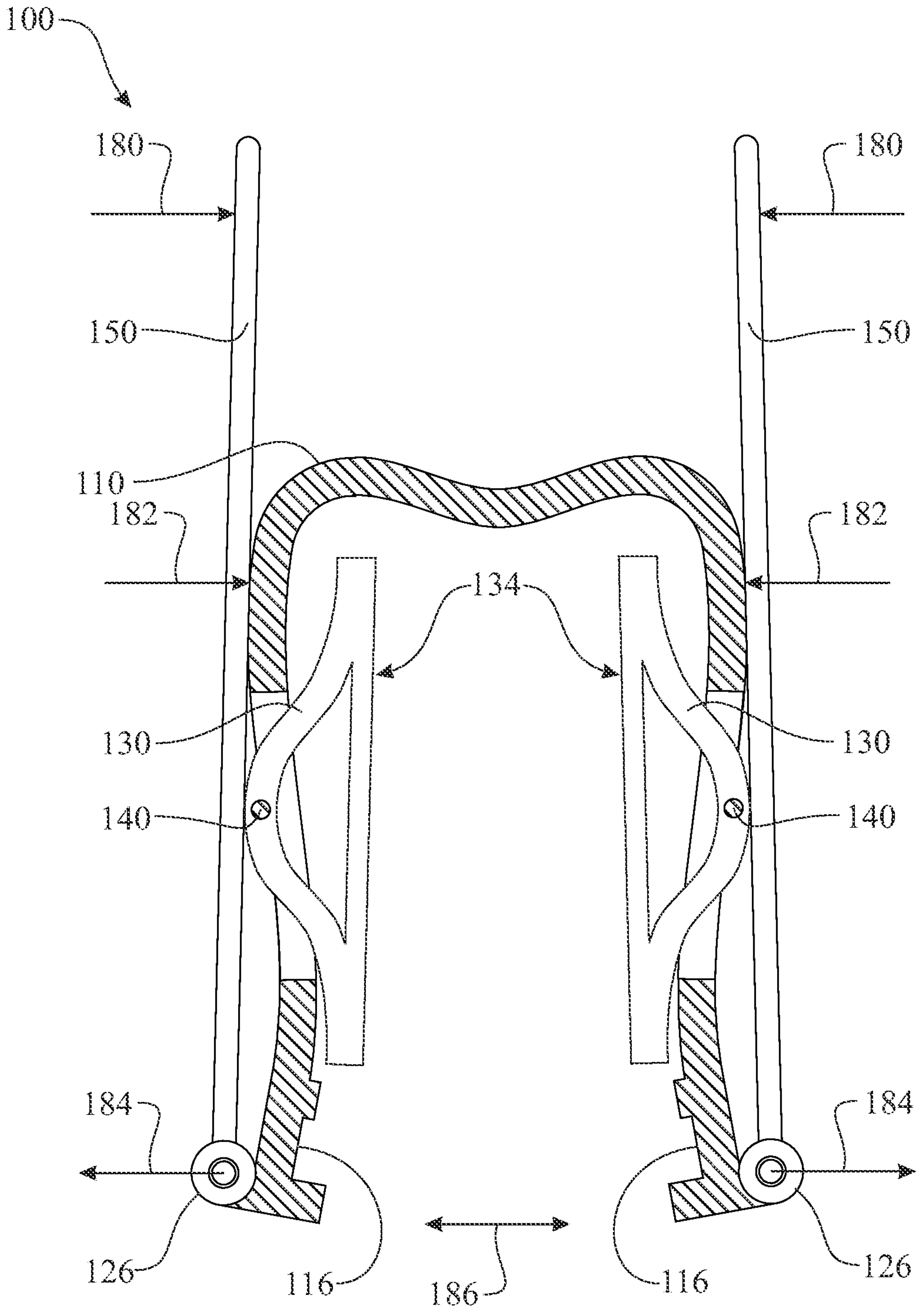
FIG. 4 presents a sectioned end view of the first exemplary toothbrush bristle restoration apparatus originally introduced in FIG. 1, the first exemplary toothbrush bristle restoration apparatus being shown in an expanded state.

The toothbrush bristle restoration apparatus 100 is shown in use in FIGS. 2 through 6. In use, the applied compression force 180 is applied to each handle grip section 156 a shown in FIG. 3. Contact between the handle arm section 152 and the toothbrush bristle restoration body 110 at the fulcrum point 182 translates the applied compression force 180 into the resulting tensile force 184 at the distal, free end of each toothbrush bristle restoration body sidewall portion 114. The created resulting tensile force 184 expands 186 the gap between the distal, free ends of the toothbrush bristle restoration body sidewall portions 114, as shown in FIG. 4. The toothbrush assembly 400 is inserted between the toothbrush bristle restoration body toothbrush gripping formations 116, locating the toothbrush bristles 420 between the toothbrush bristle restoration pad body bristle contacting surfaces 134 of the toothbrush bristle restoration pads 130. Once the toothbrush body 410 of the toothbrush assembly 400 is in alignment with the toothbrush bristle restoration body toothbrush gripping formations 116 of the toothbrush bristle restoration body sidewall portions 114, the applied compression force 180 is removed from the handle grip section 156 (removed compression force 190) and the spring or plastic properties of the material and shape of the toothbrush bristle restoration body 110 create a spring properties generated restoration force 194. The spring properties generated restoration force 194 causes a distal free end closure 196. The distal free end closure 196 draws the toothbrush bristle restoration body toothbrush gripping formation 116 about the edges of the toothbrush body 410, thus temporarily assembling the toothbrush bristle restoration apparatus 100 to the toothbrush assembly 400. Additionally, the distal free end closure 196 draws the toothbrush bristle restoration pad body bristle contacting surface 134 towards one another applying a restoration force to the toothbrush bristles 420 of the toothbrush assembly 400. The toothbrush bristle restoration pad body bristle contacting surface 134 would be shaped to mirror a peripheral shape of the sets of toothbrush bristles 420, as shown in FIG. 6. The inclusion of a pivotal interface between the toothbrush bristle restoration pad 130 and the toothbrush bristle restoration body sidewall portion 114 enables the toothbrush bristle restoration pad body bristle contacting surface 134 to optimize and equalize a force applied across the toothbrush bristles 420. A heater and any associated ancillary elements can be integrated into the toothbrush bristle restoration apparatus 100 or provided as a separate subassembly, wherein the heater elevates a temperature of the toothbrush bristle restoration pad 130. The heated toothbrush bristle restoration pad 130 aids in restoring and maintaining a shape of the toothbrush bristles 420.

Each of the pair of the toothbrush bristle restoration pads 130 can be exchangeable or interchangeable with a pair of toothbrush bristle restoration pads 130 wherein the replacing or selected toothbrush bristle restoration pad body bristle contacting surface 134 has a shape designed to follow a contour of a specific arrangement of sets or bristles 420 of the toothbrush 400. Several examples are illustrated in FIGS. 9A, 9B, 9C, and 9D. The elements illustrated in each of FIGS. 9A, 9B, 9C, and 9D are of the same function while having a distinct arrangement. Like elements are numbered the same wherein the elements of each variation are identified by a respective unique suffix.

Figure 9A:
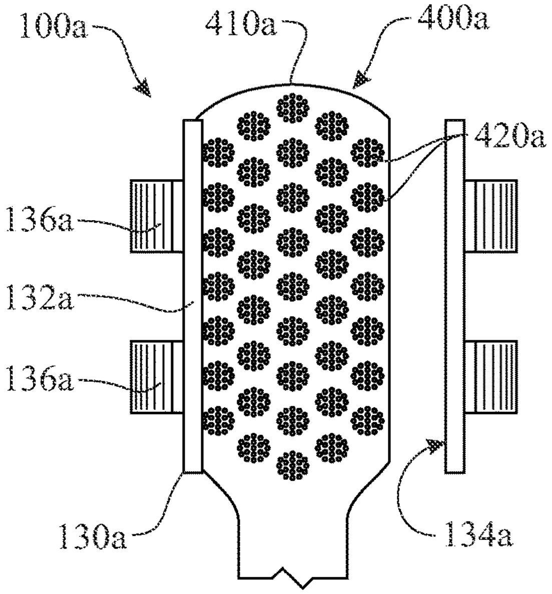
FIG. 9A presents a top view of a first exemplary toothbrush, the first exemplary toothbrush having linear and parallel edges.

As illustrated in FIG. 9A, a linear edged toothbrush bristle restoration apparatus 100*a* includes a linear edged toothbrush bristle restoration pad 130*a* having a specifically shaped linear edged toothbrush bristle restoration pad body bristle contacting surface 134*a* to restore bristles 420*a* of a linear edged toothbrush assembly 400*a*. The linear edged toothbrush bristles 420*a* are arranged in a linear pattern. The respective linear edged toothbrush bristle restoration pad body bristle contacting surface 134*a* is designed to engage with a side surface of the bristles 420*a*, wherein each linear edged toothbrush bristle restoration pad body bristle contacting surface 134*a* has a linear surface extending between a first edge and a second edge in a direction parallel to a pivotal axis. Any non-discussed reference numeral represents a like element and is associated with the other elements in FIG. 9A by including a suffix "a" "following the reference numeral.

Figure 9B:
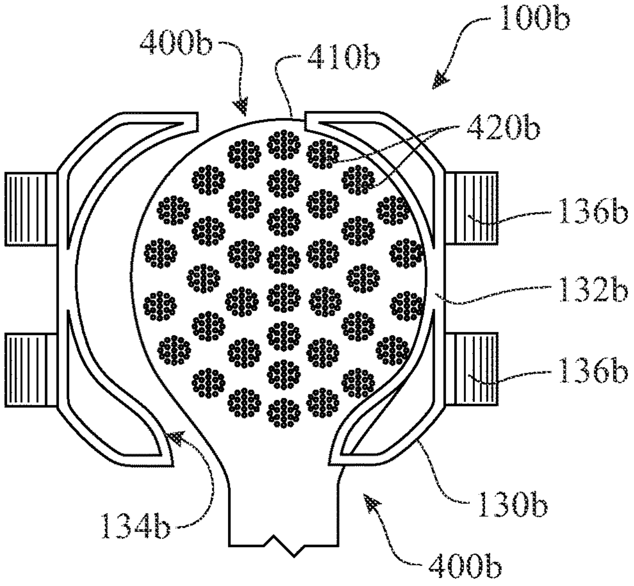
FIG. 9B presents a top view of a second exemplary toothbrush, the second exemplary toothbrush having a round shape.

As illustrated in FIG. 9B, a rounded toothbrush bristle restoration apparatus 100*b* includes a rounded toothbrush bristle restoration pad 130*b* having a specifically shaped rounded toothbrush bristle restoration pad body bristle contacting surface 134*b* to restore bristles 420*b* of a rounded toothbrush assembly 400*b*. The rounded toothbrush bristles 420*b* are arranged in a circular pattern. The respective rounded toothbrush bristle restoration pad body bristle contacting surface 134*b* is designed to engage with a side surface of the bristles 420*b*, wherein each rounded toothbrush bristle restoration pad body bristle contacting surface 134*b* has a curved surface extending between a first edge and a second edge. Any non-discussed reference numeral represents a like element and is associated with the other elements in FIG. 9B by including a suffix "b" "following the reference numeral.

Figure 9C:
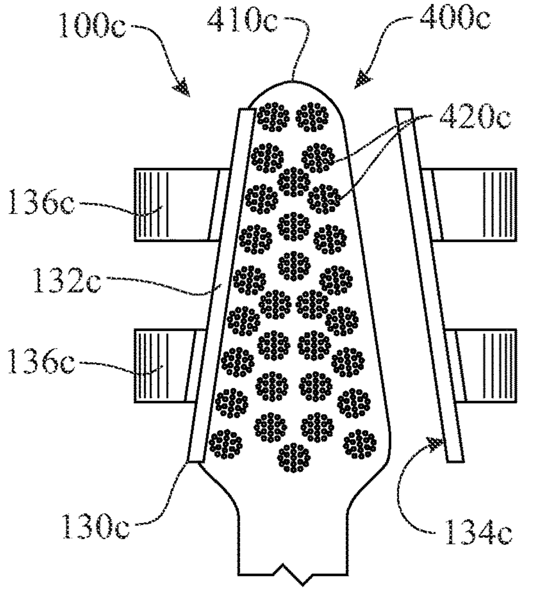
FIG. 9C presents a top view of a third exemplary toothbrush, the third exemplary toothbrush having a tapered shape.

As illustrated in FIG. 9C, a tapered toothbrush bristle restoration apparatus 100*c* includes a tapered toothbrush bristle restoration pad 130*c* having a specifically shaped tapered toothbrush bristle restoration pad body bristle contacting surface 134*c* to restore bristles 420*c* of a tapered toothbrush assembly 400*c*. The tapered toothbrush bristles 420*c* are arranged in a tapered pattern forming a v-shaped pattern. The respective tapered toothbrush bristle restoration pad body bristle contacting surface 134*c* is designed to engage with a side surface of the bristles 420*c*, wherein each tapered toothbrush bristle restoration pad body bristle contacting surface 134*c* has a linear surface extending between a first edge and a second edge, wherein a distance between the tapered toothbrush bristle restoration pad body bristle contacting surface 134*c* proximate the first edge and the pivot axle is greater than a distance between the tapered toothbrush bristle restoration pad body bristle contacting surface 134*c* proximate the second edge and the pivot axle. The difference in the distances orients the tapered toothbrush bristle restoration pad body bristle contacting surface 134*c* at an angle respect to an axis or rotation of the tapered toothbrush bristle restoration pad 130*c*, wherein the angle follows an angle of the taper of the tapered toothbrush bristles 420*c*. Any non-discussed reference numeral represents a like element and is associated with the other elements in FIG. 9C by including a suffix "c" "following the reference numeral.

Figure 9D:
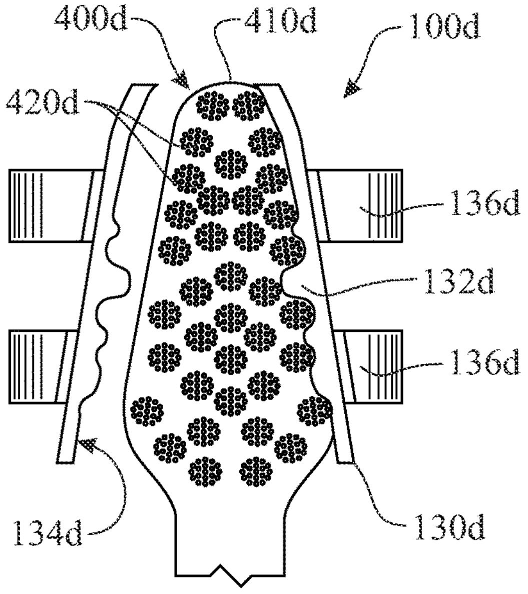
FIG. 9D presents a top view of a fourth exemplary toothbrush, the fourth exemplary toothbrush having an irregularly shaped bristle arrangement.

As illustrated in FIG. 9D, an irregularly shaped toothbrush bristle restoration apparatus 100*d* includes an irregularly shaped toothbrush bristle restoration pad 130*d* having a specifically shaped irregularly shaped toothbrush bristle restoration pad body bristle contacting surface 134*d* to restore bristles 420*d* of a tapered toothbrush assembly 400*c*. The irregularly shaped toothbrush bristles 420*d* are arranged in an irregular or non-geometric pattern. The respective irregularly shaped toothbrush bristle restoration pad body bristle contacting surface 134*d* is designed to engage with a side surface of the bristles 420*d*, wherein each irregularly shaped toothbrush bristle restoration pad body bristle contacting surface 134*d* has shape that follows a contour of the irregularly shaped toothbrush bristles 420*d* of the irregularly shaped toothbrush assembly 400*d*. In one instance, the irregularly shaped toothbrush bristle restoration pad 130*d* can be fabricated using a mold designed for the specific arrangement of irregularly shaped toothbrush bristles 420*d* of the irregularly shaped toothbrush assembly 400*d*. In a second instance, the irregularly shaped toothbrush bristle restoration pad 130*d* can include an irregularly shaped toothbrush bristle restoration pad body bristle contacting surface 134*d* fabricated of a moldable material. The moldable material may be softened by placing the toothbrush bristle restoration pads 130 in heated water, in an oven, in a microwave, or by subjecting the toothbrush bristle restoration pads 130 to any heat source, then placing the toothbrush bristle restoration pad body bristle contacting surface 134 against a toothbrush bristles outer surface 422 of the irregularly shaped toothbrush bristles 420*d*. When the material cools, the material forming the irregularly shaped toothbrush bristle restoration pad body bristle contacting surface 134*d* hardens and retains the molded shape. Any non-discussed reference numeral represents a like element and is associated with the other elements in FIG. 9D by including a suffix "d" "following the reference numeral.

Figure 10:
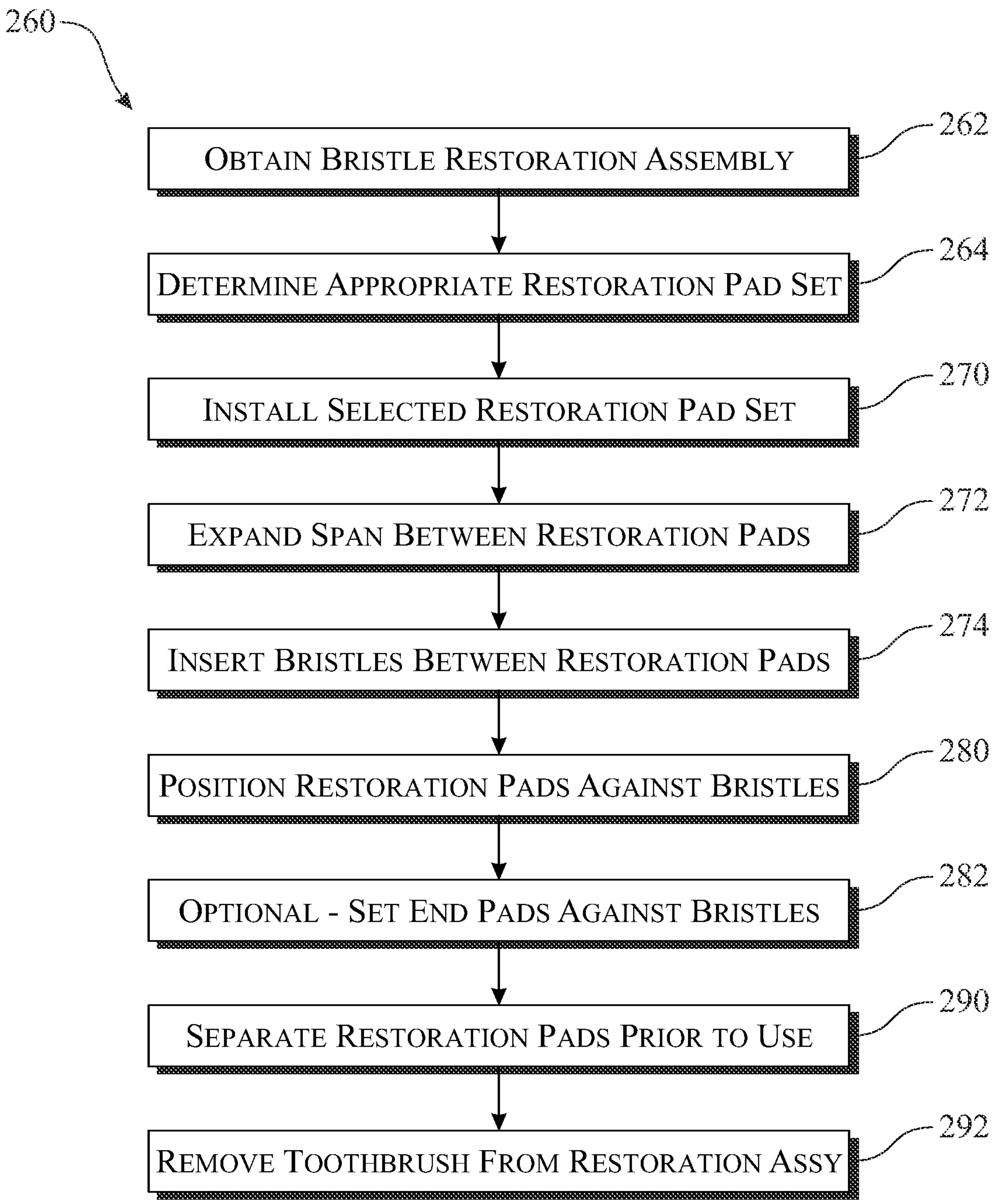
FIG. 10 presents a flow diagram of an exemplary toothbrush bristle restoration process.
Figure 11:
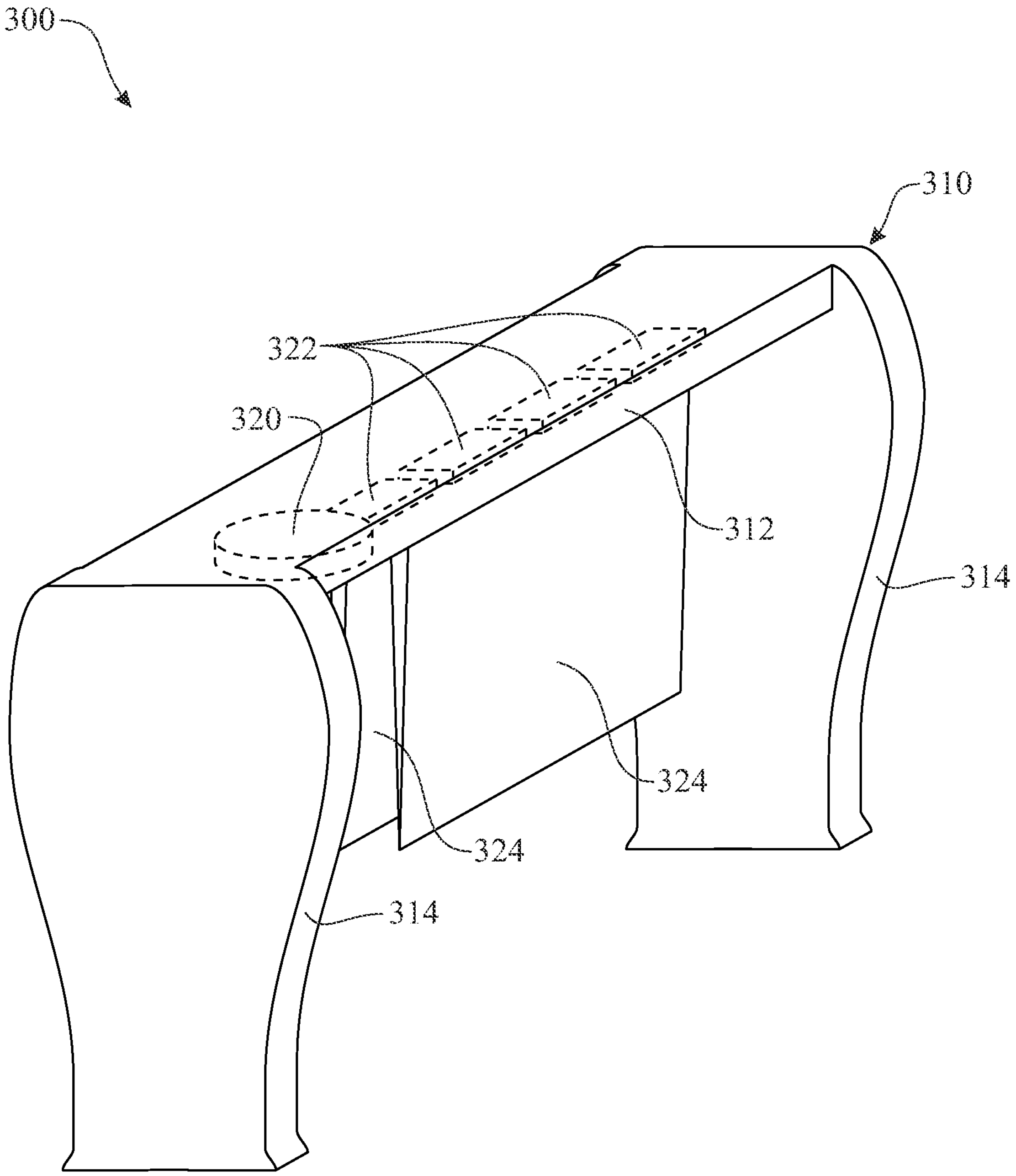
FIG. 11 presents an isometric front, top, side assembled view of an exemplary toothbrush sanitizing assembly.

A bristle restoration flow diagram 260, presented in FIG. 10, describes an overall process for restoring and maintaining a desired, original shape of toothbrush bristles 420 of the toothbrush assembly 400. The bristle restoration flow diagram 260 refers to any of the variants presented in this disclosure as well as any other variants that accomplish the same bristle restoration and maintenance application. The bristle restoration flow diagram 260 initiates with an obtain bristle restoration assembly step 262. The bristle restoration assembly can be any of the variants presented in this disclosure as well as any other variants that accomplish the same bristle restoration and maintenance application. The bristle restoration and maintenance assembly can be provided with one or more sets of restoration pads, the restoration pads being designed for assembly to the respective restoration assembly body included therewith. A user would determine an appropriate set of restoration pad(s) (step 264) based upon the shape of the toothbrush body 410 of the toothbrush assembly 400 as well as the arrangement of the toothbrush bristles 420 of the toothbrush assembly 400. The selected pair of restoration pads would be installed into the body of the restoration and maintenance assembly (step 270). The installation step 270 would be accomplished in a manner consistent with the associated assembly interface design. The user would separate the pair restoration pads (step 272) using a process conducive with the design of the bristle restoration assembly. Once a span between the pair of restoration pads is sufficient to allow insertion of the toothbrush bristles 420 of the toothbrush assembly 400, the user would insert bristles of toothbrush between restoration pads (step 274). The span between the pair of restoration pads would be reduced, drawing the restoration pads towards one another bringing the restoration pads against the toothbrush bristles outer surface 422 of the toothbrush bristles 420 (step 280). Movement of the restoration pads would be accomplished using a process conducive with the design of the bristle restoration assembly. An optional step of setting end pads against a proximal end and a distal end of the arrangement of the bristles 420 can be completed (step 282). This can be accomplished by inserting a separate element, inserting a wedge, assembly end caps to the body of the assembly, or any other method for providing a restoration force to ends of the arrangement of bristles 420. After a period of time (such as when the next time of desired use), the restoration pads would be separated from one another (step 290). Movement of the restoration pads would be accomplished using a process conducive with the design of the bristle restoration assembly. The spacing would enable removal of the toothbrush assembly 400 from the restoration and maintenance assembly (step 292).

Figure 17:
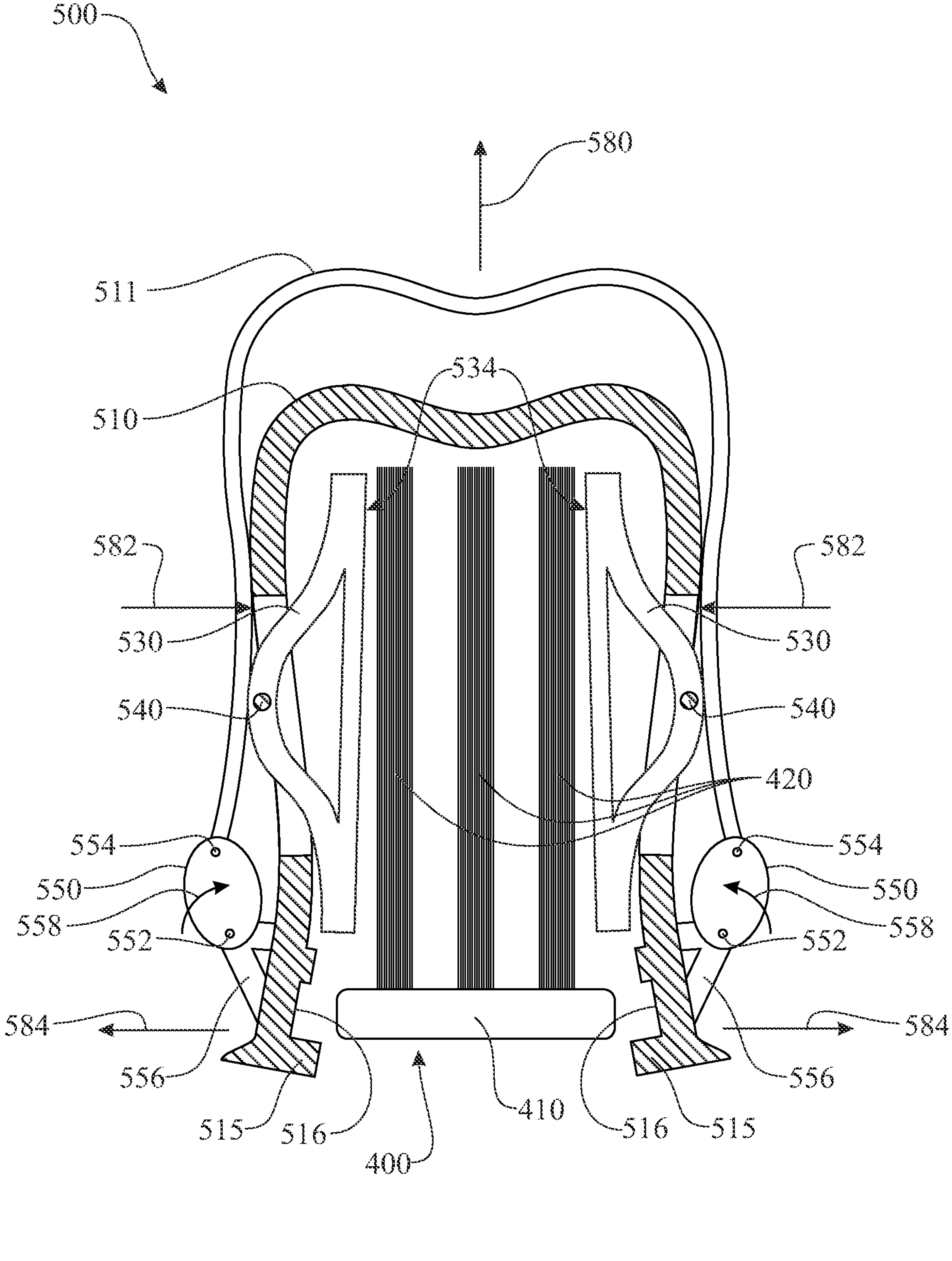
FIG. 17 presents a sectioned end view of a second exemplary toothbrush bristle restoration apparatus, the second exemplary toothbrush bristle restoration apparatus employing a pair of cams to expand and retract a pair of toothbrush grips and a pair of restoration pads, the illustration presenting the apparatus in an expanded state and the toothbrush being inserted into the second exemplary toothbrush bristle restoration apparatus.
Figure 18:
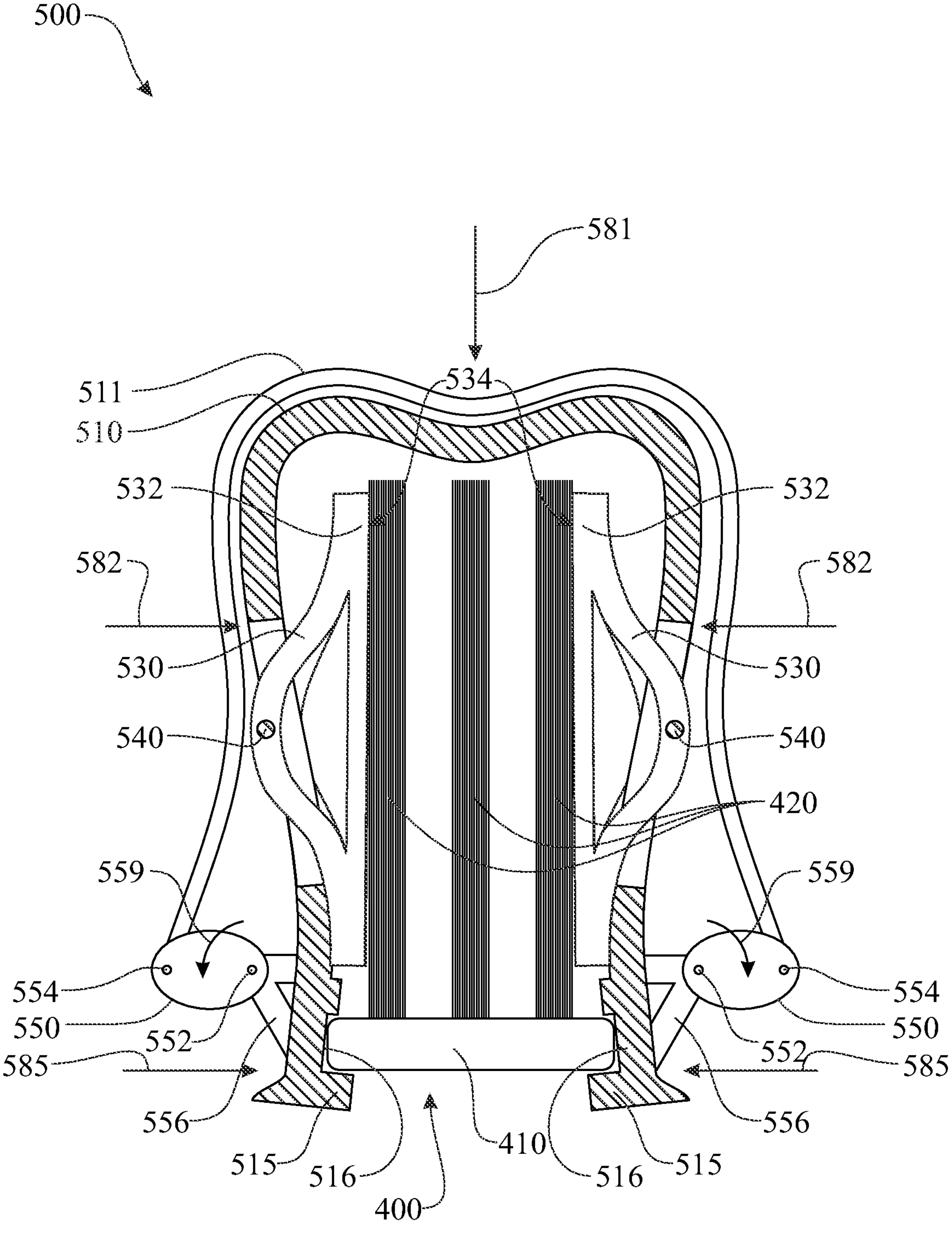
FIG. 18 presents a sectioned end view of the second exemplary toothbrush bristle restoration apparatus originally introduced in FIG. 17, the illustration presenting the apparatus in a retracted state and bristles of the toothbrush being subjected to a restoration process provided by the pair of restoration pads.

The illustrated version of the toothbrush bristle restoration apparatus 100 is one of many configurations. For example, a pair of cams can be employed to position the pair of toothbrush bristle restoration pads 130 respectively. The cams would toggle the pair of toothbrush bristle restoration pads 130 between an expanded configuration and a compression configuration. The cams would preferably be operated by a single component attached to each of the cams. A toothbrush cam operated bristle restoration apparatus 500, as illustrated in FIGS. 17 and 18, introduces an exemplary version of the toothbrush bristle restoration apparatus 100 adapted to employ a pair of toothbrush bristle restoration pad positioning cams 550 to operate the toothbrush cam operated bristle restoration apparatus 500. The toothbrush bristle restoration apparatus 100 and the toothbrush cam operated bristle restoration apparatus 500 have a number of like elements. Elements of the toothbrush cam operated bristle restoration apparatus 500 are numbered the same as like elements of the toothbrush bristle restoration apparatus 100, wherein elements of the toothbrush cam operated bristle restoration apparatus 500 are preceded by the numeral "5".

An interior surface of a toothbrush bristle restoration operational control member 511 slideably engages with an exterior surface of a toothbrush bristle restoration body 510. The toothbrush bristle restoration operational control member 511 is fabricated of a material and thickness providing spring like properties, where the toothbrush bristle restoration operational control member 511 can be deformed, wherein when deformed, the toothbrush bristle restoration operational control member 511 generates forces to return to a normal shape.

Contacting surfaces of the exemplary toothbrush bristle restoration body 510 and the exemplary toothbrush bristle restoration operational control member 511 are shaped to engage with one another and lock when a pair of toothbrush bristle restoration pad positioning cams 550 is rotated into an expanded orientation and also lock when the pair of toothbrush bristle restoration pad positioning cams 550 is rotated into a contracted orientation. The inflection shape which provides the locking function is identified by a positioning snap retention interface 582. Each toothbrush bristle restoration pad positioning cam 550 of the pair of toothbrush bristle restoration pad positioning cams 550 are rotationally assembled to the toothbrush bristle restoration operational control member 511 by a toothbrush bristle restoration pad positioning cam body pin 554, preferably the toothbrush bristle restoration pad positioning cam body pin 554 is located proximate a respective end of the toothbrush bristle restoration operational control member 511 as illustrated. An opposite region of each toothbrush bristle restoration pad positioning cam 550 is rotationally assembled to a toothbrush bristle restoration pad positioning cam mount 556 or other feature of the toothbrush bristle restoration body 510, wherein the pivot location (a toothbrush bristle restoration pad positioning cam mount pin 552) between the toothbrush bristle restoration pad positioning cam 550 and the toothbrush bristle restoration pad positioning cam mount 556 is preferably located proximate a toothbrush bristle restoration body toothbrush gripping formation 516 formed proximate a distal, free end of the toothbrush bristle restoration body 510. When the toothbrush bristle restoration operational control member 511 is pulled upwards in accordance with an upward opening motion 580 causing each toothbrush bristle restoration body toothbrush gripping formation 516 to move in accordance with a toothbrush bristle restoration pad spreading motion 584. The toothbrush bristle restoration pad spreading motion 584 results in engagement between the toothbrush bristle restoration operational control member 511 and the toothbrush bristle restoration body 510 at the shape of a deflection location of the toothbrush bristle restoration operational control member 511 and the toothbrush bristle restoration body 510 retains the toothbrush bristle restoration operational control member 511 in an expanded condition (as illustrated in FIG. 17). The upward motion of the toothbrush bristle restoration operational control member 511 rotates the toothbrush bristle restoration pad positioning cam 550 in accordance with the opening cam rotational motion 558, drawing the toothbrush bristle restoration body toothbrush gripping formation 516 and the toothbrush bristle restoration pad body bristle contacting surfaces 534 of each 530 outward. The expanded condition allows for insertion of the toothbrush body 410 between the toothbrush bristle restoration body toothbrush gripping formations 516 and the toothbrush bristle restoration pad body bristle contacting surfaces 534. When the toothbrush bristle restoration operational control member 511 is pushed downwards in accordance with a downward closing motion 581, The toothbrush bristle restoration body toothbrush gripping formations 516 move in accordance with a toothbrush bristle restoration pad closing motion 585. The toothbrush bristle restoration pad closing motion 585 causes engagement between the toothbrush bristle restoration operational control member 511 and the toothbrush bristle restoration body 510 at the shape of a deflection location of the toothbrush bristle restoration operational control member 511 and the toothbrush bristle restoration body 510 retains the toothbrush bristle restoration operational control member 511 in a retracted condition (toothbrush bristle restoration pad closing motion 585) (as illustrated in FIG. 18). The downward motion of the toothbrush bristle restoration operational control member 511 rotates the toothbrush bristle restoration pad positioning cam 550 in accordance with the closing cam rotational motion 559, returning the toothbrush bristle restoration body toothbrush gripping formations 516 and the toothbrush bristle restoration pad body bristle contacting surfaces 534 inward. The retracted condition of the toothbrush bristle restoration body 510 grips the toothbrush body 410 between the toothbrush bristle restoration body toothbrush gripping formations 516 and positioned the toothbrush bristle restoration pad body bristle contacting surface 534 against the toothbrush bristles outer surface 422 of the toothbrush bristles 420 of the toothbrush assembly 400 providing a restoration force to the toothbrush bristles 420. The toothbrush bristle restoration body toothbrush gripping flanges 515 maintain the toothbrush body 410 from slipping from the toothbrush bristle restoration body 510.

Each of the toothbrush bristle restoration apparatus 100, 200, and toothbrush cam operated bristle restoration apparatus 500 employ a reshaping of the respective body 110, 210, 510 for insertion and retention of the toothbrush assembly 400 and provides a restoration force to the toothbrush bristles 420. The same solution can be provided in any of a variety of form factors that enables insertion and retention of the toothbrush assembly 400 and provides a restoration force to the toothbrush bristles 420.

Figure 19:
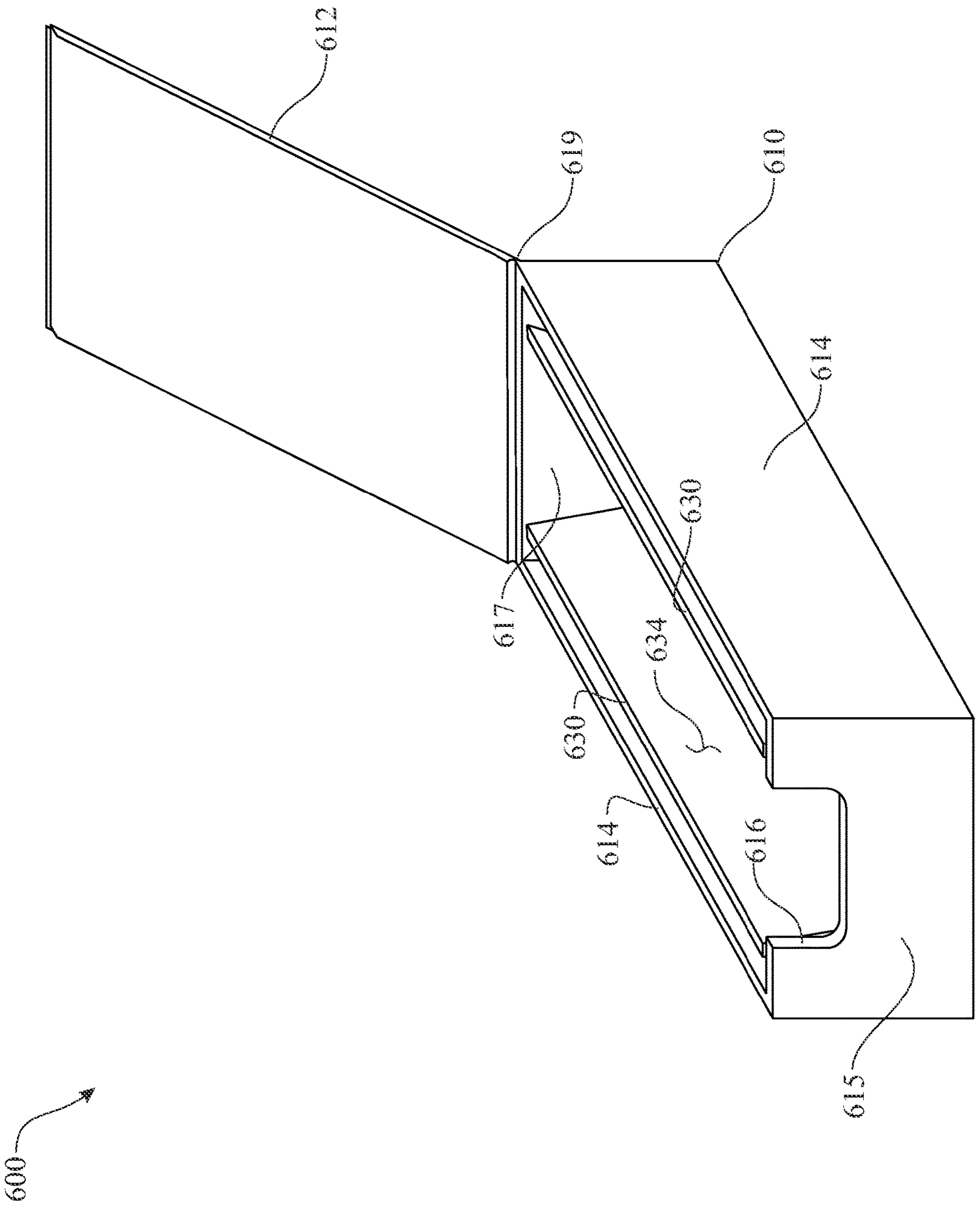
FIG. 19 presents a sectioned end view of a third exemplary toothbrush bristle restoration apparatus, the third exemplary toothbrush bristle restoration apparatus employing a pair of pivots to rotate a pair of restoration pads between a toothbrush insertion orientation and a bristle restoration orientation.
Figure 20:
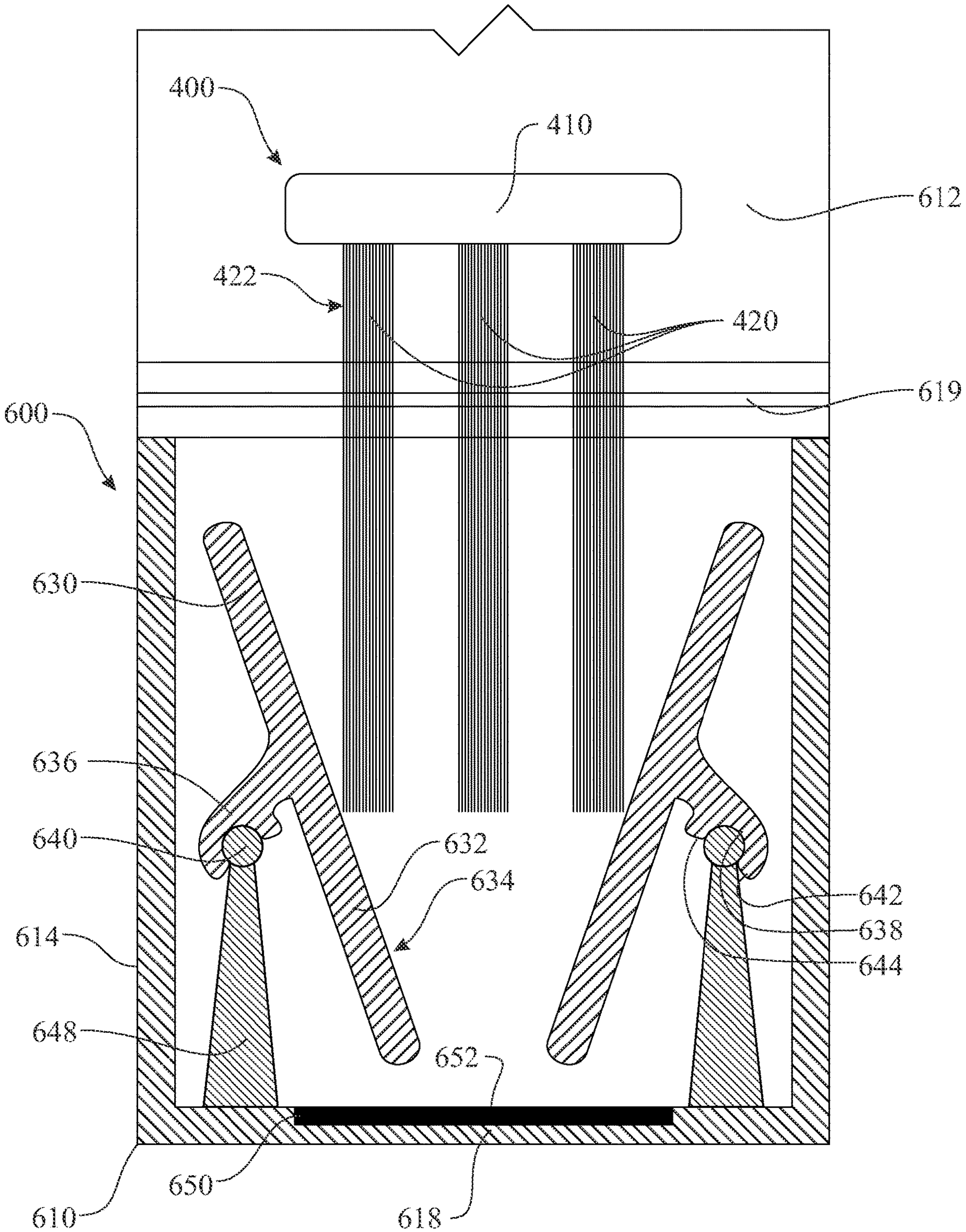
FIG. 20 presents a sectioned end view of the third exemplary toothbrush bristle restoration apparatus originally introduced in FIG. 19, the illustration presenting the pair of restoration pads in a toothbrush insertion orientation staged for insertion of the toothbrush.
Figure 21:
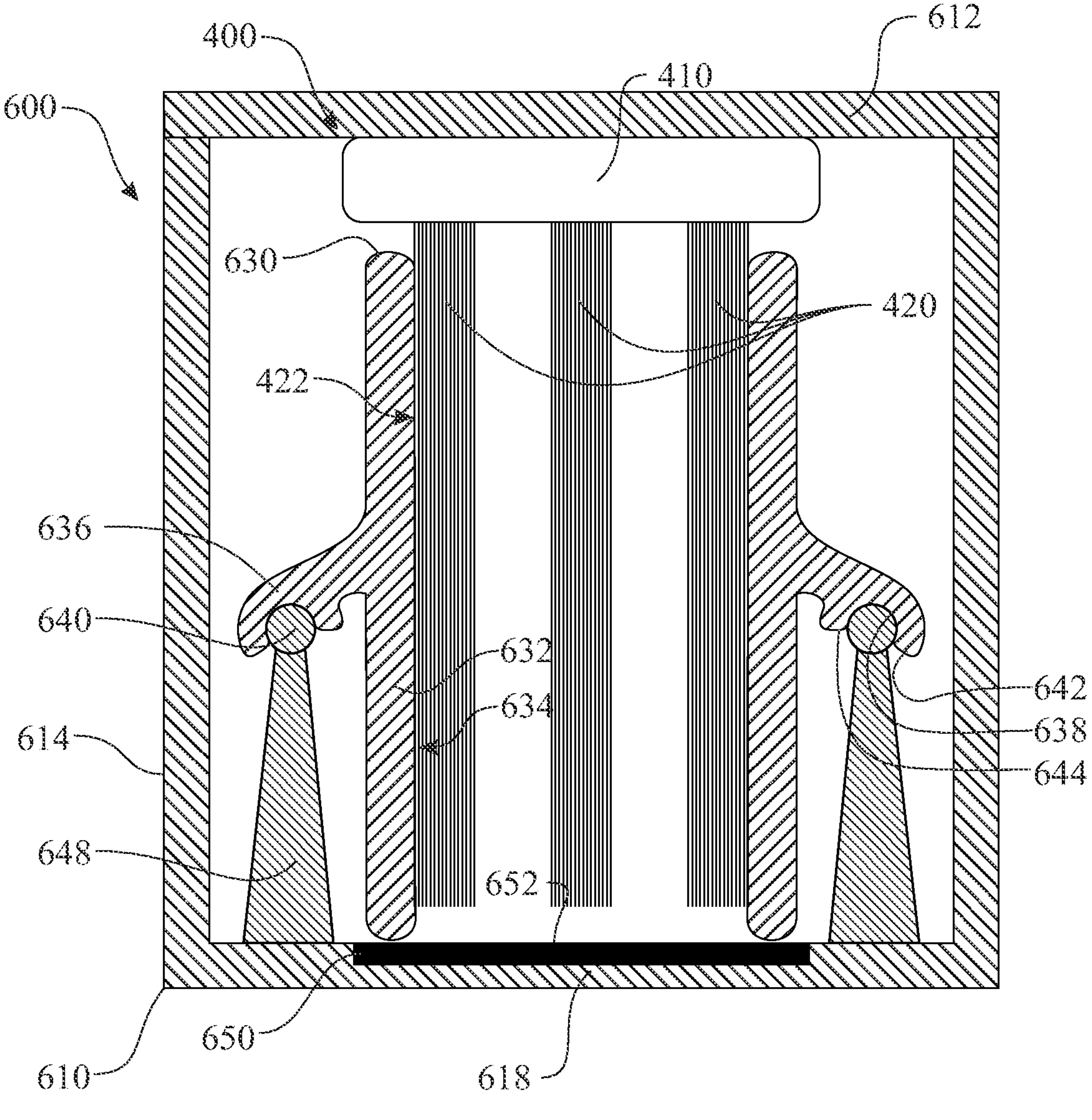
FIG. 21 presents a sectioned end view of the third exemplary toothbrush bristle restoration apparatus originally introduced in FIG. 19, the illustration presenting the pair of restoration pads in a bristle restoration orientation applying a restoration source to sets of bristles of the toothbrush.

A first example is a toothbrush bristle restoration apparatus 600 illustrated in FIGS. 19 through 21. The toothbrush bristle restoration apparatus 600 includes a toothbrush bristle restoration body bottom wall 618 hinged to a toothbrush bristle restoration body 610. The toothbrush bristle restoration body 610 comprises a pair of toothbrush bristle restoration body side walls 614, where front edges of each toothbrush bristle restoration body side wall 614 are contiguous with a respective edge of a toothbrush bristle restoration body front wall 615 and rear edges of each toothbrush bristle restoration body side wall 614 are contiguous with a respective edge of a toothbrush bristle restoration body rear wall 617. A toothbrush bristle restoration body bottom wall 618 is contiguous with a lower edge of each of the pair of toothbrush bristle restoration body side walls 614, the toothbrush bristle restoration body front wall 615, and the toothbrush bristle restoration body rear wall 617. A toothbrush bristle restoration body front wall toothbrush handle clearance 616 is formed in the toothbrush bristle restoration body front wall 615, where the toothbrush bristle restoration body front wall toothbrush handle clearance 616 is sized to accommodate any reasonably sized handle of the toothbrush assembly 400. A toothbrush bristle restoration body top wall 612 is pivotally assembled to the toothbrush bristle restoration body rear wall 617 by a toothbrush bristle restoration top hinge 619. In the exemplary illustration, the toothbrush bristle restoration top hinge 619 is a living hinge unitarily formed during a molding process fabricating the toothbrush bristle restoration body 610. The toothbrush bristle restoration top hinge 619 can be any suitable hinge design. Although the exemplary toothbrush bristle restoration body top wall 612 is assembled to the toothbrush bristle restoration body 610 using a toothbrush bristle restoration top hinge 619, it is understood that the toothbrush bristle restoration body top wall 612 can be assembled to the toothbrush bristle restoration body 610 using any suitable assembly process, such as a slide assembly, a snap assembly, or any other suitable method of assembling the toothbrush bristle restoration body top wall 612 to the toothbrush bristle restoration body 610.

The toothbrush bristle restoration apparatus 600 benefits from a pivotally assembled pair of toothbrush bristle restoration pads 630 enabling insertion and removal of the toothbrush assembly 400 and a hinged toothbrush bristle restoration body bottom wall 618 for retention of the toothbrush assembly 400 within an interior of the toothbrush bristle restoration apparatus 600, as shown in FIGS. 20 and 21. Each toothbrush bristle restoration pad 630 includes a toothbrush bristle restoration pad body assembly member 636 extending rearward from a toothbrush bristle restoration pad body 632. A toothbrush bristle restoration pad body bristle contacting surface 634 of the toothbrush bristle restoration pad body 632 is shaped to contact the toothbrush bristles outer surface 422 of a specifically shaped toothbrush assembly 400. Examples would be similar to the series of toothbrush bristle restoration pad body bristle contacting surfaces 134 which are presented in FIGS. 9A, 9B, 9C, and 9D above. A toothbrush bristle restoration pad body assembly snap 638 is formed in the toothbrush bristle restoration pad body assembly member 636. Each toothbrush bristle restoration pad 630 is pivotally assembled to the toothbrush bristle restoration body 610 by snapping the toothbrush bristle restoration pad body assembly snap 638 onto a toothbrush bristle restoration pad assembly pin 640. The toothbrush bristle restoration pad assembly pin 640 is supported by a toothbrush bristle restoration pad assembly pin support 648. Although the exemplary toothbrush bristle restoration pad assembly pin support 648 extends upwards from an interior surface of the toothbrush bristle restoration body bottom wall 618, the toothbrush bristle restoration pad assembly pin support 648 can be supported by any portion of the toothbrush bristle restoration body 610 or an element that is inserted into the toothbrush bristle restoration body 610. The toothbrush bristle restoration pad body assembly snap 638 is defined by a peripheral portion of the toothbrush bristle restoration pad body assembly member 636. A first end of the peripheral portion of the toothbrush bristle restoration pad body assembly member 636 provides a toothbrush bristle restoration pad body assembly released position rotational stop 642, and a second end of the peripheral portion of the toothbrush bristle restoration pad body assembly member 636 provides a toothbrush bristle restoration pad body assembly compression position rotational stop 644. The toothbrush bristle restoration pad body assembly released position rotational stop 642 limits rotation of the toothbrush bristle restoration pad 630 in an insertion condition and the toothbrush bristle restoration pad body assembly compression position rotational stop 644 limits rotation of the toothbrush bristle restoration pad 630 in a restoration condition. A biasing element (not shown) can be introduced, wherein the biasing element can be arranged to retain the toothbrush bristle restoration pad 630 in the insertion orientation until the toothbrush bristles 420 are inserted into the toothbrush bristle restoration apparatus 600. The biasing element can be a coil spring, a cantilevered spring, or any other suitable biasing element. The biasing element can be an independent component or integrated into either the toothbrush bristle restoration pad 630, the toothbrush bristle restoration pad assembly pin support 648, the toothbrush bristle restoration body 610 or any other element of the toothbrush bristle restoration apparatus 600, or unitarily fabricated as a feature of the toothbrush bristle restoration pad 630, the toothbrush bristle restoration pad assembly pin support 648, the toothbrush bristle restoration body 610 or any other element of the toothbrush bristle restoration apparatus 600.

A sanitizing pad 652 can be applied to the toothbrush bristle restoration apparatus 600. In the exemplary toothbrush bristle restoration apparatus 600, the sanitizing pad 652 is inserted into a sanitizing pad receiving recess 650 formed in the toothbrush bristle restoration body bottom wall 618. A finger groove can be included in the sanitizing pad receiving recess 650 to aid in removal and replacement of the sanitizing pad receiving recess 650 as needed. Although the exemplary toothbrush bristle restoration apparatus 600 places the sanitizing pad 652 into the sanitizing pad receiving recess 650 formed in the toothbrush bristle restoration body bottom wall 618, one or more sanitizing pads 652 can be applied to a surface or inserted into a provided recession at any suitable location within an interior of the toothbrush bristle restoration apparatus 600. The sanitizing pad 652 can be any material that would release a sanitizing chemical within the interior of the toothbrush bristle restoration apparatus 600. The sanitizing composition can be at least one of: an alcohol based solution, a chlorine based solution, a sodium hypochlorite based solution, a glutaraldehyde based solution, a hydrogen peroxide based solution, an iodophor based solution, an ortho-phthalaldehyde based solution, a peracetic or peroxyacetic acid based solution, a phenol based solution, a quaternary ammonium compound based solution, and the like or any chemically compatible combination thereof.

An adhesive would be applied to the attachment surface of the sanitizing pad 652. A protective covering can be applied to the adhesive, where the protective covering would be removed prior to adhesion onto the toothbrush bristle restoration apparatus 600.

In use, the toothbrush assembly 400 would be inserted into the interior of the toothbrush bristle restoration apparatus 600, positioning the toothbrush bristles outer surface 422 of the toothbrush bristles 420 against each of the toothbrush bristle restoration pad body bristle contacting surfaces 634. As the toothbrush assembly 400 is being inserted, the toothbrush bristles outer surface 422 causes each toothbrush bristle restoration pad 630 to rotate into a restoration position, where the toothbrush bristle restoration pad body bristle contacting surface 634 would apply a restoration force to the toothbrush bristles 420, as shown in FIG. 21.

Figure 22:
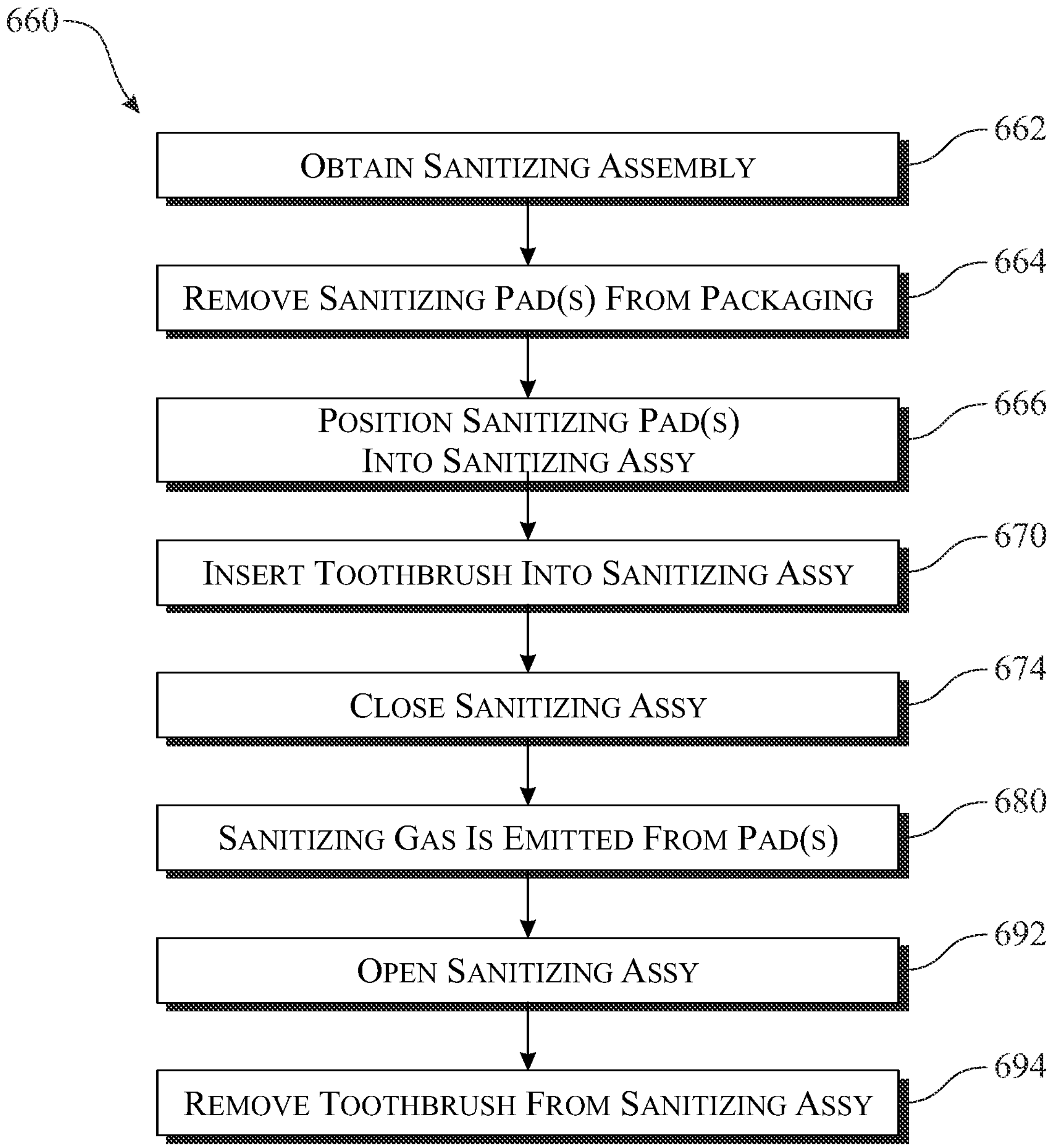
FIG. 22 presents a flow diagram of a second exemplary toothbrush bristle sanitizing process, wherein the second exemplary toothbrush bristle sanitizing system employs gaseous emissions of a sanitizing chemical provided by at least one replaceable sanitizing pad.

A bristle sanitization flow diagram 360 describes a sanitizing process which employs an electronically generated sanitizing emission. The toothbrush bristle restoration apparatus 600 introduces a sanitizing system employing chemical emissions. A bristle sanitization flow diagram 660, presented in FIG. 22, describes a process of employing chemical emissions for sanitizing bristles 420 of the toothbrush assembly 400. The bristle sanitization flow diagram 660 initiates with an obtain bristle sanitizing assembly step 662. In the exemplary illustrations, the toothbrush sanitizing pads 652, 654 are located within the toothbrush bristle restoration apparatus 600. The toothbrush sanitizing pads 652 can also be utilized with a custom enclosure, exclusive of the restoration function. The sanitizing pads (or any other disposable element comprising the sanitizing chemicals) are removed from a sealed package (step 664). The sanitizing pads are placed into the sanitizing assembly (step 666) in accordance with the design of the sanitizing pads (or other form factor). In one arrangement, the sanitizing pads are adhesively bonded to an interior surface of the sanitizing assembly. In another arrangement, sanitizing pellets can be snapped into a retention feature, inserted into a retention drawer or cavity, or retained within the interior using any suitable retention configuration.

The toothbrush assembly 400 is inserted into the sanitizing assembly in accordance with the design of the sanitizing assembly (step 670). In one exemplary illustration, the toothbrush assembly 400 is inserted into an interior of the toothbrush bristle restoration apparatus 600. The toothbrush bristle restoration body top wall 612 is closed, substantially sealing the toothbrush assembly 400 within the interior of the toothbrush bristle restoration apparatus 600 (step 674). A foam or other seal can be provided about the toothbrush bristle restoration body front wall toothbrush handle clearance 616, improving a quality of the seal between the toothbrush assembly 400 and the toothbrush bristle restoration apparatus 600. The toothbrush sanitizing pads 652, 654 emit sanitizing fumes (step 680), wherein the sanitizing fumes sanitize the bristles 420 and head 410 of the toothbrush assembly 400. When the user desired to use the toothbrush assembly 400, the sanitizing assembly is opened (step 692). The toothbrush assembly 400 is then removed from the sanitizing assembly for use (step 694).

The toothbrush bristle restoration body top wall 612 can be retained in a closed configuration by any suitable latching system. Examples of latching systems and hinges are taught in U.S. Pat. No. 5,924,567. Other hinged and latching systems can be integrated into the toothbrush bristle restoration apparatus 600.

Although the toothbrush bristle restoration apparatus 600, as illustrated, employs a chemical sanitizing system, the toothbrush bristle restoration apparatus 600 can employ an electrically generated sanitizing system, such as the system employed by the toothbrush sanitizing assembly 300. The toothbrush bristle restoration body 610 can be fabricated of an opaque material, retaining emitted light therein or of a translucent or transparent material, enabling emission of the light through the toothbrush bristle restoration body 610. The same can be applied to any of the versions of the toothbrush bristle restoration apparatuses presented herein.

The toothbrush bristle restoration body 610 can be shaped as desired. The external shape can be of any desired shape, including any geometric shape, a rectangular shape, a rounded shape, an elliptical shape, a diamond shape, an arrow shape, shaped to resemble an object, shaped to resemble a tooth, shaped to resemble an animal, shaped to resemble a vehicle, or any other shape that is desired or would be considered to help with marketing, identification of the apparatus, and the like. Any of the variants described herein can be shaped as described above, particularly the variants having an enclosed body.

Figure 23:
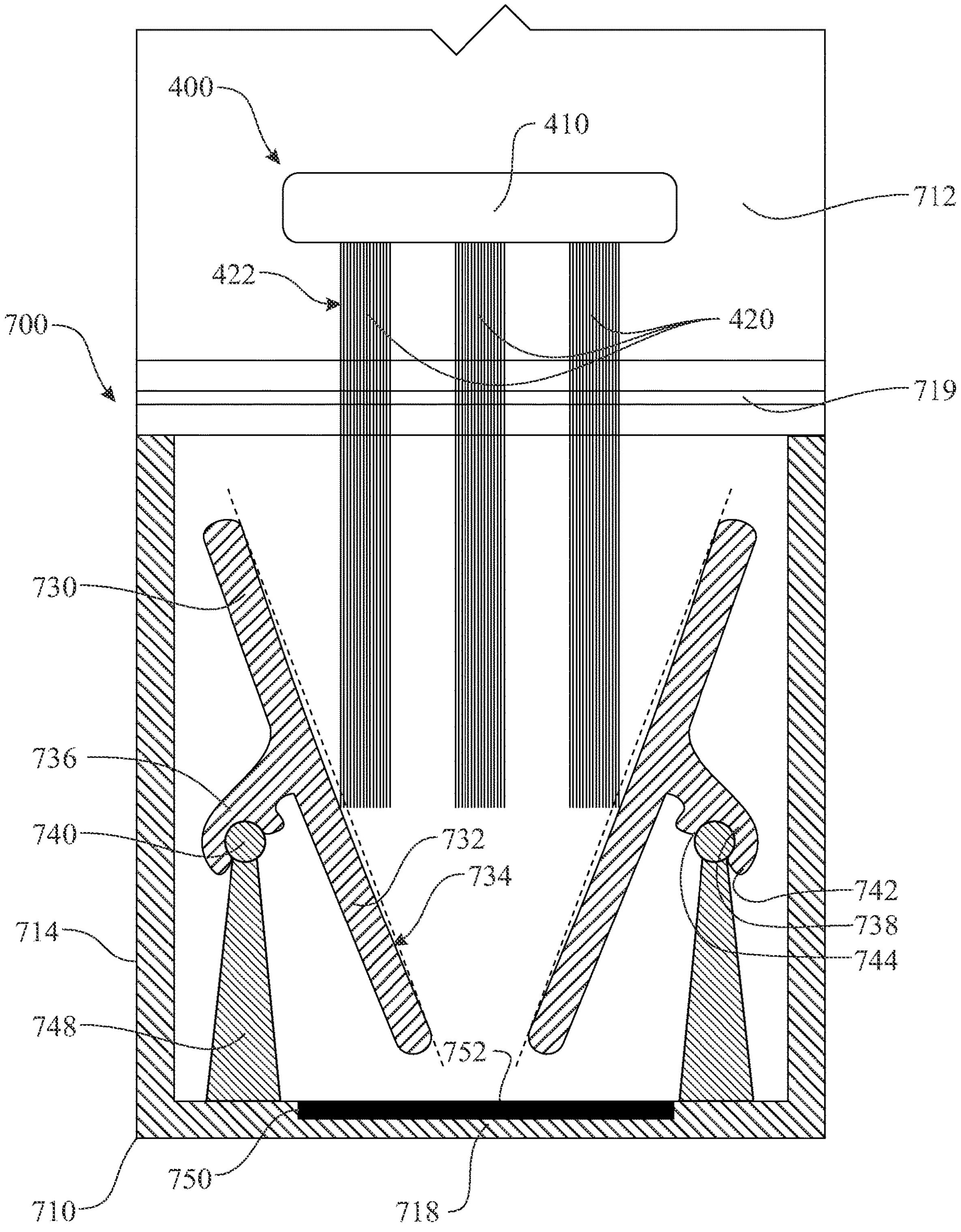
FIG. 23 presents a sectioned end view of a modified version of the third exemplary toothbrush bristle restoration apparatus originally introduced in FIG. 19, wherein the restoration pads comprise a concave bristle contacting surface, the illustration presenting the pair of restoration pads in a toothbrush insertion orientation staged for insertion of the toothbrush.
Figure 24:
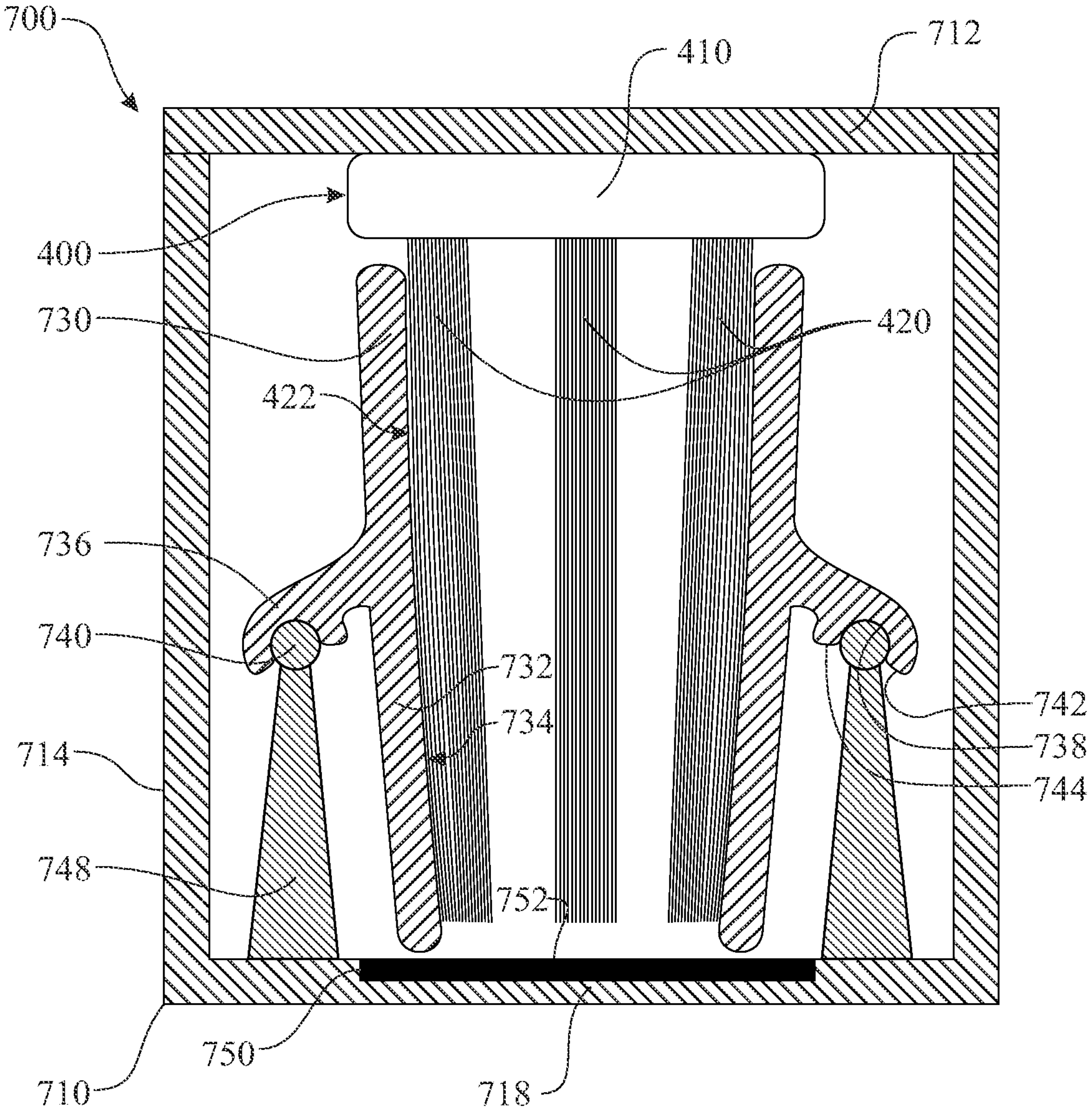
FIG. 24 presents a sectioned end view of the modified version of the third exemplary toothbrush bristle restoration apparatus originally introduced in FIG. 23, the illustration presenting the pair of restoration pads in a bristle restoration orientation applying a restoration source to sets of bristles of the toothbrush.

The exemplary toothbrush bristle restoration pad body bristle contacting surface 634 is linear or planar between a top edge and a bottom edge of the toothbrush bristle restoration pad body 632. It is understood that the toothbrush bristle restoration pad body bristle contacting surface 634 can be of any suitable shape between the top edge and a bottom edge of the toothbrush bristle restoration pad body 632, as introduced in a toothbrush bristle restoration apparatus 700, illustrated in FIGS. 23 and 24. The toothbrush bristle restoration apparatus 700 includes a majority of like elements of the toothbrush bristle restoration apparatus 600. Like elements of the toothbrush bristle restoration apparatus 700 and the toothbrush bristle restoration apparatus 600 are numbered the same, wherein elements of the toothbrush bristle restoration apparatus 700 are preceded by the numeral "7". Each toothbrush bristle restoration pad body bristle contacting surface 734 has a concave surface to help guide the bristles 420 between the pair of toothbrush bristle restoration pad body bristle contacting surfaces 734. The concave shape is referenced by a broken linear line. The concave surface of the toothbrush bristle restoration pad body bristle contacting surface 734 can also compress tips of the bristles 420 slightly inward (as illustrated in FIG. 24), overcompensating for a normally outward deflection associated with use.

Figure 25:
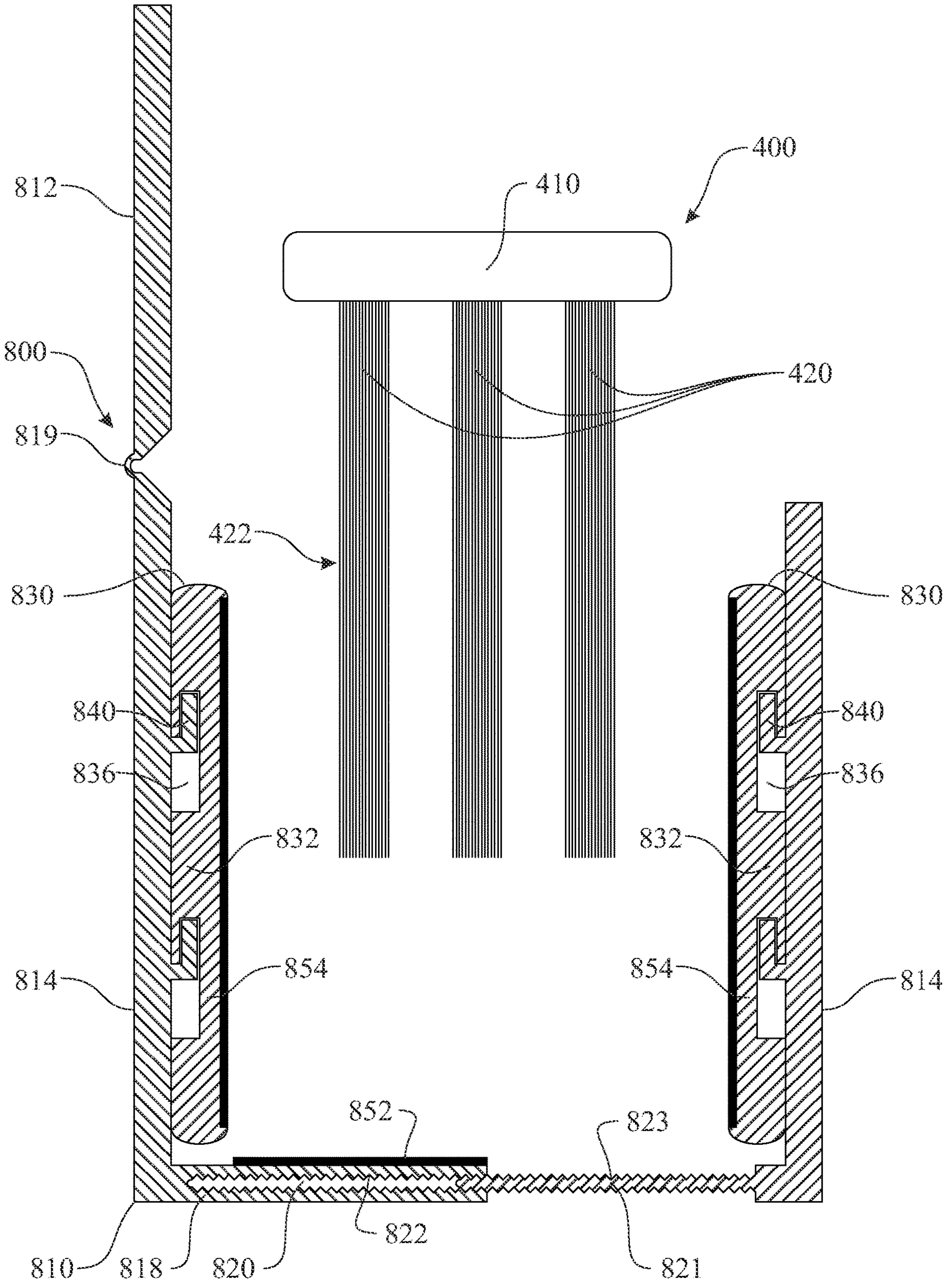
FIG. 25 presents a sectioned end view of a fourth exemplary toothbrush bristle restoration apparatus, the fourth exemplary toothbrush bristle restoration apparatus employing an adjustable bottom wall, the illustration presenting the base in a widened state wherein the pair of restoration pads are positioned in a toothbrush insertion orientation staged for insertion of the toothbrush.
Figure 26:
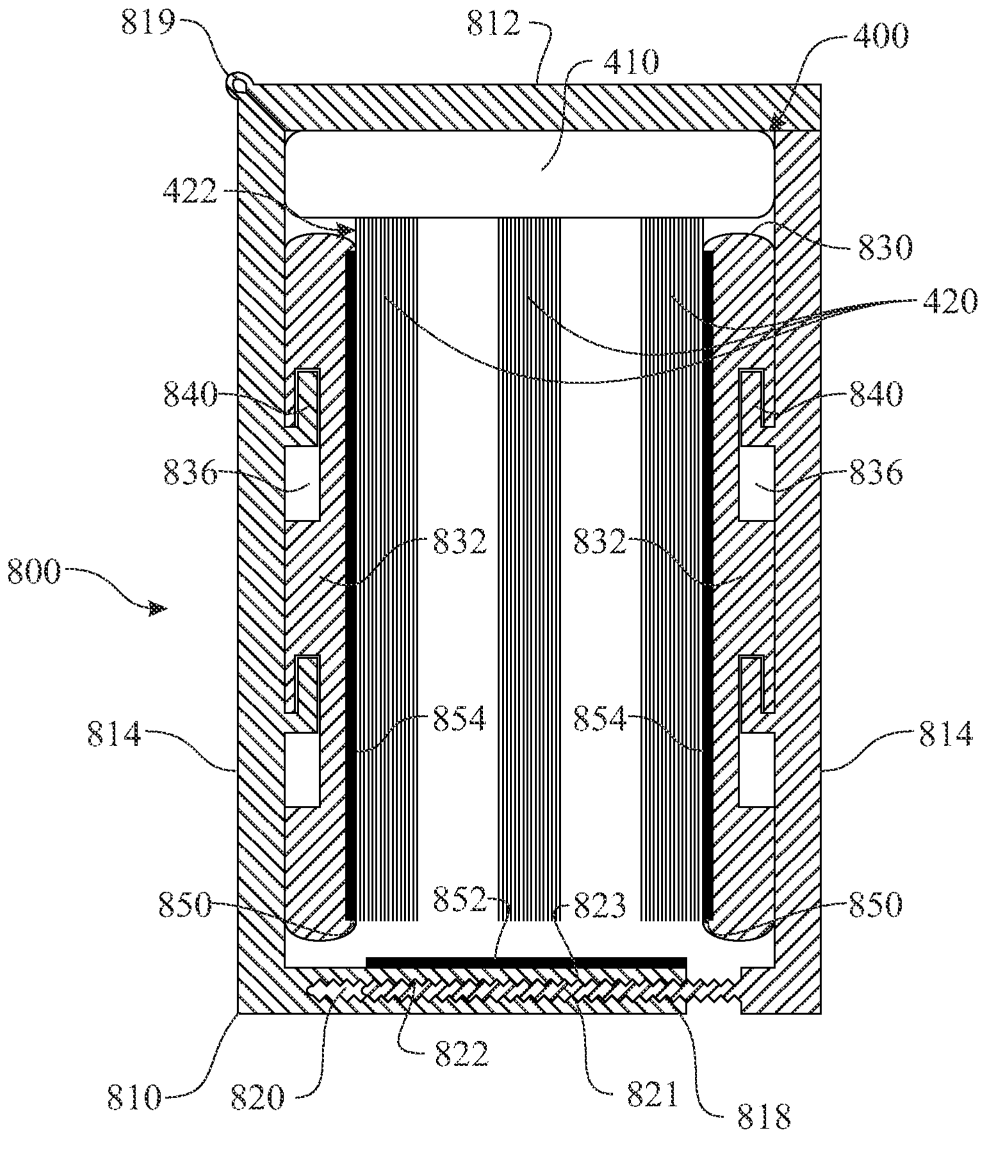
FIG. 26 presents a sectioned end view of the fourth exemplary toothbrush bristle restoration apparatus originally introduced in FIG. 25, the illustration presenting the base in a contracted state wherein the pair of restoration pads are positioned in a bristle restoration orientation applying a restoration source to sets of bristles of the toothbrush.

In another example, the pair of toothbrush bristle restoration pads 130 can be separated and placed together using a sliding adjustment interface, as introduced by a toothbrush bristle restoration apparatus 800 illustrated in FIGS. 25 and 26. The toothbrush bristle restoration apparatus 800 includes a portion of like elements of the toothbrush bristle restoration apparatus 600. Like elements of the toothbrush bristle restoration apparatus 800 and the toothbrush bristle restoration apparatus 600 are numbered the same, wherein elements of the toothbrush bristle restoration apparatus 800 are preceded by the numeral "8".

Each toothbrush bristle restoration pad 830 is assembled to a respective toothbrush bristle restoration body side wall 814 of the toothbrush bristle restoration body 810 of the toothbrush bristle restoration apparatus 800 using any suitable assembly interface. In the exemplary illustration, at least one keyhole recess toothbrush bristle restoration pad body assembly tab receiving recess 836 is formed in an assembly side of the toothbrush bristle restoration pad body 832 of the toothbrush bristle restoration pad 830. A toothbrush bristle restoration pad body assembly tab 840 extends inward from an interior surface of the toothbrush bristle restoration body side wall 814. A tab of each toothbrush bristle restoration pad body assembly tab 840 is inserted into the respective toothbrush bristle restoration pad body assembly tab receiving recess 836 and the associated toothbrush bristle restoration pad 830 is slid downward, positioning the tab of the toothbrush bristle restoration pad body assembly tab 840 into a vertically oriented portion of the toothbrush bristle restoration pad body assembly tab receiving recess 836, as illustrated in FIGS. 25 and 26. Although one exemplary assembly interface is illustrated for assembling the toothbrush bristle restoration pad 830 to the toothbrush bristle restoration body side wall 814, any suitable assembly interface can be employed to assemble each toothbrush bristle restoration pad 830 to the respective toothbrush bristle restoration body side wall 814. For example, double sided adhesive can be used. In another example, a dense hook and loop tape can be employed. In yet another example, magnets can be employed to retain each toothbrush bristle restoration pad 830 in position.

The toothbrush bristle restoration apparatus 800 toggles between an insertion condition and a restoration condition by slideably expanding and contracting the toothbrush bristle restoration body 810. The toothbrush bristle restoration body 810 is segmented into a left side and a right side. The toothbrush bristle restoration body bottom wall 818 includes a width adjustment tongue 821 that is slideably inserted into a width adjustment tongue receiving groove 820. A series of width adjustment tongue receiving groove teeth 822 are formed on an interior surface of the width adjustment tongue receiving groove 820. A series of width adjustment tongue teeth 823 are formed on an exterior surface of the width adjustment tongue 821. The width adjustment tongue receiving groove teeth 822 engage with the width adjustment tongue teeth 823 in a ratcheting manner. This enables a sliding motion between the width adjustment tongue 821 and the width adjustment tongue receiving groove 820. The elastic properties of the portion of the toothbrush bristle restoration body bottom wall 818 forming the width adjustment tongue receiving groove 820 enables a ratcheting function between the width adjustment tongue receiving groove teeth 822 and the width adjustment tongue teeth 823. The ratcheting function enables separation between the toothbrush bristle restoration body side walls 814 when a sufficient force is applied, while retaining the separation between the toothbrush bristle restoration body side walls 814 while be utilized to apply a restoration force to the toothbrush bristles 420.

Since spacing between the toothbrush bristle restoration body side walls 814 changes, the toothbrush bristle restoration top hinge 819 assembles the toothbrush bristle restoration body top wall 812 to one of the toothbrush bristle restoration body side wall 814. This accommodates for the change in spacing between the toothbrush bristle restoration body side walls 814.

In addition to a bottom wall supported sanitizing pad 852, a contact pad supported sanitizing pad 854 can be applied to a bristle contacting surface of each of the toothbrush bristle restoration pad body bristle contacting surface 834. In the exemplary illustrations, the bottom wall supported sanitizing pad 852 is applied to a non-recessed surface and the contact pad supported sanitizing pad 854 are applied to a recessed surface.

In use, the toothbrush bristle restoration pad 830 having a restoration surface shape that is appropriate for the particularly shaped toothbrush assembly 400. The selected pair of toothbrush bristle restoration pads 830 is assembled to the toothbrush bristle restoration body side wall 814 by the provided assembly interface. The pair of toothbrush bristle restoration pads 830 are separated by manually drawing the toothbrush bristle restoration body side walls 814 apart, as illustrated in FIG. 25. Once a sufficient span is between the pair of toothbrush bristle restoration pad 830, the toothbrush bristles 420 are inserted between the spatially arranged pair of toothbrush bristle restoration pad 830. A compression force is applied to each of the toothbrush bristle restoration body side wall 814, compressing the toothbrush bristle restoration pad body 832 (including the contact pad supported sanitizing pad 854 when included) against the toothbrush bristles outer surface 422 of the toothbrush bristles 420, as illustrated in FIG. 26. The toothbrush bristle restoration body top wall 812 is rotated into a closed position, securing the toothbrush assembly 400 within the interior of the toothbrush bristle restoration apparatus 800. Sanitizing fumes emitted from the bottom wall supported sanitizing pad 852 and the contact pad supported sanitizing pad 854 sanitize the toothbrush assembly 400.

Although the illustrated embodiment of the toothbrush bristle restoration apparatus 800 affixes each toothbrush bristle restoration pad 830 to the toothbrush bristle restoration body side wall 814 in a rigid manner, the pivoting assembly as taught above can be integrated into the toothbrush bristle restoration apparatus 800. This can be applied to any of the variants including those introduced below.

Figure 27:
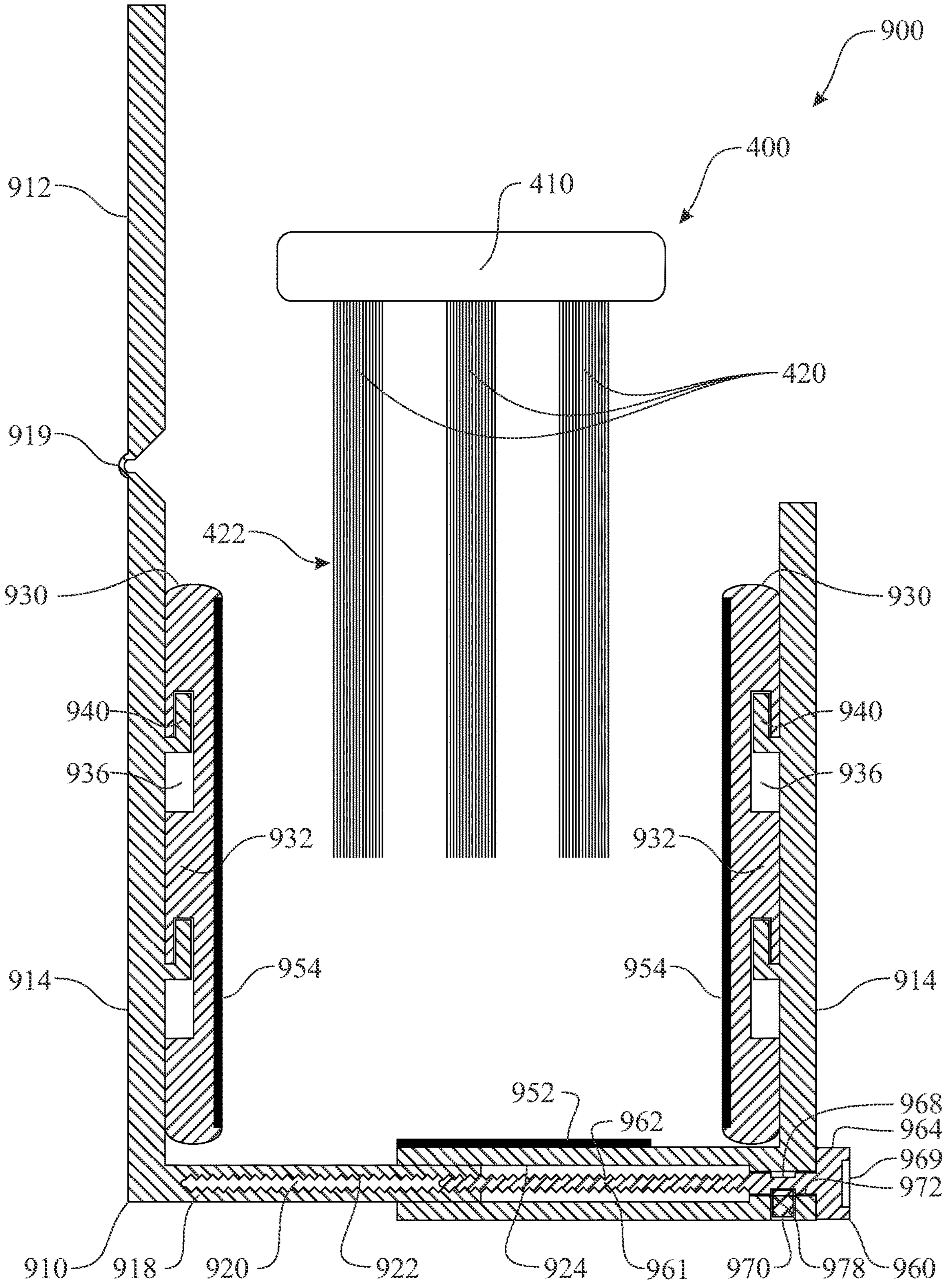
FIG. 27 presents a sectioned end view of a fifth exemplary toothbrush bristle restoration apparatus, the fifth exemplary toothbrush bristle restoration apparatus employing a threadably adjustable bottom wall, the illustration presenting the base in a widened state wherein the pair of restoration pads are positioned in a toothbrush insertion orientation staged for insertion of the toothbrush.
Figure 28:
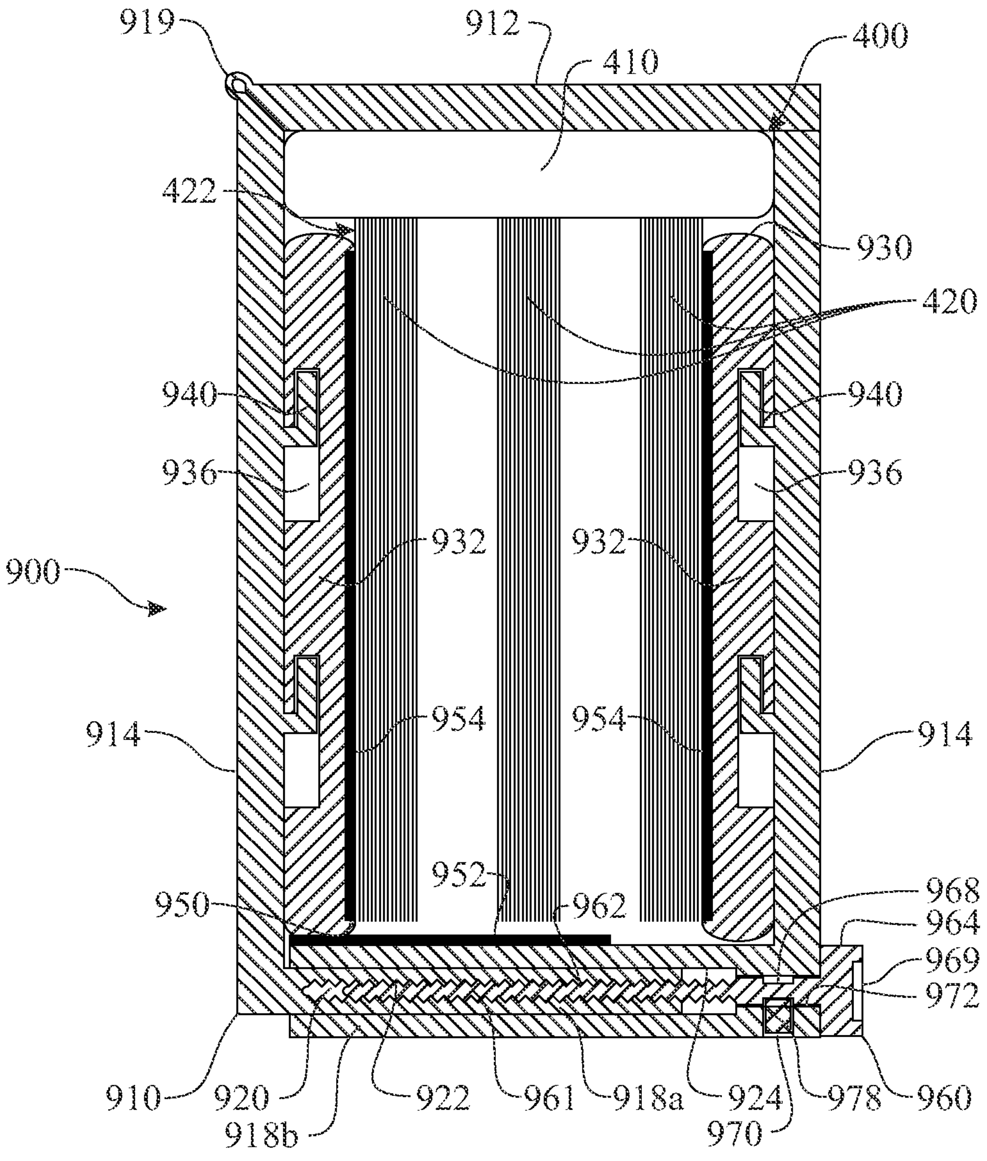
FIG. 28 presents a sectioned end view of the fifth exemplary toothbrush bristle restoration apparatus originally introduced in FIG. 27, the illustration presenting the base in a contracted state wherein the pair of restoration pads are positioned in a bristle restoration orientation applying a restoration source to sets of bristles of the toothbrush.

In another example, the pair of toothbrush bristle restoration pads 130 can be separated and drawn together using a threaded element 960, as introduced in a toothbrush bristle restoration apparatus 900 illustrated in FIGS. 27 and 28. The toothbrush bristle restoration apparatus 900, exemplifying this arrangement, is very similar to the toothbrush bristle restoration apparatus 800, where the threaded element 960 replaces the ratcheting interface 822, 823. Like elements of the toothbrush bristle restoration apparatus 900 and the toothbrush bristle restoration apparatus 800 are numbered the same, wherein elements of the toothbrush bristle restoration apparatus 900 are preceded by the numeral "9".

A bottom wall of the toothbrush bristle restoration body 910 is formed in two pieces: (a) a toothbrush bristle restoration body bottom wall first sliding section 918*a* comprising a width adjustment tongue receiving groove 920 having a width adjustment tongue receiving groove teeth 922 formed in the surface and (b) a toothbrush bristle restoration body bottom wall second sliding section 918*b* comprising a width adjustment bore 924. The width adjustment bore 924 is sized to slideably engage with an exterior surface of the toothbrush bristle restoration body bottom wall first sliding section 918*a*. The sliding arrangement between the toothbrush bristle restoration body bottom wall first sliding section 918*a* and the toothbrush bristle restoration body bottom wall second sliding section 918*b* ensures a parallel movement between the pair of toothbrush bristle restoration body side walls 914. Movement between the toothbrush bristle restoration body bottom wall first sliding section 918*a* and the toothbrush bristle restoration body bottom wall second sliding section 918*b* is controlled by the width adjustment threaded member 960. The width adjustment threaded member 960 includes a threaded shaft 961 extending concentrically and axially from a threaded member head 964. Threading 962 is formed on a surface of the threaded shaft 961. A threaded member rotation tool engaging formation 969 can be formed in the threaded member head 964. The threaded member rotation tool engaging formation 969 can be designed to receive a slotted screwdriver, a Philips head screwdriver, a hex drive tool, a star bit tool, a square drive tool, a socket drive tool, or any other tool. Alternatively, the threaded member rotation tool engaging formation 969 can be a knurling, wings, or any other feature that would assist a person in gripping and rotating the width adjustment threaded member 960.

The width adjustment threaded member 960 is inserted through a smooth bore 972 formed in the toothbrush bristle restoration body bottom wall second sliding section 918*b*. The width adjustment threaded member 960 can be retained in position respective to the toothbrush bristle restoration body bottom wall second sliding section 918*b* by a threaded member retention component 978. The threaded member retention component 978 is inserted through a threaded member retention component clearance 970 and engages with a threaded member retention groove 968 formed in a portion of the threaded shaft 961 of the width adjustment threaded member 960. In an alternative arrangement, the threaded member retention component 978 can be a threaded element that is threadably assembled in the threaded member retention component clearance 970.

The threading 962 engages with the width adjustment tongue receiving groove teeth 922 formed within the width adjustment tongue receiving groove 920. As the width adjustment threaded member 960 is rotated, engagement between the threading 962 and the width adjustment tongue receiving groove teeth 922 moves the toothbrush bristle restoration body bottom wall first sliding section 918*a* towards or away from the toothbrush bristle restoration body bottom wall second sliding section 918*b*, depending upon the direction of a rotational force applied to the threaded member head 964. As the width adjustment threaded member 960 is rotated, the toothbrush bristle restoration body bottom wall first sliding section 918*a* slides within the width adjustment bore 924 of the toothbrush bristle restoration body bottom wall second sliding section 918*b*. The width adjustment threaded member 960 would be rotated in a first direction to expand a distance between facing surfaces of the pair of toothbrush bristle restoration pad bodies 932 to enable insertion of the toothbrush bristles 420 of the toothbrush assembly 400, as illustrated in FIG. 27. The toothbrush bristles 420 of the toothbrush assembly 400 would then be inserted between the pair of toothbrush bristle restoration pad bodies 932. The width adjustment threaded member 960 would be rotated in a second, opposite direction, drawing the pair of toothbrush bristle restoration pad bodies 932 towards one another until the pair of toothbrush bristle restoration pad bodies 932 applies a restoration force to the toothbrush bristles outer surface 422 of the toothbrush bristles 420, as illustrated in FIG. 28. While the width adjustment threaded member 960 is rotated, the threaded member retention component 978 retains the width adjustment threaded member 960 in position within the toothbrush bristle restoration body bottom wall second sliding section 918*b*.

In another example, the toothbrush bristle restoration apparatus 700 can be modified by replacing the pivotal motion of the toothbrush bristle restoration pads 730 with at least one slideable toothbrush bristle restoration pad 730. A toothbrush bristle restoration apparatus 1000, illustrated in FIGS. 29 and 30, integrates this concept. The toothbrush bristle restoration apparatus 1000 includes a number of elements that are common with the toothbrush bristle restoration apparatus 800, while including a toothbrush bristle restoration body bottom wall 918*a*, 918*b* having a fixed dimension. Like elements of the toothbrush bristle restoration apparatus 1000 and the toothbrush bristle restoration apparatus 800 are numbered the same, wherein elements of the toothbrush bristle restoration apparatus 1000 are preceded by the numeral "10".

A toothbrush bristle restoration pad 1030, having a toothbrush bristle restoration pad body 1032, is assembled to one toothbrush bristle restoration body side wall 1014 of the toothbrush bristle restoration body 1010. A toothbrush bristle positionable restoration pad 1031, having a toothbrush bristle restoration pad body 1033, is moveably assembled to a second, opposite toothbrush bristle restoration body side wall 1014 of the toothbrush bristle restoration body 1010. The toothbrush bristle restoration pad body 1033 has a contacting surface that mirrors a contacting surface of the toothbrush bristle restoration pad body 1032, while the toothbrush bristle restoration pad body 1033 is designed to be adjustably positioned by a width adjustment threaded member 1060. The width adjustment threaded member 1060 includes a threaded shaft 1061 extending concentrically and axially from a threaded member head 1064. Threading 1062 is formed on a surface of the threaded shaft 1061. A threaded member rotation tool engaging formation 1069 can be formed in the threaded member head 1064. The threaded member rotation tool engaging formation 1069 and the threaded member rotation tool engaging formation 969 are similarly described. A threaded member bulbous end 1067 is formed at a distal, free end of the threaded shaft 961. The threaded member bulbous end 1067 engages with a toothbrush bristle restoration pad body adjusting member receiving feature 1037 formed in a rear portion of the toothbrush bristle restoration pad body 1033. The threaded shaft 1061 is threadably inserted into a threaded bore 1072 formed through the toothbrush bristle restoration body side wall 1014. The threaded member bulbous end 1067 snaps into the toothbrush bristle restoration pad body adjusting member receiving feature 1037.

Figure 29:
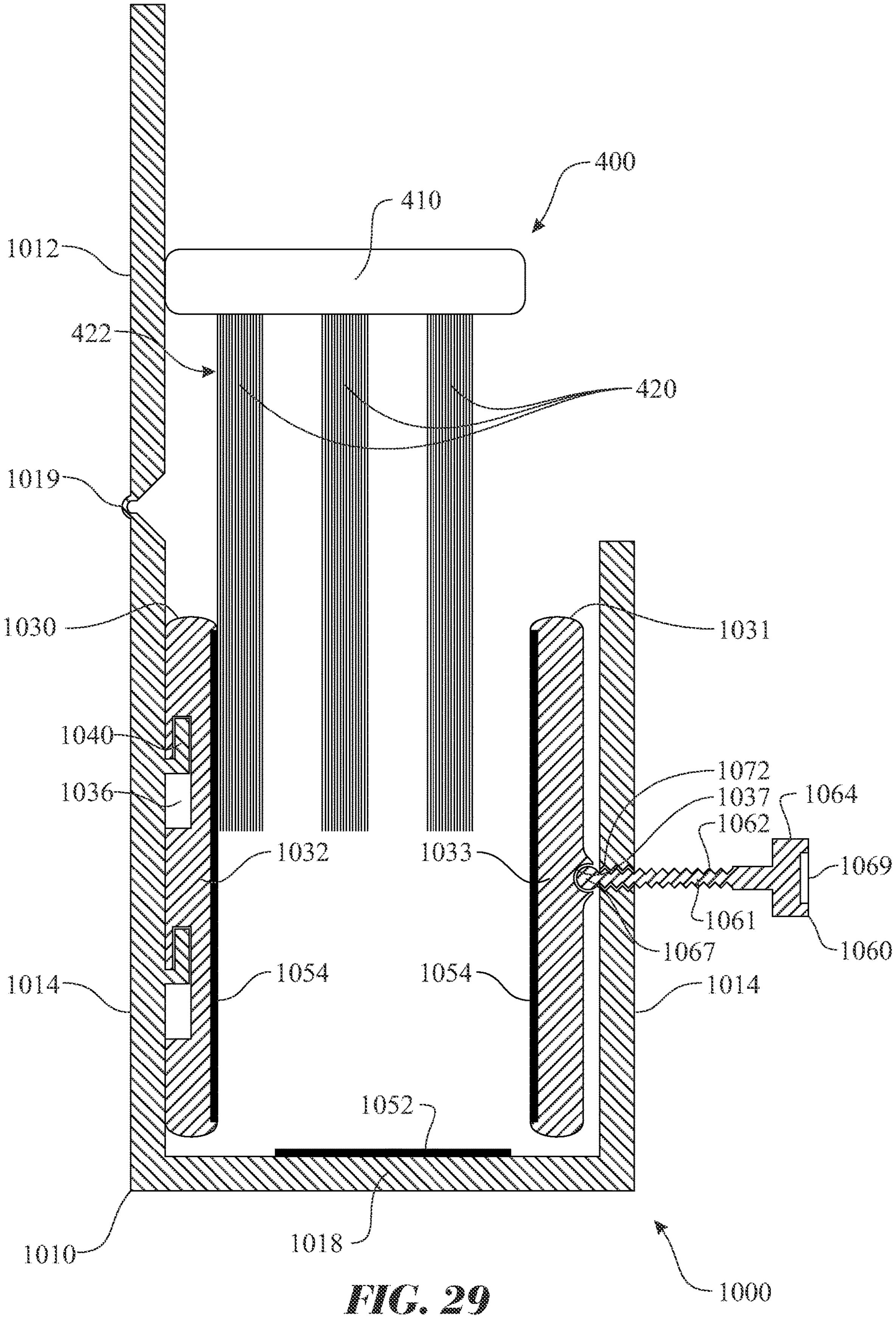
FIG. 29 presents a sectioned end view of a sixth exemplary toothbrush bristle restoration apparatus, the sixth exemplary toothbrush bristle restoration apparatus employing a threadably positionable restoration pad, the illustration presenting the threadably positionable restoration pad in a widened state wherein the pair of restoration pads are positioned in a toothbrush insertion orientation staged for insertion of the toothbrush.
Figure 30:
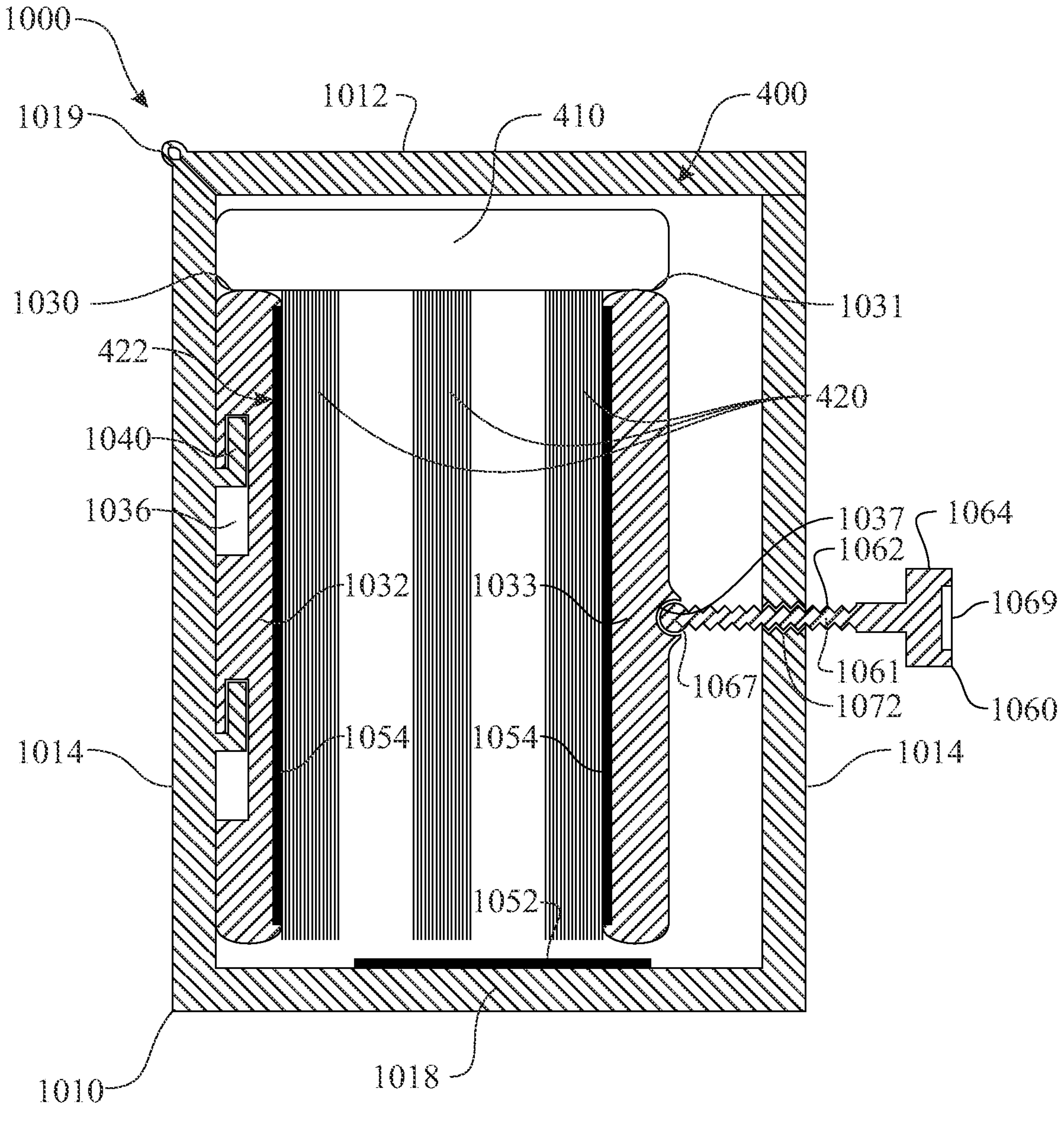
FIG. 30 presents a sectioned end view of the sixth exemplary toothbrush bristle restoration apparatus originally introduced in FIG. 29, the illustration presenting the threadably positionable restoration pad in a contracted state wherein the pair of restoration pads are positioned in a bristle restoration orientation applying a restoration source to sets of bristles of the toothbrush.

As the width adjustment threaded member 1060 is rotated, engagement between the threading 1062 and the threaded bore 1072 moves the toothbrush bristle restoration pad body 1033 towards or away from the toothbrush bristle restoration pad body 1032, depending upon the direction of a rotational force applied to the threaded member head 1064. As the width adjustment threaded member 1060 is rotated, the threaded member bulbous end 1067 drives the toothbrush bristle restoration pad body 1033 towards or away from the toothbrush bristle restoration pad body 1032. The width adjustment threaded member 1060 would be rotated in a first direction to expand a distance between facing surfaces of the toothbrush bristle restoration pad body 1032 and the toothbrush bristle restoration pad body 1033 to enable insertion of the toothbrush bristles 420 of the toothbrush assembly 400, as illustrated in FIG. 29. The toothbrush bristles 420 of the toothbrush assembly 400 would then be inserted between the toothbrush bristle restoration pad body 1032 and the toothbrush bristle restoration pad body 1033. The width adjustment threaded member 1060 would be rotated in a second, opposite direction, drawing the toothbrush bristle restoration pad body 1032 and the toothbrush bristle restoration pad body 1033 towards one another until the toothbrush bristle restoration pad body 1032 and the toothbrush bristle restoration pad body 1033 apply a restoration force to the toothbrush bristles outer surface 422 of the toothbrush bristles 420, as illustrated in FIG. 30. Although the exemplary toothbrush bristle restoration apparatus 1000 includes a single width adjustment threaded member 1060, the toothbrush bristle restoration apparatus 1000 can be modified to include a width adjustment threaded member 1060 on each toothbrush bristle restoration body side wall 1014. Additional features can be incorporated into the toothbrush bristle restoration apparatus 1000 to aid in controlling a sliding motion of the toothbrush bristle restoration pad body 1033.

In another example, the toothbrush bristle restoration apparatus 1000 can be modified by replacing the width adjustment threaded member 1060 with a width adjustment retention member 1160 operated by a biasing element 1162. A toothbrush bristle restoration apparatus 1100, illustrated in FIGS. 31 and 32, integrates this concept. The toothbrush bristle restoration apparatus 1100 includes a number of elements that are common with the toothbrush bristle restoration apparatus 1000, while replacing the width adjustment threaded member 1060 with a width adjustment retention member 1160 operated by a biasing element 1162. Like elements of the toothbrush bristle restoration apparatus 1100 and the toothbrush bristle restoration apparatus 1000 are numbered the same, wherein elements of the toothbrush bristle restoration apparatus 1100 are preceded by the numeral “11”.

A smooth shaft 1161 of the width adjustment retention member 1160 is slideably inserted through a smooth bore 1172 formed through a toothbrush bristle restoration body side wall 1114. The width adjustment retention member 1160 is threadably assembled to a toothbrush bristle restoration pad body 1133 by threading a threaded assembly end 1169 into a like threaded bore formed in the toothbrush bristle restoration pad body 1133. The biasing element 1162 is assembled between facing surfaces of the toothbrush bristle restoration pad body 1133 and the toothbrush bristle restoration body side wall 1114. The exemplary biasing element 1162 is a compression coil spring. The smooth shaft 1161 is slideably inserted through a center of the biasing element 1162, as illustrated. A width adjustment retention member head 1164 is formed on an end of the smooth bore 1172, wherein the width adjustment retention member head 1164 provides a grip for the user.

Figure 31:
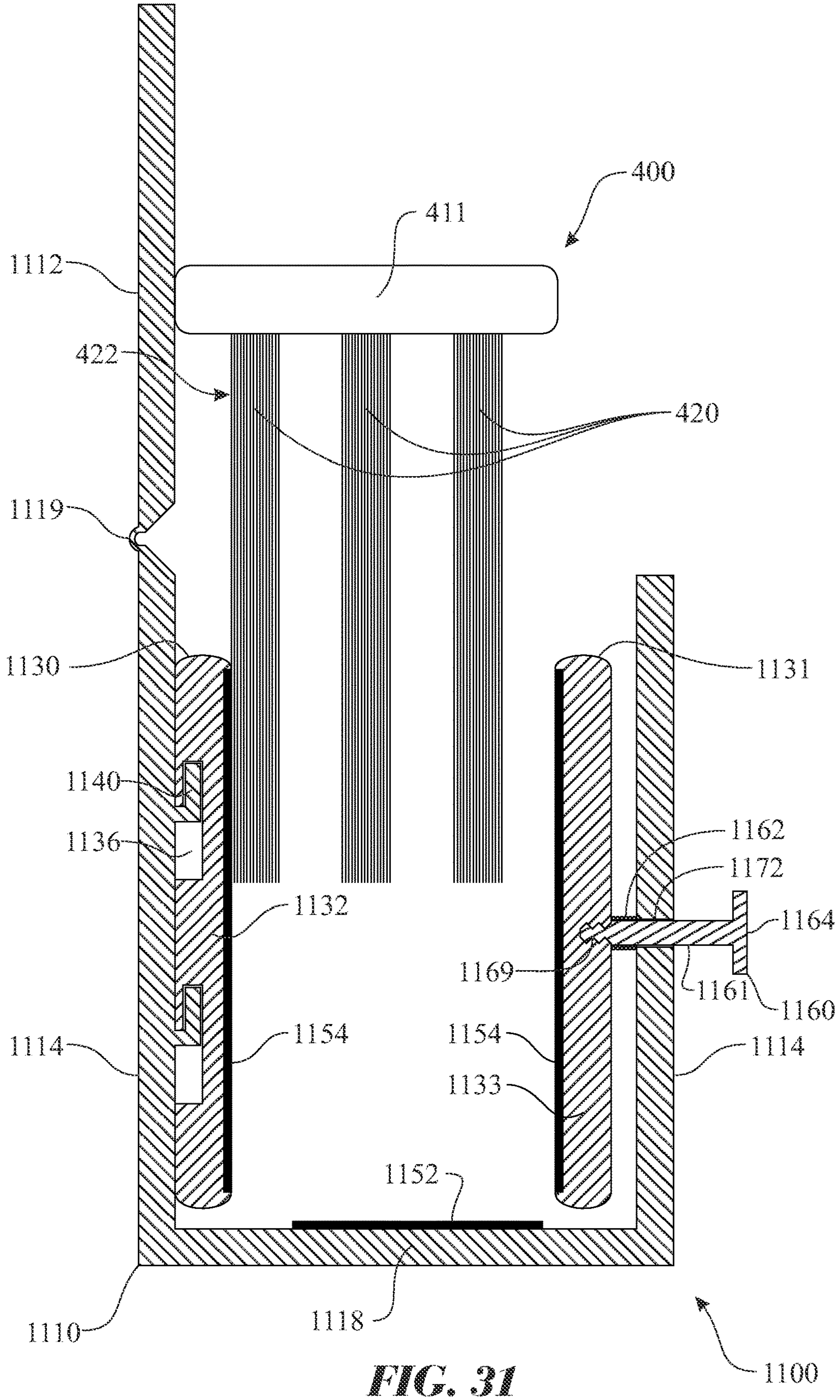
FIG. 31 presents a sectioned end view of a seventh exemplary toothbrush bristle restoration apparatus, the seventh exemplary toothbrush bristle restoration apparatus employing a positionable restoration pad controlled by a biasing element, the illustration presenting the positionable restoration pad in a widened state wherein the pair of restoration pads are positioned in a toothbrush insertion orientation staged for insertion of the toothbrush.
Figure 32:
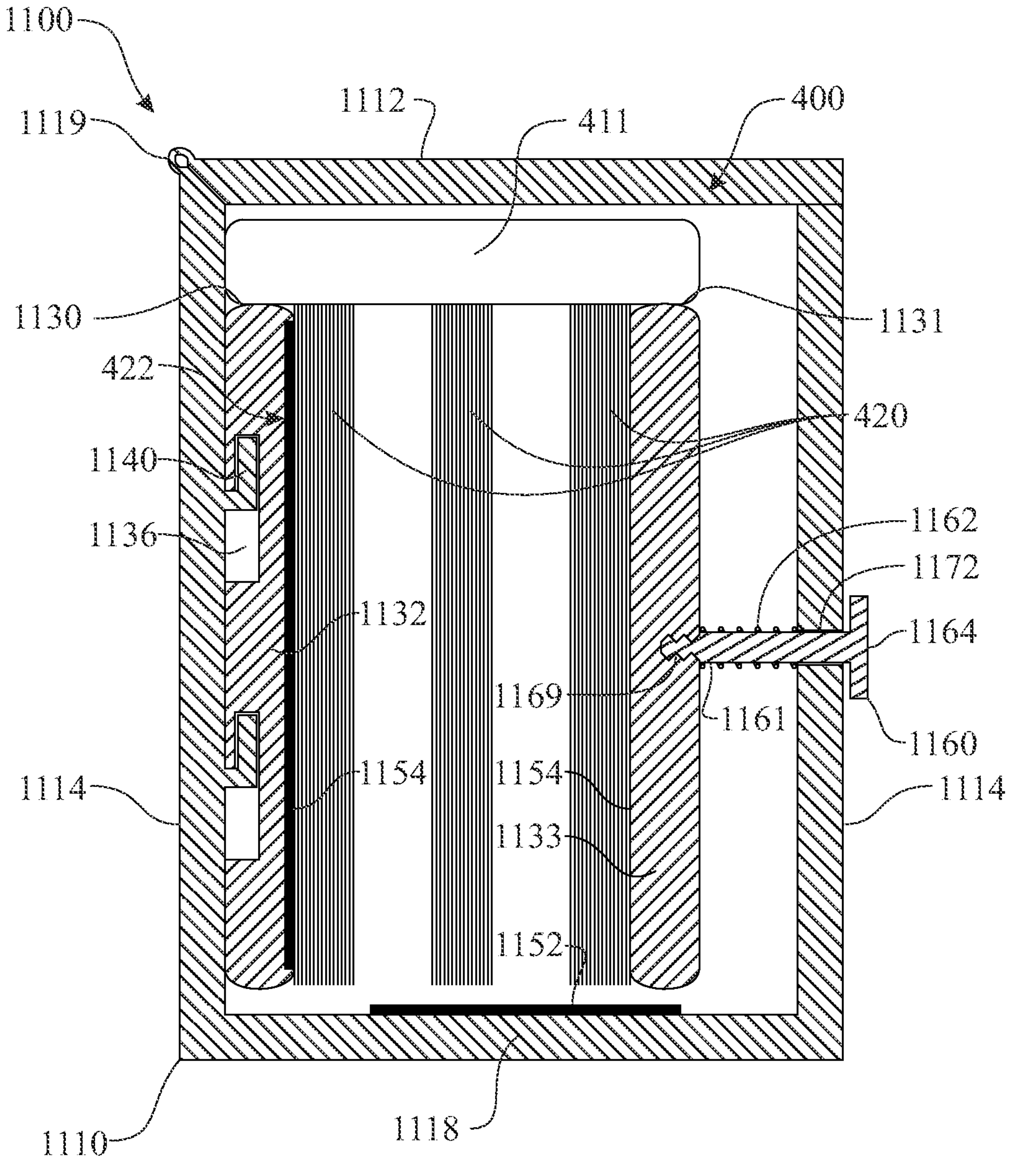
FIG. 32 presents a sectioned end view of the seventh exemplary toothbrush bristle restoration apparatus originally introduced in FIG. 30, the illustration presenting the positionable restoration pad in a contracted state wherein the pair of restoration pads is positioned in a bristle restoration orientation applying a restoration source to sets of bristles of the toothbrush.

In use, the operator can draw the toothbrush bristle restoration pad body 1133 away from the toothbrush bristle restoration pad body 1132 by applying a pressure to a contacting surface of the toothbrush bristle restoration pad body 1133 or by applying a pulling force to the width adjustment retention member head 1164, placing the toothbrush bristle restoration apparatus 1100 in an open condition, as illustrated in FIG. 31. The operator would insert the toothbrush bristles 420 between the toothbrush bristle restoration pad body 1132 and the toothbrush bristle restoration pad body 1133, then release the tension applied to the biasing element 1162. By releasing the tension applied to the biasing element 1162, the biasing element 1162 applies a restoration force to the toothbrush bristles 420 placing the toothbrush bristle restoration apparatus 1100 in a restoration condition, as illustrated in FIG. 32. In the restoration condition, the biasing element 1162 applies a compression force between the toothbrush bristle restoration pad body 1132 and the toothbrush bristle restoration pad body 1133.

Although the various toothbrush bristle restoration apparatuses 600, 700, 1000, 1100, employ a lid for retention of the toothbrush assembly 400 within an interior of the respective toothbrush bristle restoration apparatuses 600, 700, 1000, 1100, the toothbrush assembly 400 can be retained within the interior of the toothbrush bristle restoration apparatuses 600, 700, 1000, 1100 using a snap design, such as the snap designs described in FIGS. 1 through 11 of U.S. Pat. No. 5,048,144. The sidewalls can be shaped to follow a contour of a design of any target toothbrush 400. In another alternative, the toothbrush bristle restoration apparatuses 600, 700, 1000, 1100 can include a sliding retention feature, enabling the head of the toothbrush assembly 400 to be slideably inserted into the toothbrush bristle restoration apparatuses 600, 700, 1000, 1100. The sliding interface would be applicable for toothbrush designs suitable for such an assembly. One example is presented in US pre-grant publication number 2008/0060829. When using the sliding design, the light pipes 324 would be arranged to be parallel to a direction of insertion of the head of the toothbrush assembly 400.

In yet another example, the pair of toothbrush bristle restoration pads 130 can be operated by an arrangement of gears, where the arrangement of gears would toggle the pair of toothbrush bristle restoration pads 130 between an expanded configuration and a compression configuration.

In yet another example, the pair of toothbrush bristle restoration pads 130 can be operated by a contraction member, where the contraction member would toggle the pair of toothbrush bristle restoration pads 130 between an expanded configuration and a compression configuration. In the exemplary illustration, the toothbrush bristle restoration body 110 is designed to remain in a naturally closed configuration when free of any external forces. In this example, the toothbrush bristle restoration body 110 would be shaped having a naturally expanded configuration when free of any external forces. The contraction member would apply a closure force to the toothbrush bristle restoration body 110 when positioned accordingly. The toothbrush bristle restoration body sidewall portion 114 would be arranged having an obtuse angle respective to the toothbrush bristle restoration body top portion 112. When the contraction member is pushed downward, towards the distal, free end of the toothbrush bristle restoration body sidewall portions 114, the contraction member drives the distal, free ends of the toothbrush bristle restoration body sidewall portions 114 towards one another.

In yet another example, the toothbrush bristle restoration body 110 can be formed as two components hingeably assembled to one another, the toothbrush bristle restoration body 110 further comprising a biasing element (such as a spring) to maintain the distal, free ends of the two components in a closed configuration. A grip would be provided at the opposite end of each of the two components, where the grip is provided for the user. This can be similar to a clothespin or hairclip design.

Figure 33:
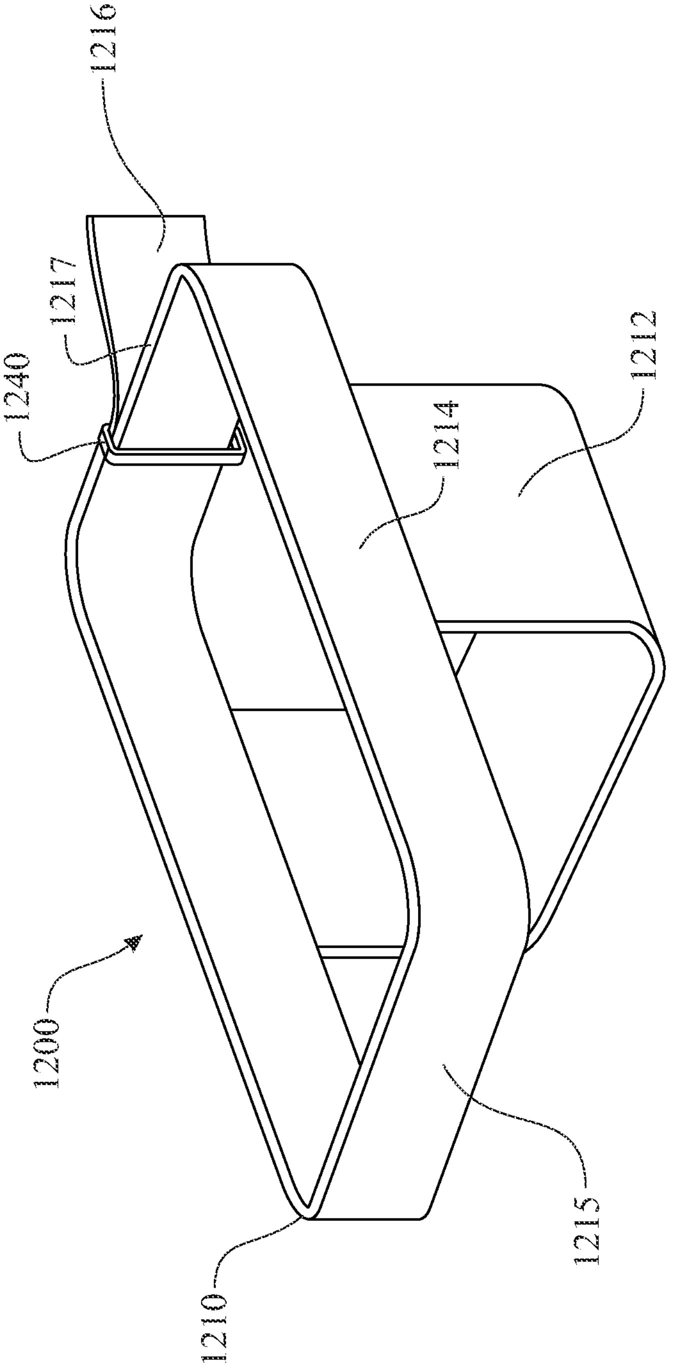
FIG. 33 presents an isometric front side view of an eighth exemplary toothbrush bristle restoration apparatus, the eighth exemplary toothbrush bristle restoration apparatus employing a flexible member that conforms to a shape of exterior surfaces of sets of bristles.
Figure 34:
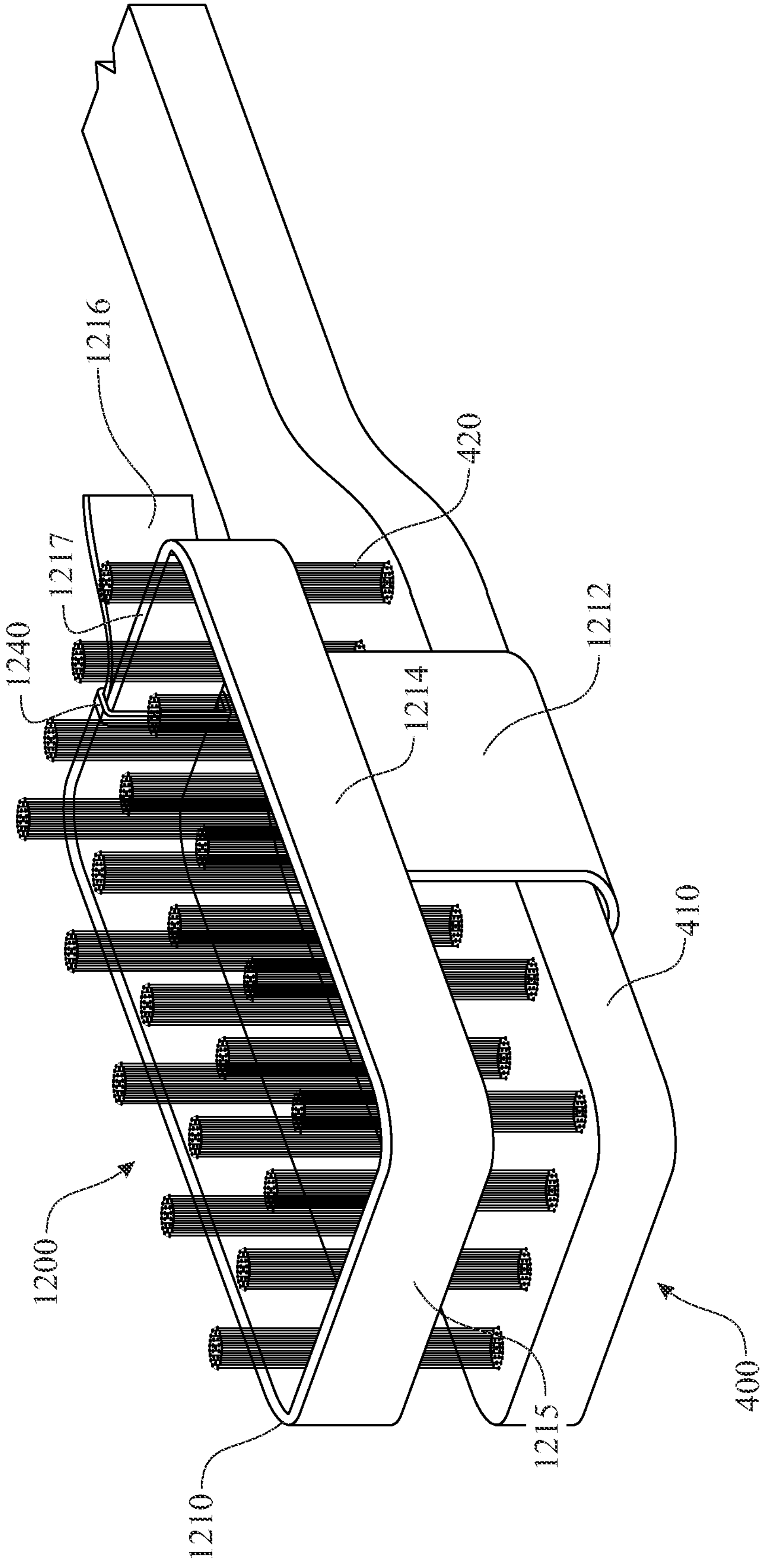
FIG. 34 presents an isometric front side view of the eighth exemplary toothbrush bristle restoration apparatus originally introduced in FIG. 33, the illustration presenting the eighth exemplary toothbrush bristle restoration apparatus installed upon a toothbrush.
Figure 35:
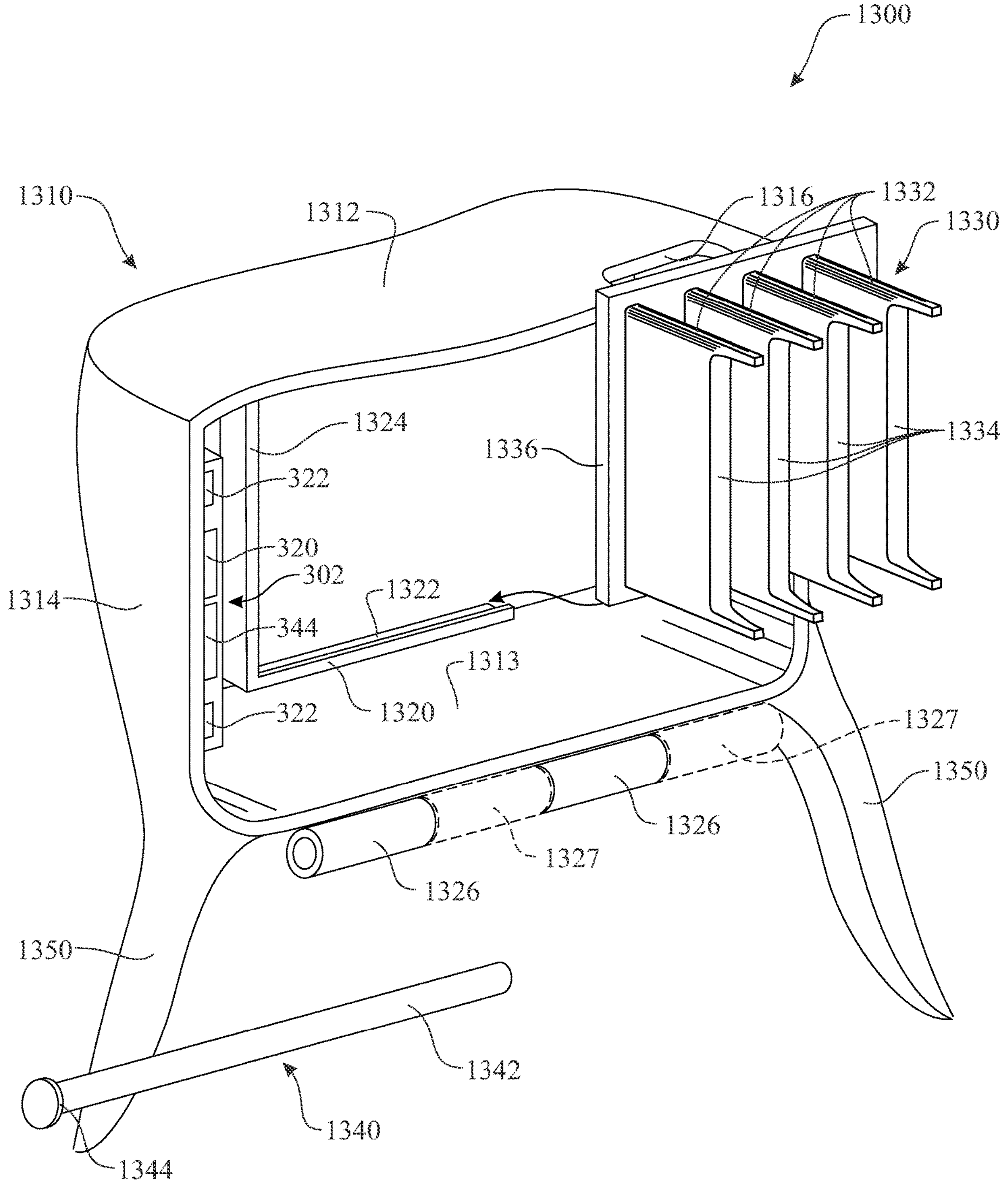
FIG. 35 presents a isometric front side partially exploded assembly view of one side of a ninth exemplary toothbrush bristle restoration apparatus, the ninth exemplary toothbrush bristle restoration apparatus employing a series of flexible bristle restoration members that conform to a shape of exterior surfaces of sets of bristles, an exemplary housing of the toothbrush bristle restoration apparatus being provided in a shape of a tooth, the illustration presenting a portion of the elements prior to assembly.
Figure 36:
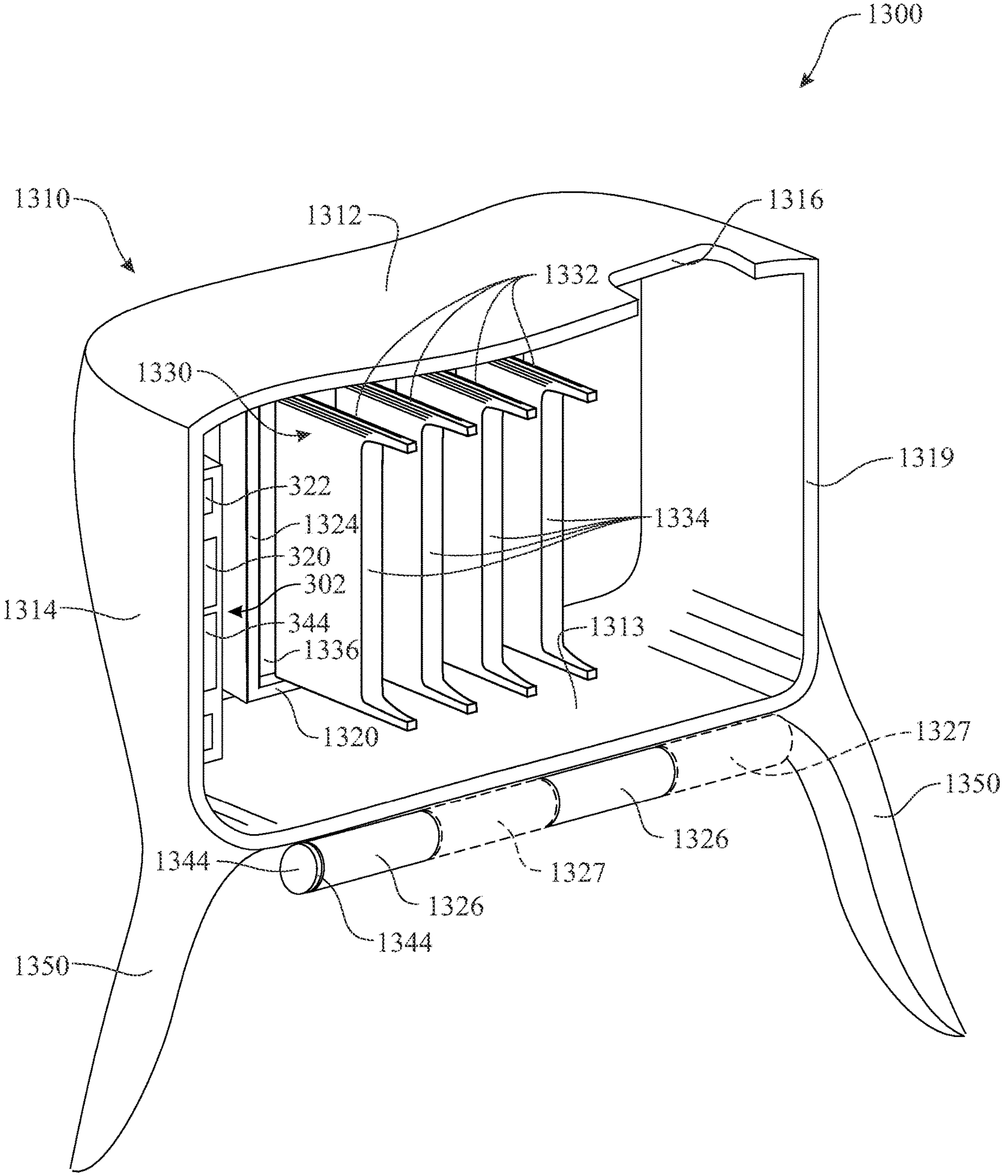
FIG. 36 presents an isometric front side assembled view of one side of the ninth exemplary toothbrush bristle restoration apparatus originally introduced in FIG. 35, the illustration presenting the ninth exemplary toothbrush bristle restoration apparatus installed upon a toothbrush, the illustration presenting elements assembled thereto.
Figure 37:
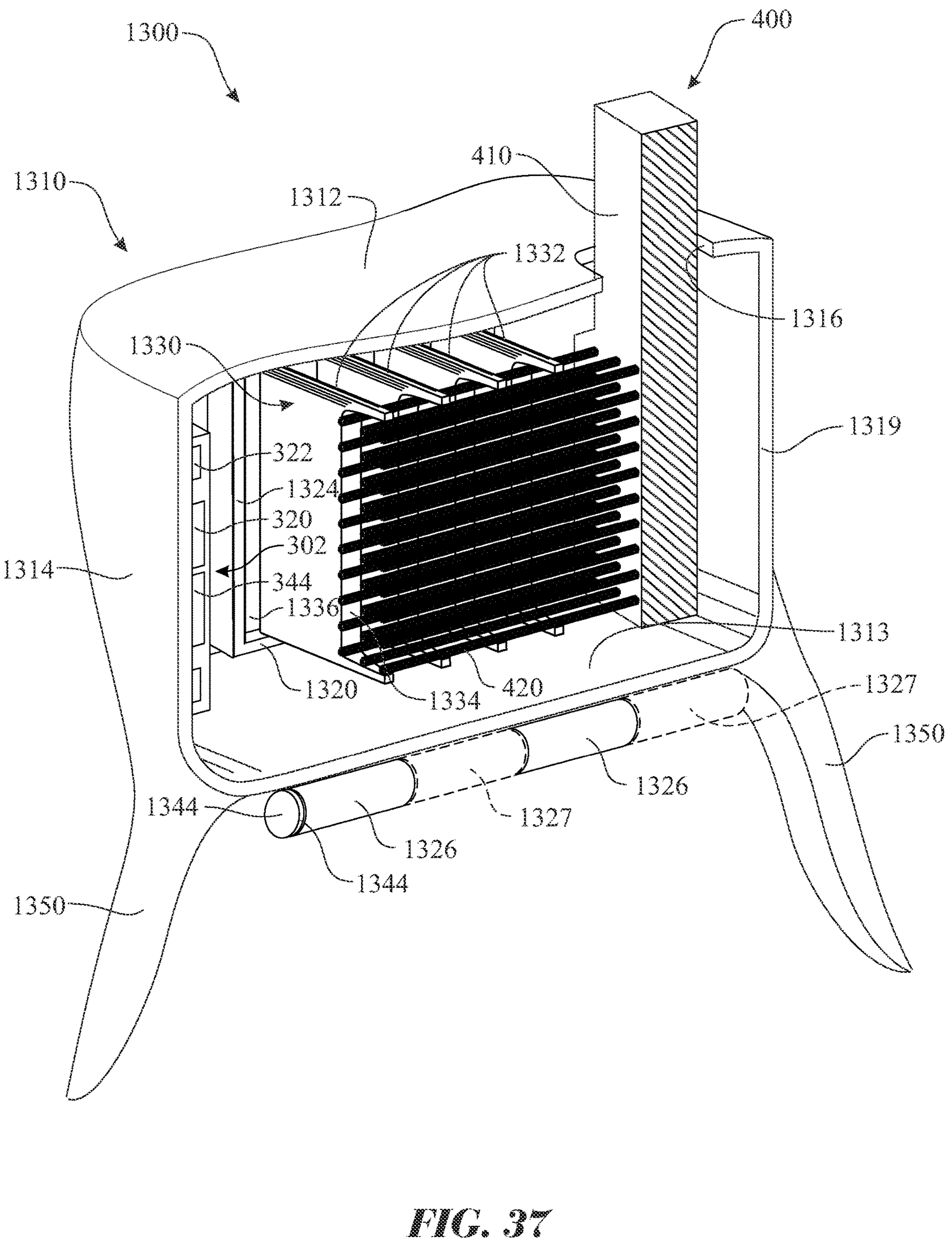
FIG. 37 presents an isometric front side assembled view of one side of the ninth exemplary toothbrush bristle restoration apparatus originally introduced in FIG. 35, the illustration presenting the toothbrush seated within the ninth exemplary toothbrush bristle restoration apparatus.

Each of the above describes an apparatus having dedicated restoration pads. The same function can be accomplished using a toothbrush bristle restoration apparatus 1200, introduced in FIG. 33. The primary elements of any bristle restoration and maintenance apparatus are:

1) An application of a restoration force to the exterior surfaces of bristles of the toothbrush, and
2) A retention member, wherein the retention member is designed to maintain the bristle restoration and maintenance apparatus on the toothbrush.

When a restoration force is applied to the bristles 420, the bristles 420 tend to bend inward. This places the bristles 420 into a tapered shape, which drives the bristle restoration and maintenance apparatus towards distal, free ends of the bristles 420. The retention member provides a retention force, keeping the bristle restoration and maintenance apparatus at a constant position on the bristles 420 of the toothbrush 400. In the illustration toothbrush bristle restoration apparatus 1200, a toothbrush bristle restoration body 1210 provides the restoration force and the toothbrush bristle restoration body toothbrush retention member 1212 provides the retention force.

The exemplary toothbrush bristle restoration body 1210 is a flexible strap, when installed, defines a pair of toothbrush bristle restoration body side walls 1214, a toothbrush bristle restoration body front wall 1215, and a toothbrush bristle restoration body rear wall 1217. A restoration force applying component 1230 is secured to one end of the toothbrush bristle restoration body 1210. A toothbrush bristle restoration body adjusting tail 1216 is provided at a second, opposite end of the toothbrush bristle restoration body 1210. The toothbrush bristle restoration body adjusting tail 1216 is either removed from the restoration force applying component 1230 or positioned (pulled rearward through the restoration force applying component 1230) such to open an interior of the toothbrush bristle restoration body 1210. The toothbrush assembly 400 is inserted between the toothbrush bristle restoration body 1210 and an interior surface of the toothbrush bristle restoration body toothbrush retention member 1212, locating the bristles 420 of the toothbrush 400 within the interior defined by the toothbrush bristle restoration body 1210. Once the toothbrush bristle restoration apparatus 1200 is properly positioned in the toothbrush assembly 400, the toothbrush bristle restoration body adjusting tail 1216 is positioned and secured via the restoration force applying component 1230 in a manner to cause the toothbrush bristle restoration body 1210 to apply an adequate restoration force to the bristles 420. The toothbrush bristle restoration body toothbrush retention member 1212 retains the toothbrush bristle restoration body 1210 in proper position on the bristles 420.

The restoration force applying component 1230 can be replaced with any suitable arrangement that is capable of adjusting and retaining a length of a strap. For example, any buckle design can be utilized. In another example, mating sections of a dense hook and loop tape can be applied to each of the first end and the second end of the toothbrush bristle restoration body 1210. In yet another example, a toothed clamp can be utilized to retain the length of the strap. The form factor selected for adjusting and retaining the length of the toothbrush bristle restoration body 1210 is not considered limiting to the apparatus, where any suitable form factor can be implemented.

The interior or contacting surface of the toothbrush bristle restoration body 1210 can include one or more features to aid in gripping the bristles 420. For example, the interior surface can be textured, such as roughing the surface, including bumps, including projections, or any other grip enhancing feature. A different material can be applied to the interior surface of the toothbrush bristle restoration body 1210 wherein the different material would have a higher coefficient of friction compared to the material of the exterior of the toothbrush bristle restoration body 1210.

The toothbrush bristle restoration apparatus 100 is a first apparatus for maintenance of the toothbrush assembly 400. A toothbrush sanitizing assembly 300, presented in FIGS. 11 through 15, is a second apparatus for maintenance of the toothbrush assembly 400. The toothbrush sanitizing assembly 300 provides a function to sanitize the toothbrush assembly 400, more specifically, the toothbrush bristles 420 of the toothbrush assembly 400. The toothbrush sanitizing assembly 300 includes a toothbrush sanitizing assembly body 310. In the exemplary illustration, the toothbrush sanitizing assembly body 310 includes a pair of toothbrush sanitizing assembly body end panels 314, each toothbrush sanitizing assembly body end panel 314 extending generally perpendicularly from a respective edge of a toothbrush sanitizing assembly body top panel 312. The toothbrush sanitizing assembly body 310 can be any suitable design based upon the determined application. The exemplary toothbrush sanitizing assembly body 310 presented in the illustrations is designed to be used in conjunction with a toothbrush bristle restoration apparatus 200 (wherein the toothbrush bristle restoration apparatus 200 is a modified version of the toothbrush bristle restoration apparatus 100). The exemplary toothbrush sanitizing assembly body 310 can be modified to be used independently. For example, the toothbrush sanitizing assembly body 310 can include a pair of sidewalls comprising an attachment groove, such as the toothbrush bristle restoration body toothbrush gripping formations 116 of the toothbrush bristle restoration apparatus 100 for attachment to the toothbrush assembly 400. In another example, the toothbrush sanitizing assembly body 310 can include at least three (3) sidewalls extending downward from a top panel. A pair of grooves would be formed in two opposing sidewalls, wherein the grooves are designed to slide onto the edges of the toothbrush body 410 of the toothbrush assembly 400. In yet another example, the toothbrush sanitizing assembly body 310 can be a complete enclosure comprising a top panel and four (4) sidewalls forming a container and a bottom panel hingeably connected to an edge of one of the four (4) sidewalls. The toothbrush bristles 420 would be inserted into the container and the bottom panel would be pivoted closed and secured accordingly.

Figure 15:
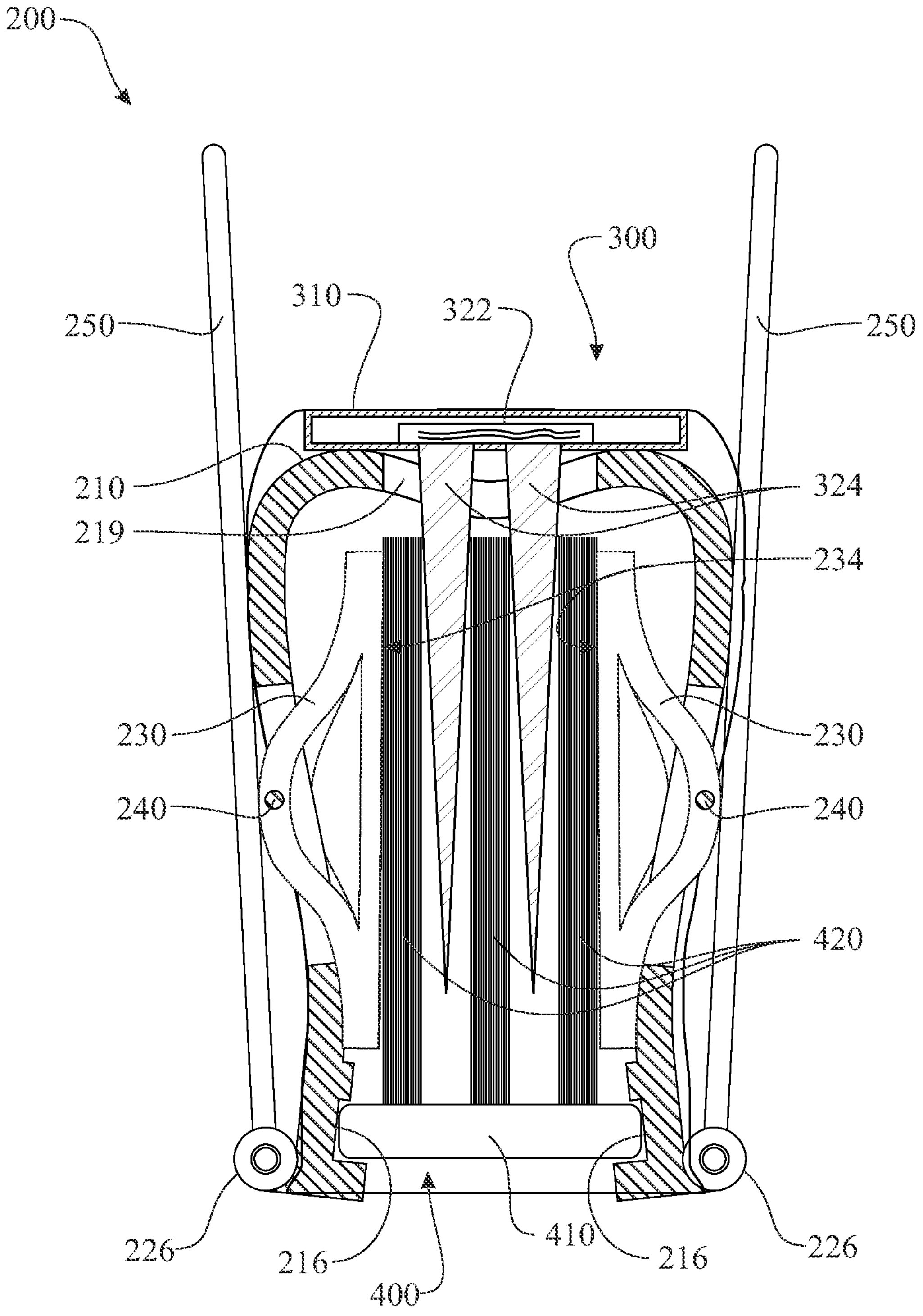
FIG. 15 presents sectioned end view of the exemplary toothbrush sanitizing assembly originally introduced in FIG. 11 and the modified exemplary version of the toothbrush bristle restoration apparatus originally introduced in FIG. 11 being assembled to one another.

At least one toothbrush sanitizing assembly sanitizing light source 322 is integrated into the toothbrush sanitizing assembly body 310 at any suitable location thereof. A toothbrush sanitizing assembly portable power supply 320 is carried by the toothbrush sanitizing assembly body 310 and provided in electrical communication with the at least one toothbrush sanitizing assembly sanitizing light source 322, enabling operation of the at least one toothbrush sanitizing assembly sanitizing light source 322. An operating switch (not shown) can be integrated into a circuit between the toothbrush sanitizing assembly portable power supply 320 and the at least one toothbrush sanitizing assembly sanitizing light source 322 to manage operation and power consumption. A battery retention system can be integrated into the toothbrush sanitizing assembly body 310 enabling replacement of the battery when the electrical charge is depleted. Alternatively or additionally, a charging circuit can be integrated into the toothbrush sanitizing assembly body 310 enabling recharging of the toothbrush sanitizing assembly portable power supply 320. The toothbrush sanitizing assembly sanitizing light source 322 are oriented to direct an emission of sanitizing light towards an inlet surface of at least one toothbrush sanitizing assembly sanitizing light pipe 324. Each of the at least one toothbrush sanitizing assembly sanitizing light pipe 324 is shaped to be inserted between rows of sets of toothbrush bristles 420 of the toothbrush assembly 400, as shown in FIG. 15. The toothbrush sanitizing assembly sanitizing light pipe 324 can be of any suitable size and shape, including a wedge shape (as shown), cylindrically shaped, conically shaped, rectangularly shaped, pyramid in shape, frustum shaped, and the like. In a design including two or more toothbrush sanitizing assembly sanitizing light pipes 324, the two or more toothbrush sanitizing assembly sanitizing light pipes 324 can be formed as a single component having a single light entry point or multiple light entry points.

At least one of the toothbrush bristle restoration body 110 and the toothbrush sanitizing assembly body 310 can be transparent or translucent, enabling passage of light from the light emitting elements 322.

The toothbrush sanitizing assembly body end panel 314 can be sized and shaped to contact bristles 420 at each end of the head of the toothbrush assembly 400. Although the illustrated toothbrush sanitizing assembly body 310 places the toothbrush sanitizing assembly body end panels 314 in a fixed span, the toothbrush sanitizing assembly body 310 can include features enabling an adjustable span between toothbrush sanitizing assembly body end panels 314 to accommodate toothbrushes 400 of different sizes. Alternatively, pads or other spacers of different sizes can be inserted between an interior surface of each toothbrush sanitizing assembly body end panel 314 and the end bristles 420 of the toothbrush 400. This same concept of end pads can be applied to any of the bristle restoration and maintenance apparatuses described herein.

Figure 12:
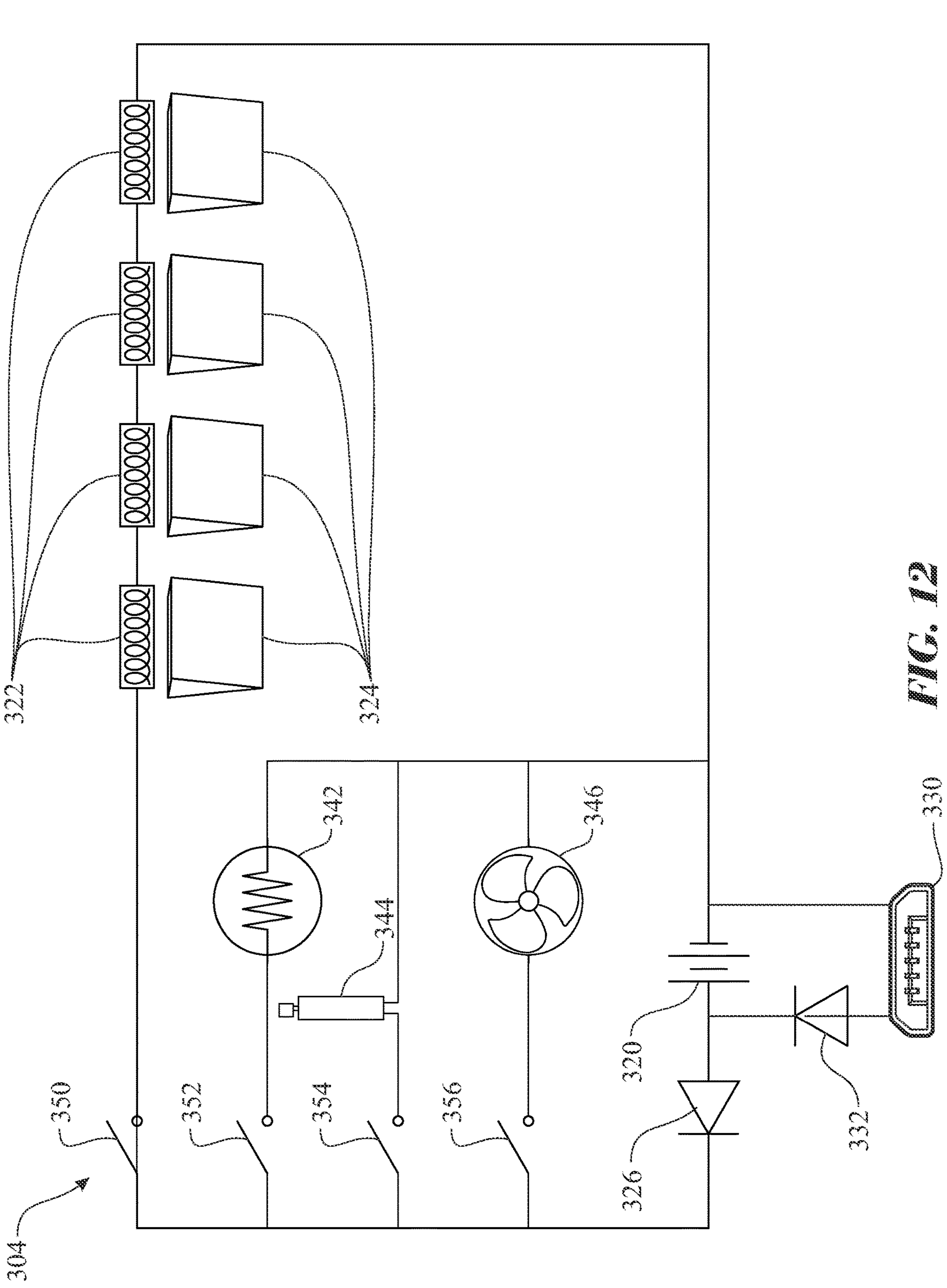
FIG. 12 presents a schematic diagram of an exemplary sanitizing circuit of the exemplary toothbrush sanitizing assembly originally introduced in FIG. 11.

An exemplary sanitizing schematic 304 of the operating components of the exemplary sanitizing system 300 is illustrated in FIG. 12. A toothbrush sanitizing assembly portable power supply 320 provides power to the operating circuit. The toothbrush sanitizing assembly portable power supply 320 can be charger/recharged by inserting a connector of a cable from a power source into a power charging source connector 330. The power charging source connector 330 would be in electrical communication with toothbrush sanitizing assembly portable power supply 320. This can be accomplished using a wired charging interface (as illustrated) or a wireless charging interface. A power charging circuit regulator 332 can be integrated into the charging portion of the circuitry to control the charging process. Power can be regulated throughout the circuit by at least one system power regulator 326. The circuit can additionally include one or more controllers (such as a microprocessor) (not illustrated). A sanitizing circuit operating switch 350 is preferably included, wherein the sanitizing circuit operating switch 350 provides a user with an ability to activate and deactivate the circuit. Upon activation, the circuit will illuminate each of at least one toothbrush sanitizing assembly sanitizing light source 322. The toothbrush sanitizing assembly sanitizing light source 322 is preferably a Ultra-Violet (UV) emitting light source. The toothbrush sanitizing assembly sanitizing light source 322 can be any sanitizing emission generating element. Each toothbrush sanitizing assembly sanitizing light source 322 is preferably coupled to a toothbrush sanitizing assembly sanitizing light pipe 324. Multiple toothbrush sanitizing assembly sanitizing light sources 322 can transmit light through an individual toothbrush sanitizing assembly sanitizing light pipe 324 or a common toothbrush sanitizing assembly sanitizing light pipe 324.

The toothbrush sanitizing assembly sanitizing light pipe 324 would be inserted between sets of 420. This arrangement optimizes the sanitation process by directing sanitizing light between bristles 420.

The circuit can additionally or alternatively include any of a number of sanitizing assistance elements. Exemplary sanitizing assistance elements illustrated in the circuit include a heater 342, a vibrator 344, and a fan 346. The heater 340 can be operated by a heater circuit operating switch 352. The heater 342 would aid in restoring the bristles 420. The vibrator 344 can be operated by a vibrator circuit operating switch 354. The vibrator 344 would aid in drying the 400; more specifically focusing on drying the bristles 420. The vibrations reduce a size of moisture droplets and separate the moisture droplets from the toothbrush assembly 400 by overcoming surface tension. The vibrator 344 can be operated by a vibrator circuit operating switch 354. The fan 346 would also aid in drying the 400 as well as cooling the toothbrush assembly 400; more specifically focusing on the bristles 420. The fan 346 can be operated by a fan circuit operating switch 356. By providing an arrangement with individual switches, the arrangement allows for controlled operated of each element independent of any other element. Although the sanitizing circuit operating switch 350, the heater circuit operating switch 352, the vibrator circuit operating switch 354, and the fan circuit operating switch 356 are illustrated as separate switches, it is understood that two or more of the sanitizing circuit operating switch 350, the heater circuit operating switch 352, the vibrator circuit operating switch 354, and the fan circuit operating switch 356 can be integrated into a single switch, activating two or more elements using a single switch. Although the exemplary circuit includes the toothbrush sanitizing assembly portable power supply 320, the heater 342, the vibrator 344, and the fan 346, it is understood that other devices that can assist in maintaining and sanitizing the toothbrush assembly 400 can be included within the circuit.

The toothbrush bristle restoration apparatus 200 is a modified version of the toothbrush bristle restoration apparatus 100. The toothbrush bristle restoration apparatus 200 includes a majority of like elements of the toothbrush bristle restoration apparatus 100. Like elements of the toothbrush bristle restoration apparatus 200 and the toothbrush bristle restoration apparatus 100 are numbered the same, wherein elements of the toothbrush bristle restoration apparatus 200 are preceded by the numeral "2".

Figure 13:
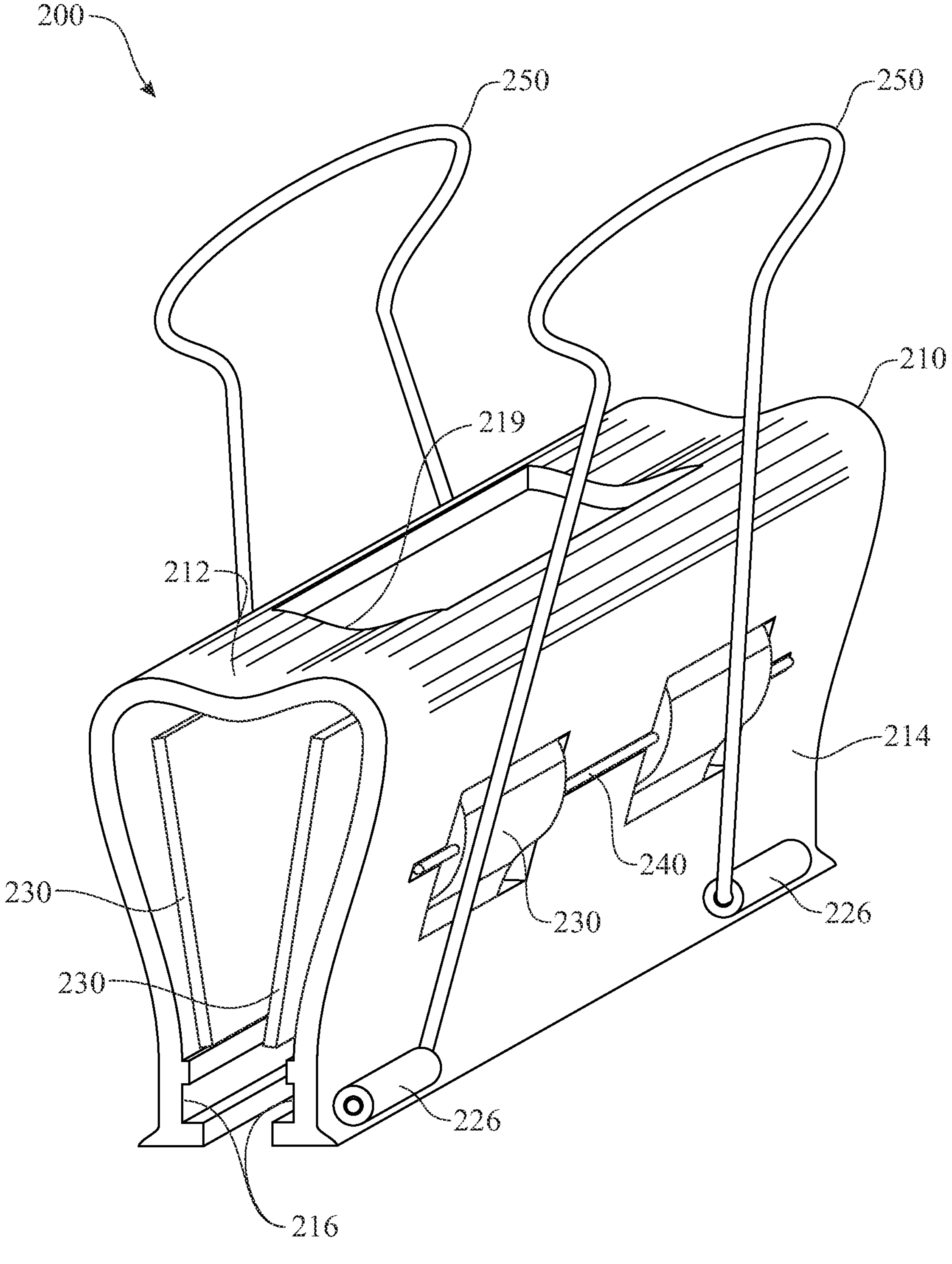
FIG. 13 presents an isometric front, top, side assembled view of a modified first exemplary version of the toothbrush bristle restoration apparatus originally introduced in FIG. 1, wherein the modified first exemplary version of the toothbrush bristle restoration apparatus is adapted to receive the exemplary toothbrush sanitizing assembly originally introduced in FIG. 11.

A toothbrush bristle restoration body sanitizer assembly receptacle 219 is formed through a toothbrush bristle restoration body top portion 212 of the toothbrush bristle restoration body 210 of the toothbrush bristle restoration apparatus 200, as shown in FIG. 13. The toothbrush bristle restoration body sanitizer assembly receptacle 219 is of a size and shape to enable the at least one toothbrush sanitizing assembly sanitizing light pipe 324 to pass through the toothbrush bristle restoration body sanitizer assembly receptacle 219, where each of the at least one toothbrush sanitizing assembly sanitizing light pipe 324 can be inserted between rows of sets of toothbrush bristles 420.

Figure 14:
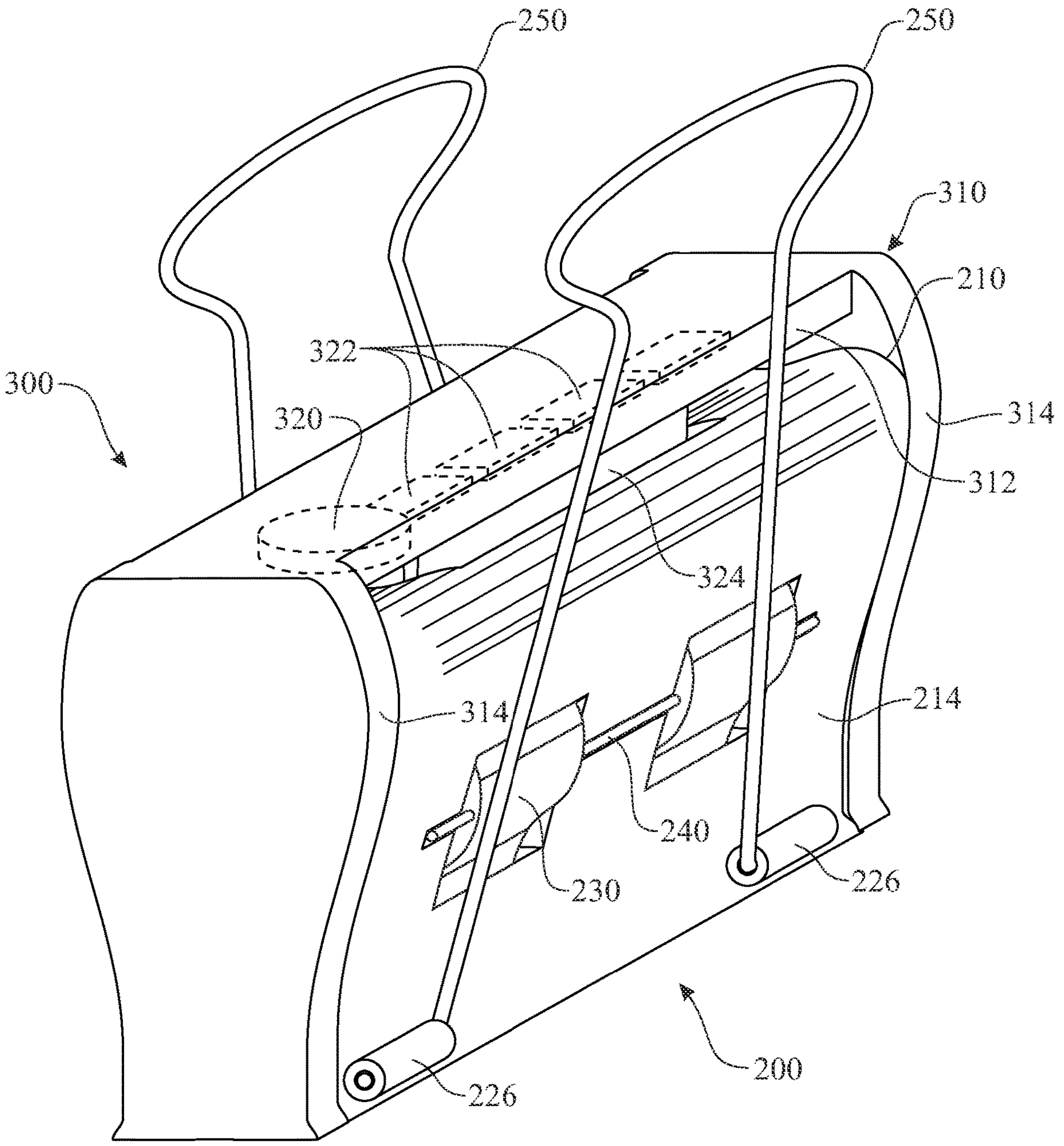
FIG. 14 presents an isometric front, top, side assembled view of the exemplary toothbrush sanitizing assembly originally introduced in FIG. 11 and the modified exemplary version of the toothbrush bristle restoration apparatus originally introduced in FIG. 11 being assembled to one another.

The exemplary application combines the toothbrush sanitizing assembly 300 and the toothbrush bristle restoration apparatus 200, as illustrated in FIGS. 14 and 15. The toothbrush sanitizing assembly 300 would be assembled to the toothbrush bristle restoration apparatus 200 by inserting the at least one toothbrush sanitizing assembly sanitizing light pipe 324 through the toothbrush bristle restoration body sanitizer assembly receptacle 219. A the toothbrush assembly 400 is being inserted into the toothbrush bristle restoration apparatus 200, the at least one toothbrush sanitizing assembly sanitizing light pipe 324 would be positioned between rows of sets of toothbrush bristles 420, as illustrated in FIG. 15. This provides a significant benefit in the sanitizing process, where the emitted sanitizing light is directed between the toothbrush bristles 420, where other known devices lack this capability. The more direct emission of the sanitizing light upon all surfaces of the toothbrush bristles 420 optimizes the process of sanitizing the toothbrush bristles 420.

The toothbrush sanitizing assembly sanitizing light pipe 324 can be shaped to accommodate the arrangement of the toothbrush bristles 420 of the toothbrush assembly 400. In the exemplary illustration, the toothbrush bristles 420 are arranged in linear rows. In other arrangements, the toothbrush bristles 420 can be arranged in an oval pattern, a circular pattern, a diamond shaped pattern, or any other desired arrangement. The toothbrush sanitizing assembly sanitizing light pipe 324 can be shaped to accommodate the respective patterns. The toothbrush sanitizing assembly sanitizing light pipe 324 can be exchangeable enabling the manufacturer and/or the user to select the appropriately shaped toothbrush sanitizing assembly sanitizing light pipe 324 for use with the respective toothbrush assembly 400.

The toothbrush bristle restoration apparatus 200 can be reshaped to be more aesthetically pleasing, such as a toothbrush bristle restoration apparatus 1300, presented in FIGS. 35 through 40. The toothbrush bristle restoration apparatus 1300 is a modified version of the toothbrush bristle restoration apparatus 200. The toothbrush bristle restoration apparatus 1300 includes a majority of like elements of the toothbrush bristle restoration apparatus 200. Like elements of the toothbrush bristle restoration apparatus 1300 and the toothbrush bristle restoration apparatus 200 are numbered the same, wherein elements of the toothbrush bristle restoration apparatus 1300 are preceded by the numeral "13".

Figure 38:
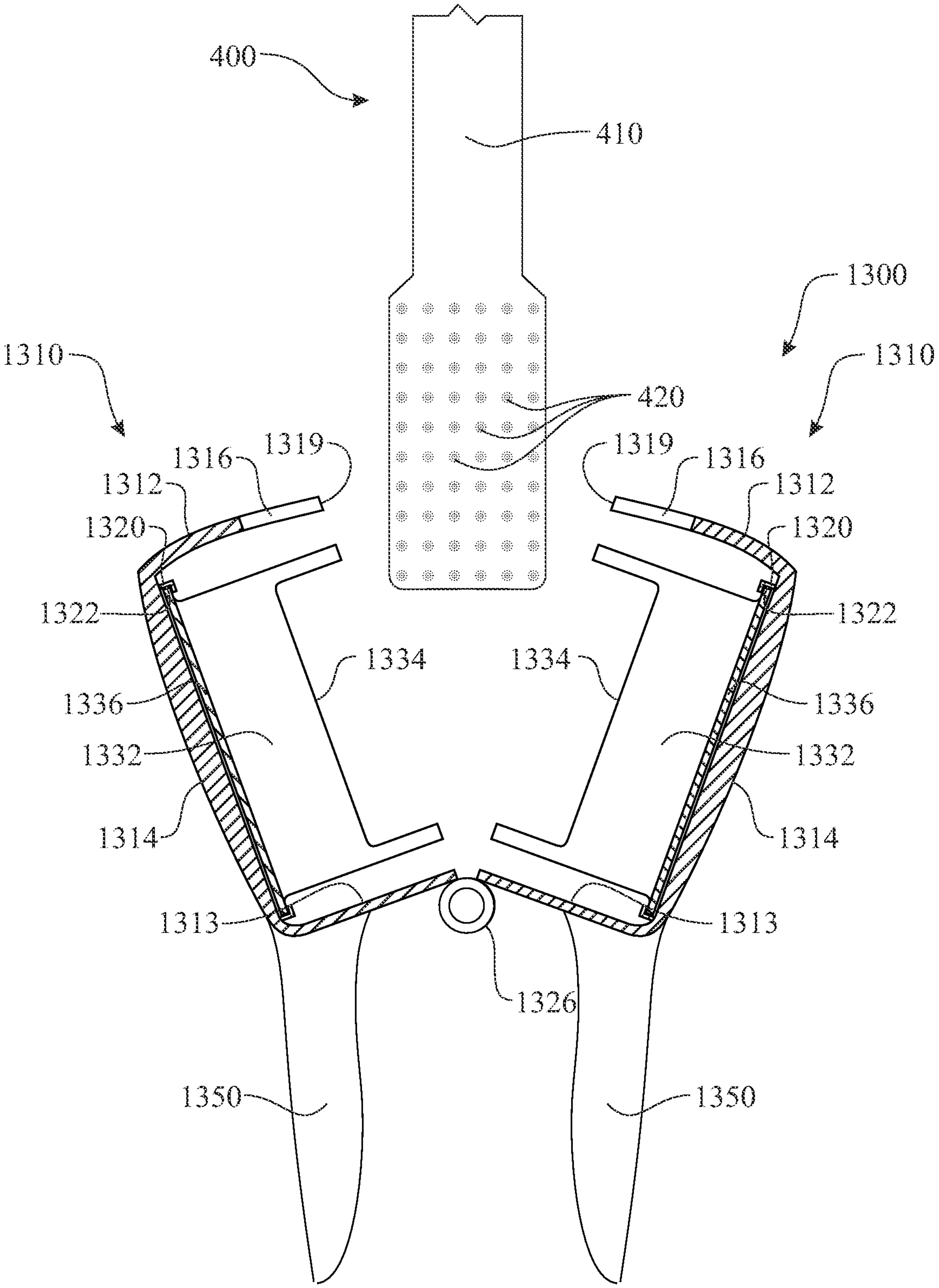
FIG. 38 presents a side sectioned view of the ninth exemplary toothbrush bristle restoration apparatus originally introduced in FIG. 35, the illustration presenting the toothbrush being inserted into an interior of the ninth exemplary toothbrush bristle restoration apparatus.
Figure 39:
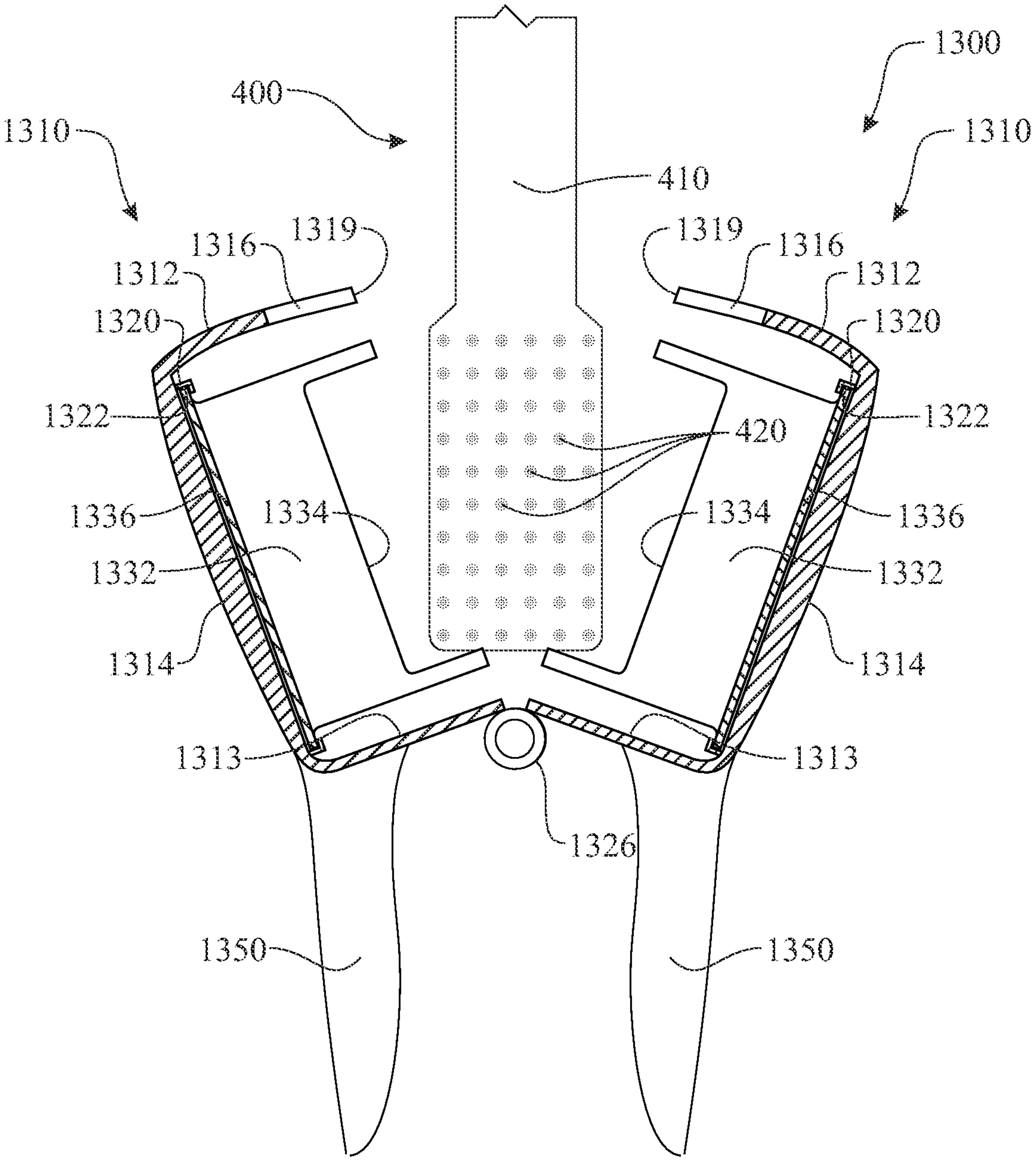
FIG. 39 presents a side sectioned view of the ninth exemplary toothbrush bristle restoration apparatus originally introduced in FIG. 35, the illustration presenting the toothbrush as inserted into an interior of the ninth exemplary toothbrush bristle restoration apparatus.
Figure 40:
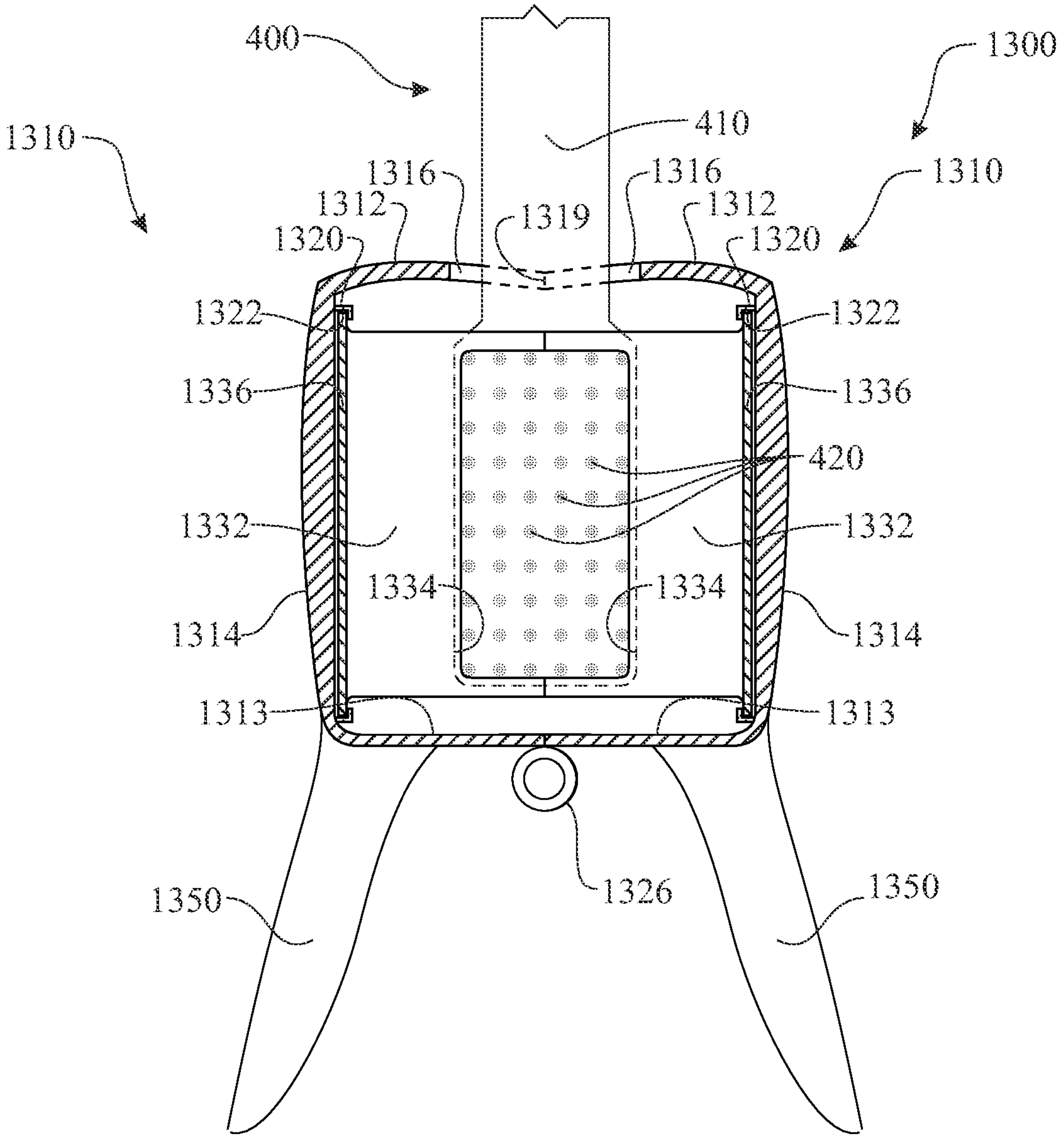
FIG. 40 presents a side sectioned view of the ninth exemplary toothbrush bristle restoration apparatus originally introduced in FIG. 35, the illustration presenting the toothbrush as inserted into an interior of the ninth exemplary toothbrush bristle restoration apparatus and the apparatus being closed applying a restoration and maintenance force to bristles of the toothbrush.

The toothbrush bristle restoration body 1310 is designed to substantially encase a head of the toothbrush assembly 400. The toothbrush bristle restoration body 1310 includes a toothbrush bristle restoration body top portion 1312 enclosing a top portion of a toothbrush bristle restoration body sidewall portion 1314 and a toothbrush bristle restoration body bottom portion 1313 enclosing a bottom portion of the toothbrush bristle restoration body sidewall portion 1314. A plurality of leverage arms 1350 extend downward and outward from the lower portion of the toothbrush bristle restoration body 1310. In the exemplary illustration, the toothbrush bristle restoration body 1310 and the leverage arms 1350 are formed to resemble a tooth; more specifically a tooth having four roots, such as a molar. The exemplary toothbrush bristle restoration body 1310 is designed to be used for each of a first half of the toothbrush bristle restoration body 1310 and a second half of the toothbrush bristle restoration body 1310 pivotally assembled to one another by inserting a toothbrush bristle restoration pad assembly pin shaft 1342 of a toothbrush bristle restoration pad assembly pin 1340 through apertures of each assembly hinge barrel 1326 and each adjacently located mating assembly hinge barrel 1327, as best illustrated in FIGS. 38 through 40. The only modification is the formation of the toothbrush bristle restoration body toothbrush clearance 1316 upon each toothbrush bristle restoration body 1310. A toothbrush bristle restoration pad assembly pin head 1344 and a like locking element retain the toothbrush bristle restoration pad assembly pin 1340 as a hinge pin pivotally assembling the assembly hinge barrel 1326 and the mating assembly hinge barrel 1327 to one another. A rotational biasing spring (not shown, but well understood by those skilled in the art) would be assembled about the hinge assembly providing a biasing force between each toothbrush bristle restoration body 1310 of the pair of toothbrush bristle restoration bodies 1310. The biasing force is arranged to maintain the toothbrush bristle restoration body mating edge 1319 of each toothbrush bristle restoration body 1310 against one another, retaining the pair of toothbrush bristle restoration bodies 1310 in a closed configuration. The leverage arm 1350 would be designed to support the toothbrush bristle restoration apparatus 1300 in an upright orientation in each of an empty condition and a toothbrush storing condition.

A toothbrush bristle restoration pad assembly 1330 comprising at least one toothbrush bristle restoration pad body 1332 extending outward from a toothbrush bristle restoration pad body assembly member 1336 is assembled to an interior surface of each toothbrush bristle restoration body 1310. Each of the at least one toothbrush bristle restoration pad body 1332 includes a toothbrush bristle restoration pad body bristle contacting surface 1334. In one vision, the toothbrush bristle restoration apparatus 1300 would be offered including a plurality of pairs of toothbrush bristle restoration pad assemblies 1330, wherein each pair would include a toothbrush bristle restoration pad body bristle contacting surface 1334 having a shape that differs from the toothbrush bristle restoration pad body bristle contacting surface 1334 of the other pairs of toothbrush bristle restoration pad assemblies 1330. Each pair of toothbrush bristle restoration pad assembly 1330 would have a toothbrush bristle restoration pad body bristle contacting surface 1334 distinctly shaped for a specifically shaped arrangement of toothbrush bristles 420 of the toothbrush assembly 400. The user would select the specific pair of toothbrush bristle restoration pad assemblies 1330 for the arrangement of their toothbrush assembly 400 and assemble the selected pair of toothbrush bristle restoration pad assemblies 1330 to each toothbrush bristle restoration body 1310. The toothbrush bristle restoration pad body bristle contacting surface 1334 can be shaped to contact both the sides of the sets of the toothbrush bristles 420 and the ends of the sets of the toothbrush bristles 420.

In the exemplary illustration, the toothbrush bristle restoration pad body assembly member 1336 is slideably inserted into a pair of toothbrush bristle restoration body restoration panel receiving member channel 1322 formed within a pair of opposite facing toothbrush bristle restoration body restoration panel receiving members 1320. The toothbrush bristle restoration body restoration panel receiving members 1320 are formed in each interior wall; one toothbrush bristle restoration body restoration panel receiving member 1320 provided proximate the toothbrush bristle restoration body bottom portion 1313 and the second toothbrush bristle restoration body restoration panel receiving member 1320 provided proximate the 1312, as best shown in FIGS. 38 through 40. A toothbrush bristle restoration body restoration panel receiving member end stop 1324 can extend between like ends of the pair of toothbrush bristle restoration body restoration panel receiving members 1320. The toothbrush bristle restoration pad body assembly member 1336 is slideably inserted into each toothbrush bristle restoration body restoration panel receiving member channel 1322 until a leading edge contacts the toothbrush bristle restoration body restoration panel receiving member end stop 1324.

The toothbrush bristle restoration body 1310 is preferably fabricated of a more rigid plastic material. The toothbrush bristle restoration pad assembly 1330 is fabricated of a plaint material such as a nylon, a rubber, or any other suitably flexible material. The toothbrush bristle restoration pad assembly pin 1340 can be fabricated of a sturdy plastic, a metal, or any other material suitable as a hinge pin.

A toothbrush sanitizing assembly 302 can be fabricated of a shape and size to be assembled to an interior surface within the toothbrush bristle restoration body 1310, where the toothbrush sanitizing assembly 302 would be effective for sanitizing the toothbrush bristles 420 of the toothbrush assembly 400. The toothbrush sanitizing assembly 302 would include some or all of the elements as described in the toothbrush sanitizing circuit 304 illustrated in FIG. 12.

Figure 41:
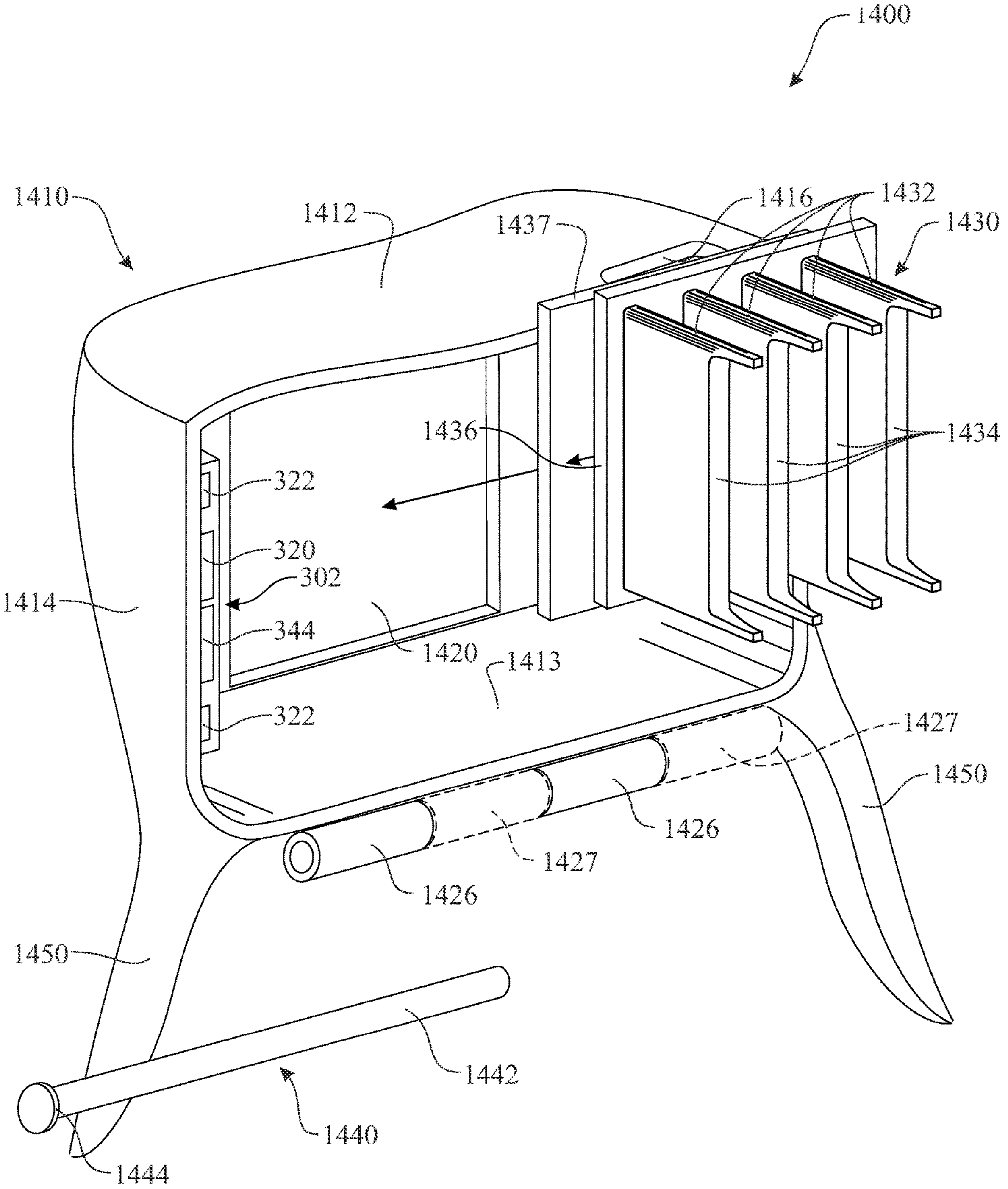
FIG. 41 presents a isometric front side partially exploded assembly view of one side of a tenth exemplary toothbrush bristle restoration apparatus, the tenth exemplary toothbrush is a modified variant of the ninth exemplary toothbrush bristle restoration apparatus originally introduced in FIG. 35, wherein the distinction is a manner of assembly of the flexible bristle restoration members to an interior surface of the housing.

The toothbrush bristle restoration apparatus 1300 employs a sliding assembly interface to slideably assemble the toothbrush bristle restoration pad assembly 1330 to the toothbrush bristle restoration body 1310. The toothbrush bristle restoration pad assembly 1330 can be assembled to the toothbrush bristle restoration body 1310 using any suitable design. One alternative example is a toothbrush bristle restoration apparatus 1400 illustrated in FIG. 41. The toothbrush bristle restoration apparatus 1400 includes a majority of like elements of the toothbrush bristle restoration apparatus 1300. Like elements of the toothbrush bristle restoration apparatus 1400 and the toothbrush bristle restoration apparatus 1300 are numbered the same, wherein elements of the toothbrush bristle restoration apparatus 1300 are preceded by the numeral "14". The distinction is the assembly interface for assembling a toothbrush bristle restoration pad assembly 1430 to an interior surface of a toothbrush bristle restoration body 1410. A toothbrush bristle restoration pad body assembly member 1436 of the toothbrush bristle restoration pad assembly 1430 can be adhesively bonded directly to a toothbrush bristle restoration pad assembly receiving cavity 1420 formed within an interior wall of a toothbrush bristle restoration body sidewall portion 1414 of the toothbrush bristle restoration body 1410. Alternatively, the toothbrush bristle restoration pad body assembly member 1436 of the toothbrush bristle restoration pad assembly 1430 can be adhesively bonded to a toothbrush bristle restoration pad spacer 1437, wherein the toothbrush bristle restoration pad spacer 1437 is then adhesively bonded to the toothbrush bristle restoration pad assembly receiving cavity 1420 formed within the interior wall of the toothbrush bristle restoration body sidewall portion 1414 of the toothbrush bristle restoration body 1410. The user can select one of several toothbrush bristle restoration pad spacer 1437 provided to change a span between opposing toothbrush bristle restoration pad body bristle contacting surfaces 1434. The toothbrush bristle restoration apparatus 1300 can be provided as a kit, wherein the kit includes a series of pairs of toothbrush bristle restoration pad spacers 1437, each pair having a distinct thickness compared to other pairs, thus enabling an adjustment to the span between opposing toothbrush bristle restoration pad body bristle contacting surfaces 1434. In a preferred arrangement, adhesive would be applied to one or both bonding surfaces of the of toothbrush bristle restoration pad spacer 1437.

The design and arrangement of the toothbrush bristle restoration pad body bristle contacting surface 1334 of the toothbrush bristle restoration pad body 1332 provides a restoration force to a distal region (farthest from the toothbrush body 410) of the toothbrush bristles 420 across the entire side region. The design and arrangement of the toothbrush bristle restoration pad body bristle contacting surface 1334 of the toothbrush bristle restoration pad body 1332 can additionally provide a restoration force to intermediate regions (a region extending between the distal region of the toothbrush bristles 420 and a base region of the toothbrush bristles 420) of the toothbrush bristles 420 across the entire side region of the bristles 420. The design and arrangement of the toothbrush bristle restoration pad body bristle contacting surface 1334 of the toothbrush bristle restoration pad body 1332 can additionally provide a restoration force to a front portion (farthest from a grip portion of the toothbrush body 410) of the toothbrush bristles 420 and a rear portion (nearest to the grip portion of the toothbrush body 410) of the toothbrush bristles 420.

Figure 42:
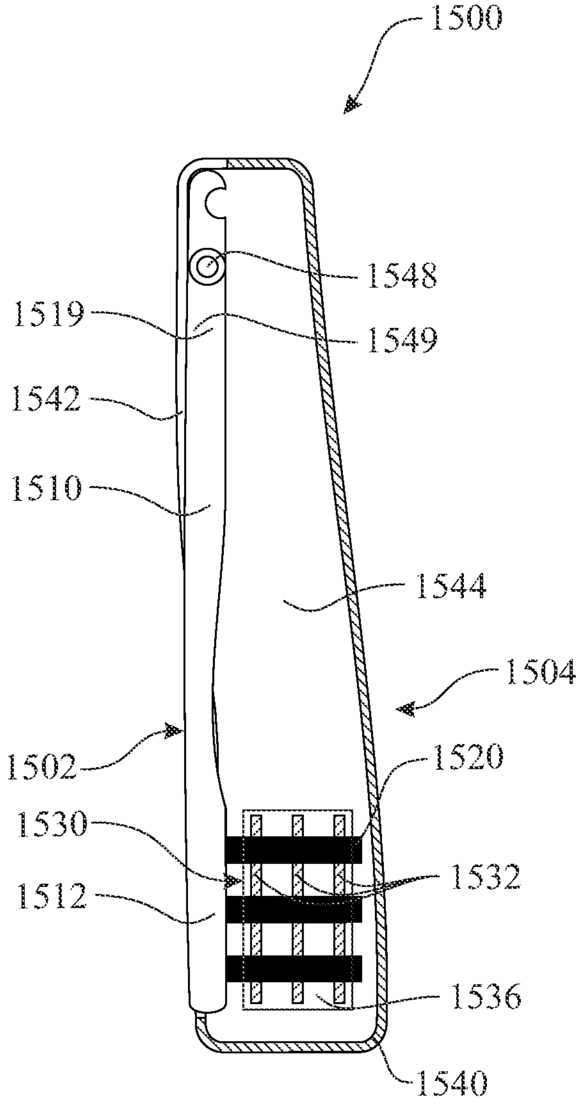
FIG. 42 presents a side sectioned view of an eleventh exemplary toothbrush bristle restoration apparatus, the eleventh exemplary toothbrush integrated the exemplary toothbrush bristle restoration elements within a cavity formed within a grip end of a folding toothbrush, the illustration presenting the eleventh exemplary toothbrush bristle restoration apparatus in a closed configuration.
Figure 43:
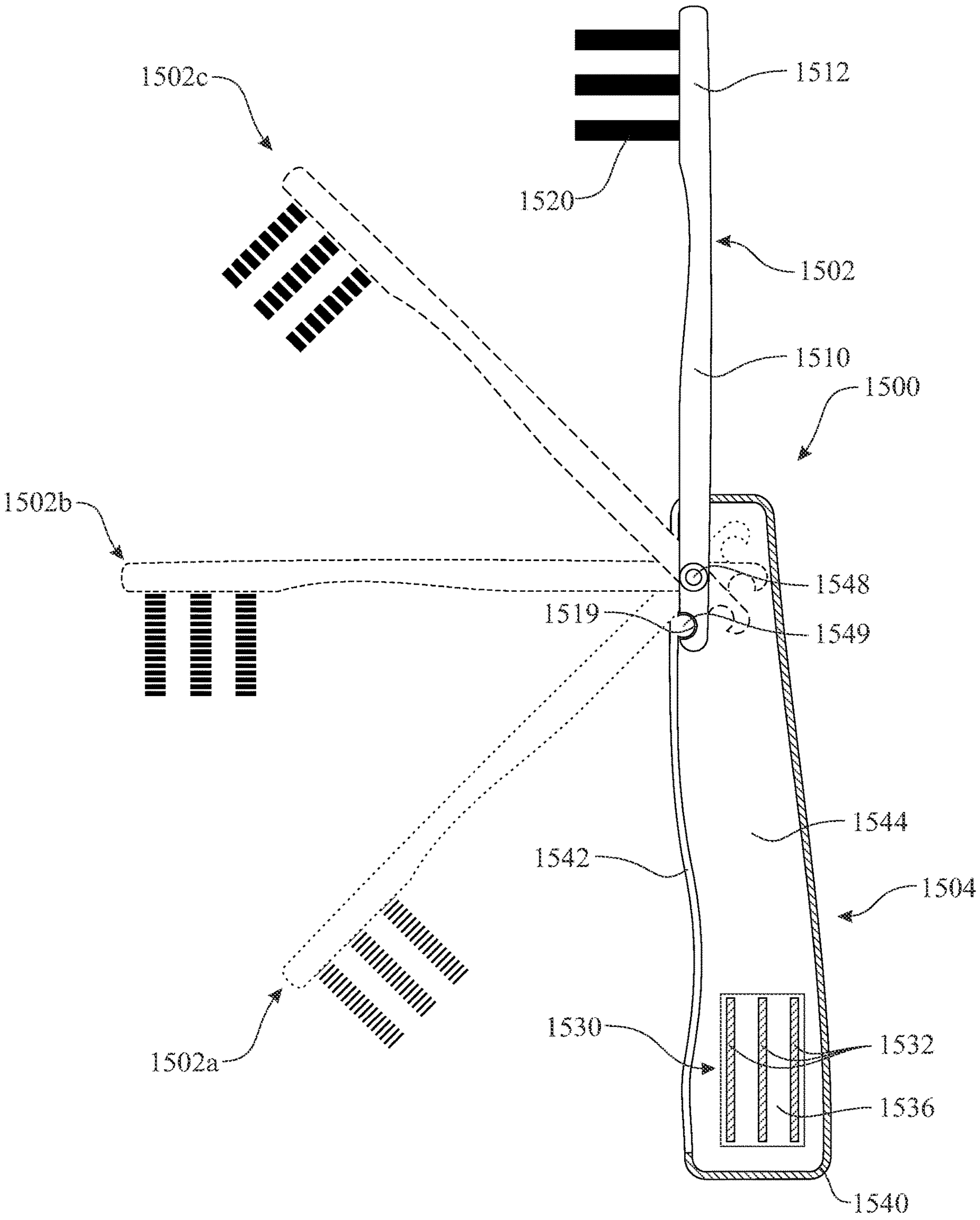
FIG. 43 presents a side sectioned view of the eleventh exemplary toothbrush bristle restoration apparatus originally introduced in FIG. 42, the illustration presenting the eleventh exemplary toothbrush bristle restoration apparatus in an opened configuration.
Figure 44:
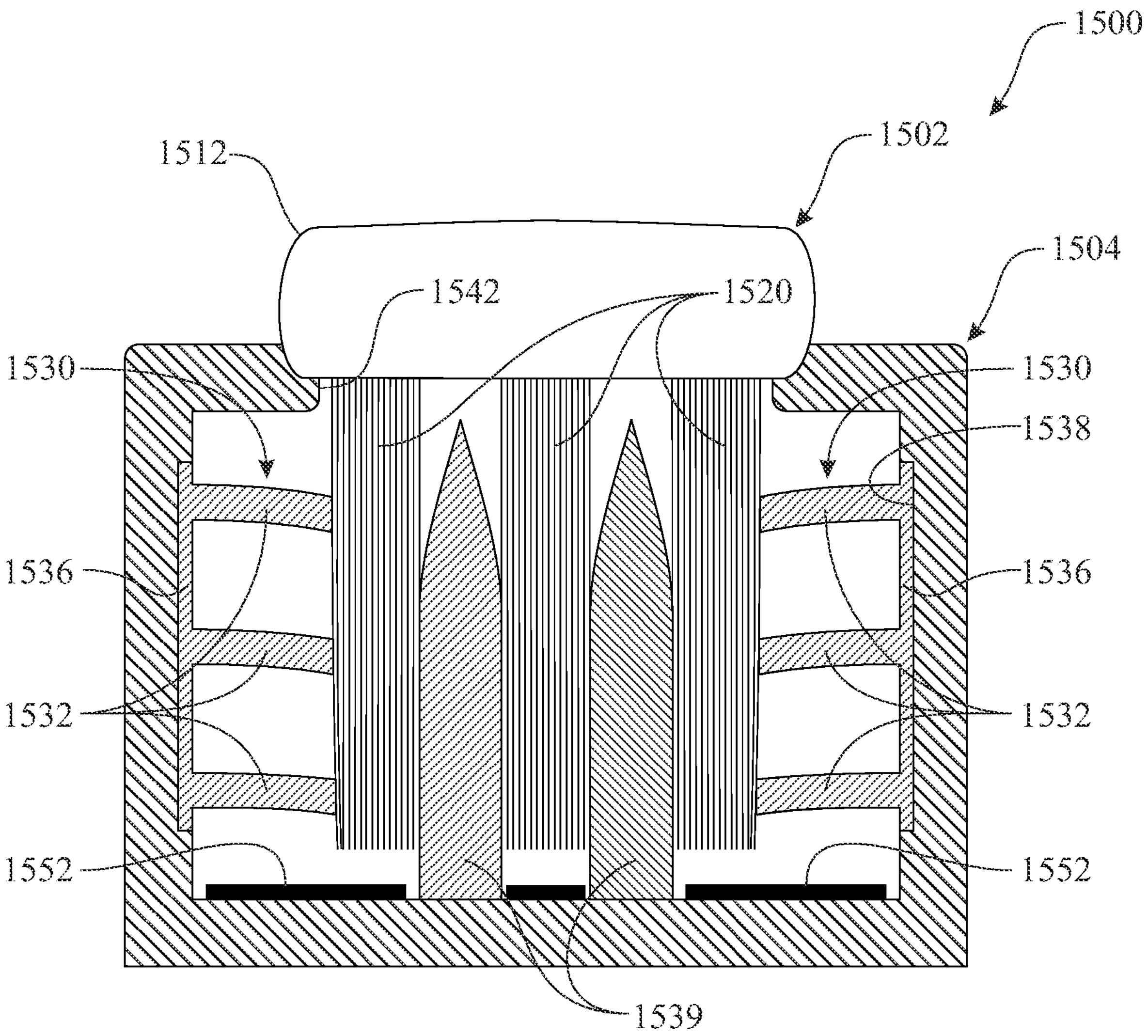

The previously described toothbrush sanitizing assemblies are separate from the toothbrush assembly 400. The toothbrush sanitizing assembly can be integrated into the toothbrush. A compact toothbrush with integral bristle maintenance system 1500, presented in FIGS. 42 through 44 is an exemplary such solution. The compact toothbrush with integral bristle maintenance system 1500 includes a compact toothbrush upper body segment 1502 and a compact toothbrush lower body segment 1504 that are pivotally assembled to one another by a compact toothbrush upper body pivot member 1548. The compact toothbrush upper body segment 1502 includes a compact toothbrush head 1512 at a distal end of a compact toothbrush upper body 1510. A series of groups of bristles 1520 are assembled to the compact toothbrush head 1512 of the compact toothbrush upper body segment 1502. A compact toothbrush upper body locking element 1519 is formed proximate a pivotal end of the compact toothbrush upper body segment 1502.

The compact toothbrush lower body segment 1504 includes a compact toothbrush lower body 1540 shaped to define a compact toothbrush upper body receiving clearance 1544. A compact toothbrush upper body receiving passageway 1542 enables pivotal insertion of the compact toothbrush upper body segment 1502 into and removal therefrom the compact toothbrush upper body receiving clearance 1544, as illustrated in FIGS. 42 and 43 (as identified by 1502_a_, 1502_b_, 1502_c_). A compact toothbrush upper body locking element 1519 can be included in the compact toothbrush lower body segment 1504. The compact toothbrush lower body locking element 1549 engages with the compact toothbrush lower body segment 1504 when the compact toothbrush upper body segment 1502 is fully rotated into an opened position (as illustrated in FIG. 43). A bristle restoration and maintenance element 1530 is provided within the compact toothbrush upper body receiving clearance 1544 at a location to engage with the bristles compact toothbrush bristles 1520, as illustrated in FIG. 44. The exemplary bristle restoration and maintenance element 1530 includes a series of flanges fabricated of a pliant or compressible material, such as rubber or foam. A bristle restoration and maintenance element mounting block 1536 of the bristle restoration and maintenance element 1530 can be adhesively assembled within the bristle restoration and maintenance element mounting block receptacle 1538 of the compact toothbrush lower body 1540. A bristle sanitizing element 1552 can be placed upon an interior surface of the compact toothbrush lower body 1540. The bristle sanitizing element 1552 would be similar to the sanitizing pad 652 described above. At least one bristle restoration and maintenance intermediary element 1539 can be included, wherein each of the at least one bristle restoration and maintenance intermediary element 1539 would be sized, shaped and located to be inserted between adjacent sets of bristles compact toothbrush bristles 1520 of the compact toothbrush upper body segment 1502. The bristle sanitizing element 1552 can be shaped to slide over the bristle restoration and maintenance intermediary elements 1539 and adhesively bonded to the interior surface of the compact toothbrush lower body 1540 as illustrated in FIG. 44.

In use, the compact toothbrush upper body segment 1502 would be pivoted to a point where the compact toothbrush lower body locking element 1549 engages with the compact toothbrush upper body locking element 1519, locking the compact toothbrush upper body segment 1502 into an open position. When the user is finished with the compact toothbrush with integral bristle maintenance system 1500, the compact toothbrush upper body segment 1502 is pivoted into a closed position, where the compact toothbrush bristles 1520 is inserted between the bristle restoration and maintenance element 1530. The compact toothbrush with integral bristle maintenance system 1500 can include a snap feature, retaining the compact toothbrush upper body segment 1502 in a closed position. The compact toothbrush upper body receiving passageway 1542 can be designed to expose a portion of the compact toothbrush upper body 1510, providing access to a grip, enabling a user to open the compact toothbrush with integral bristle maintenance system 1500 as desired for use.

The bristle restoration and maintenance element 1530 illustrated is only exemplary. The compact toothbrush with integral bristle maintenance system 1500 can be any suitable design to accomplish the desired function, including any of the previously disclosed designs or any other suitable designs.

Figure 16:
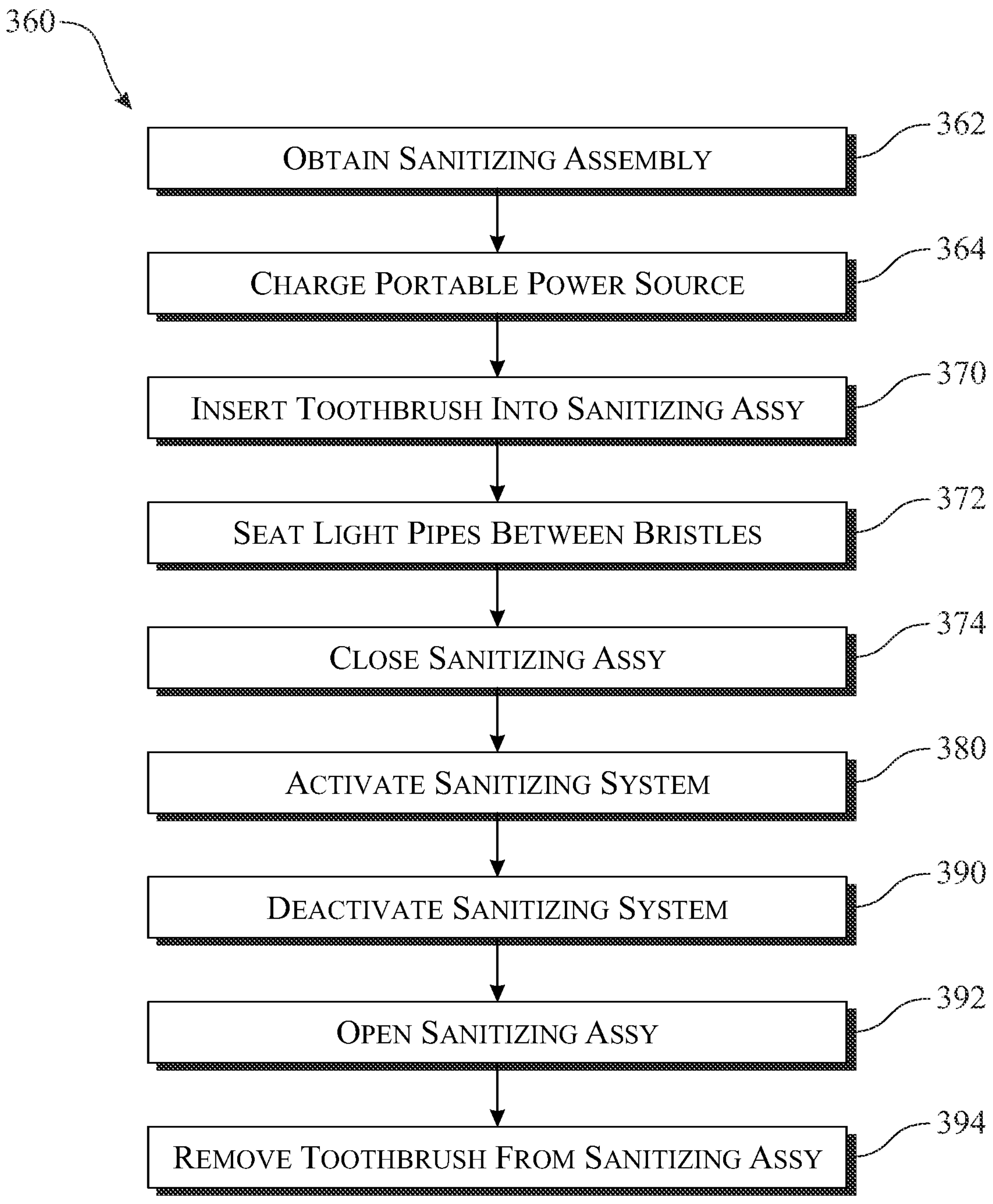
FIG. 16 presents a flow diagram of a first exemplary toothbrush bristle sanitizing process, wherein the first exemplary toothbrush bristle sanitizing system employs emissions of ultraviolet light.

Operation of the toothbrush sanitizing assembly 300 is described in an exemplary bristle sanitization flow diagram 360, presented in FIG. 16. The bristle sanitization flow diagram 360 initiates with an obtain bristle sanitizing assembly step 362. In the exemplary illustrations, the toothbrush sanitizing assembly 300 works in conjunction with the toothbrush bristle restoration apparatus 200. The toothbrush sanitizing assembly 300 can also be utilized with a custom enclosure, exclusive of the restoration function. The toothbrush sanitizing assembly portable power supply 320 of the toothbrush sanitizing assembly 300 is charged by connecting a power source to the circuit (step 364). The toothbrush assembly 400 and the toothbrush sanitizing assembly 300 are engaged with one another in a manner associated with the design of the toothbrush sanitizing assembly 300 (step 370). In the exemplary illustration, the toothbrush assembly 400 is retained by the toothbrush bristle restoration apparatus 200. The toothbrush sanitizing assembly 300 is assembled to the toothbrush bristle restoration apparatus 200. During the process of inserting the toothbrush sanitizing assembly 300 into the toothbrush bristle restoration body sanitizer assembly receptacle 219 of the toothbrush bristle restoration apparatus 200, the toothbrush sanitizing assembly sanitizing light pipes 324 are positioned between sets of bristles 420 of the toothbrush assembly 400 (step 372). The sanitizing assembly is then closed (step 374). The sanitizing circuit is activated (step 380), such as by activating the sanitizing circuit operating switch 350. Once activated, the circuit emits a sanitizing emission (such as a Ultra-Violet light) by the at least one toothbrush sanitizing assembly sanitizing light source 322. The process would run until manually deactivated, until a time expires and automatically deactivated, or until any other deactivation process is determined (deactivation step 390). Upon deactivation, the sanitizing assembly is opened (step 392). The toothbrush assembly 400 is then removed from the sanitizing assembly for use (step 394).

In an arrangement where the toothbrush sanitizing assembly 300 is independently used, the outer walls can be used at light pipes, enabling emission of the sanitizing light towards the exterior region of the toothbrush bristles 420. In an arrangement where the toothbrush sanitizing assembly 300 is used in combination with the toothbrush bristle restoration apparatus 200, the toothbrush bristle restoration pad 230 can be utilized as a light pipe to direct emission of the sanitizing light towards the exterior region of the toothbrush bristles 420. The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

In yet another arrangement, each of the toothbrush bristle restoration pad bodies can be perforated, designed to include a series of fins, similar to the toothbrush bristle restoration pad bodies 1332 of the toothbrush bristle restoration pad assemblies 1330, or be of any other configuration or include any suitable feature allowing airflow therethrough, enabling drying of the bristles 420 and exposure to the sanitizing process.

What is claimed is:

1. A method of maintaining for a toothbrush, the method comprising steps of:

obtaining a toothbrush bristle restoration apparatus, the toothbrush bristle restoration apparatus comprising:

a first toothbrush bristle restoration body, and a second toothbrush bristle restoration body, wherein the first toothbrush bristle restoration body and the second toothbrush bristle restoration body are moveably assembled to one another;

selecting a pair of bristle restoration pads from a group of pairs of bristle restoration pads, provided as a kit to an end user, each of the pair of bristle restoration pads includes a first bristle restoration pad and a separate, second bristle restoration pad having a bristle restoration pad contacting surface selected from a group of pairs of bristle restoration pads, each pair of bristle restoration pads having different shaped bristle restoration pad bristle contacting surface from the other pairs of bristle restoration pads, wherein each bristle restoration pad contacting surface is formed having a series of alternating bristle touching surfaces and gaps;

installing the first bristle restoration pad into the first toothbrush bristle restoration body;

installing the second bristle restoration pad into the second toothbrush bristle restoration body;

maintaining the toothbrush by:

(a) separating the first toothbrush bristle restoration body and the second toothbrush bristle restoration body to provide a gap between the first bristle restoration pad and the second bristle restoration pad enabling insertion of the toothbrush, (b) inserting the toothbrush between the bristle restoration pads bristle contacting surfaces installed in each of the first toothbrush bristle restoration body and the second toothbrush bristle restoration body of the toothbrush bristle restoration apparatus, while the respective bristle restoration pad remains installed within the respective toothbrush bristle restoration body; and (c) applying a restoration force to each side of bristles of the toothbrush by bringing each of the first toothbrush bristle restoration body and the second toothbrush bristle restoration body of the bristle restoration apparatus together, while the respective bristle restoration pad remains installed within the respective toothbrush bristle restoration body, (d) separating the separating the first toothbrush bristle restoration body and the second toothbrush bristle restoration body to provide a gap between the first bristle restoration pad and the second bristle restoration pad enabling removal of the toothbrush, repeating steps (a) through (d).

2. The method of caring for a toothbrush as recited in claim 1, each bristle restoration pad a plurality of cantilevered fins extending outward from a restoration pad body assembly member, a distal, free end of each of the thin cantilevered fins forming the series of alternating bristle touching surfaces and gaps of the bristle restoration pad bristle contacting surface, the wherein of installing each of the first bristle restoration pad and the second bristle restoration pad into each respective toothbrush bristle restoration body is accomplished by assembling the restoration pad body assembly member to the respective toothbrush bristle restoration body of prior to insertion of the toothbrush into the toothbrush bristle restoration apparatus.

3. The method of caring for a toothbrush as recited in claim 1, wherein the steps of (a) installing the first bristle restoration pad bodies into the first toothbrush bristle restoration body and (b) installing the second bristle restoration pad of the selected pair of bristle restoration pad bodies into the second toothbrush bristle restoration body is accomplished via at least one of:

a) a pin,
b) a pin and groove,
c) a pin and bore,
d) a snap interface,
e) a tongue and groove interface,
f) a channel,
g) a key-slot interface,
h) a threaded interface,
i) an adhesive interface, and
j) an adhesive interface in combination with a receiving cavity.

4. The method of caring for a toothbrush as recited in claim 1, the method further comprising a step of:

between steps (c) and (d), applying a retention force to the first toothbrush bristle restoration body and the second toothbrush bristle restoration body to retain the first toothbrush bristle restoration body and the second toothbrush bristle restoration body in a closed configuration entrapping the bristles of the toothbrush between each of the first bristle restoration pad and the second bristle restoration pad until removal of the toothbrush is desired.

5. The method of caring for a toothbrush as recited in claim 1, wherein the first toothbrush bristle restoration body and the second toothbrush bristle restoration body are at least one of:

a) provided as a unitary member and flex between a separated and compressed state,
b) pivotally assembled to one another,
c) pivotally assembled to one another, including a biasing element to retain the first toothbrush bristle restoration body and the second toothbrush bristle restoration body in a contracted configuration,
d) assembled to one another by a third member, wherein the third member includes an expansion and contraction mechanism,
e) assembled to one another by a third member, wherein the third member includes an expansion and contraction mechanism, the expansion and contraction mechanism including a threaded element,
f) assembled to one another by a third member, wherein the third member includes an expansion and contraction mechanism, the expansion and contraction mechanism including a biasing element, and
g) pivotally assembled to a third member.

6. The method of caring for a toothbrush as recited in claim 1, wherein at least a portion of the sides of the bristles are retained in position by a plurality of spatially arranged supporting surfaces of the bristle restoration pads, wherein the supporting surfaces are spatially arranged between an attachment end of the bristles and a free end of the bristles spatially exposing a majority of the sides of the bristles, further comprising a step of directing a sanitizer towards the sides of the bristles along an entire length of the exposed portion of the sides of the bristles.

7. The method of caring for a toothbrush as recited in claim 1, the method further comprising a step of:

directing a sanitizer towards the sides of the bristles, wherein the sanitizer includes at least one of:

a) an Ultraviolet (UV) light,
b) an Ultraviolet (UV) light emitting element,
c) an Ultraviolet (UV) Light Emitting Diode (LED),
d) a light pipe,
e) a light pipe located to extend between rows of bristles of the toothbrush,
f) a sanitizing strip,
g) a sanitizing strip comprising a carrier,
h) a sanitizing strip comprising a carrier, an adhesive and a sanitizing solution embedded in the carrier,
i) a sanitizing composition comprising an alcohol based solution,
j) a sanitizing composition comprising a chlorine based solution,
k) a sanitizing composition comprising a sodium hypochlorite based solution,
l) A sanitizing composition comprising a glutaraldehyde based solution,
m) a sanitizing composition comprising a hydrogen peroxide based solution,
n) a sanitizing composition comprising an iodophor based solution,
o) A sanitizing composition comprising an ortho-phthalaldehyde based solution,
p) a sanitizing composition comprising a peracetic acid based solution,
q) a sanitizing composition comprising a peroxyacetic acid based solution, r) a sanitizing composition comprising a phenol based solution, and/or s) a sanitizing composition comprising a quaternary ammonium compound based solution.

8. The method of caring for a toothbrush as recited in claim 1, wherein the separating the first toothbrush bristle restoration body and the second toothbrush bristle restoration body and the bringing each of the first toothbrush bristle restoration body and the second toothbrush bristle restoration body of the bristle restoration apparatus together are accomplished in accordance with at least one of:

a rotational motion, and a linear motion.

9. The method of caring for a toothbrush as recited in claim 1, wherein at least one of the first toothbrush bristle restoration body and the second toothbrush bristle restoration body is at least partially fabricated of one of a translucent material and a transparent material, the toothbrush bristle restoration apparatus further comprising a light emitting circuit, the method further comprising a step of:

emitting light through the one of the translucent material and the transparent material of the at least one of the first toothbrush bristle restoration body and the second toothbrush bristle restoration body, wherein the emitted light is visible externally respective to the first toothbrush bristle restoration body and the second toothbrush bristle restoration body providing illumination external of the toothbrush bristle restoration apparatus.

10. The method of caring for a toothbrush as recited in claim 1, wherein a first bristle restoration pad bristle contacting surface and a second bristle restoration pad bristle contacting surface of the selected toothbrush bristle restoration pad assembly are shaped to accommodate one of the following toothbrush head shapes:

a) a toothbrush having a linear and parallel side portion of the series of bristles, b) a toothbrush having a round side portion of the series of bristles, c) a toothbrush having a linear and angled side portion of the series of bristles, d) a toothbrush having a diamond shaped side portion of the series of bristles, and e) a toothbrush having an irregular shaped side portion of the series of bristles.

11. A method of caring for a toothbrush, the method comprising steps of:

obtaining a toothbrush bristle restoration apparatus, the toothbrush bristle restoration apparatus comprising:

a first toothbrush bristle restoration body, and a second toothbrush bristle restoration body, wherein the first toothbrush bristle restoration body and the second toothbrush bristle restoration body are moveably assembled to one another;

selecting a pair of toothbrush bristle restoration pads from a group of pairs of toothbrush bristle restoration pads provided as a kit to an end user, each pair of bristle restoration pads includes a first bristle restoration pad and a separate, second bristle restoration pad, each toothbrush bristle restoration pad assembly includes a plurality of toothbrush bristle restoration pad contacting surfaces at a distal end of the toothbrush bristle restoration pad assembly, each toothbrush bristle restoration pad contacting surface includes a series of alternating bristle touching surfaces and gaps sized to substantially span an entire length of bristles of a toothbrush, wherein each pair of the pairs of toothbrush bristle restoration pads has a different shaped toothbrush bristle restoration pad contacting surface compared to the other toothbrush bristle restoration pad contacting surfaces of the other pairs of toothbrush bristle restoration pad members, wherein the pair of toothbrush bristle restoration pads is selected by matching a shape of the toothbrush bristle restoration pad contacting surfaces to a shape of the bristles of the toothbrush, installing the first bristle restoration pad into the first toothbrush bristle restoration body;

installing the second bristle restoration pad into the second toothbrush bristle restoration body;

maintaining the toothbrush by:

(a) separating the first toothbrush bristle restoration body and the second toothbrush bristle restoration body to provide a gap between the first bristle restoration pad and the second bristle restoration pad enabling insertion of the toothbrush, (b) inserting the toothbrush between the bristle restoration pads bristle contacting surfaces of the bristle restoration pads installed in each of the first toothbrush bristle restoration body and the second toothbrush bristle restoration body, while the respective bristle restoration pad remains installed within the respective toothbrush bristle restoration body; and (c) applying a restoration force to each side of bristles of the toothbrush by bringing each of the first toothbrush bristle restoration body and the second toothbrush bristle restoration body of the bristle restoration apparatus together, while the respective bristle restoration pad remains installed within the respective toothbrush bristle restoration body, wherein the bristle touching surfaces contact a portion of substantially an entire length of the bristles extending between an attachment end of the bristles and a free end thereof and the gaps expose a remaining portion of the bristles, wherein the gaps enable an application of a sanitizer, (d) separating the separating the first toothbrush bristle restoration body and the second toothbrush bristle restoration body to provide a gap between the first bristle restoration pad and the second bristle restoration pad enabling removal of the toothbrush, repeating steps (a) through (d).

12. The method of caring for a toothbrush as recited in claim 11, wherein each bristle restoration pad is a thin cantilevered fin extending outward from a restoration pad body assembly member, wherein the method of installing each of the first bristle restoration pad and the second bristle restoration pad into each respective toothbrush bristle restoration body is accomplished by assembling the restoration pad body assembly member to the toothbrush bristle restoration body of prior to insertion of the toothbrush into the toothbrush bristle restoration apparatus.

13. The method of caring for a toothbrush as recited in claim 11, wherein the steps of (a) installing the first bristle restoration pad of the selected pair of bristle restoration pads into the first toothbrush bristle restoration body of the toothbrush bristle restoration apparatus and (b) installing the second bristle restoration pad of the selected pair of bristle restoration pads into the second toothbrush bristle restoration body of the toothbrush bristle restoration apparatus is accomplished via at least one of:

a) a pin, b) a pin and groove, c) a pin and bore, d) a snap interface,
e) a tongue and groove interface,
f) a channel,
g) a key-slot interface,
h) a threaded interface,
i) an adhesive interface, and
j) an adhesive interface in combination with a receiving cavity.

14. The method of caring for a toothbrush as recited in claim 11, the method further comprising a step of:

between steps (c) and (d), applying a retention force to the first toothbrush bristle restoration body and the second toothbrush bristle restoration body to retain the first toothbrush bristle restoration body and the second toothbrush bristle restoration body entrapping the bristles of the toothbrush between each of the first bristle restoration pad and the second bristle restoration pad in a closed configuration until removal of the toothbrush is desired.

15. The method of caring for a toothbrush as recited in claim 11, wherein the first toothbrush bristle restoration body and the second toothbrush bristle restoration body are at least one of:

a) are provided as a unitary member and flex between a separated and compressed state,
b) pivotally assembled to one another,
c) pivotally assembled to one another, including a biasing element to retain the first toothbrush bristle restoration body and the second toothbrush bristle restoration body in a contracted configuration,
d) assembled to one another by a third member, wherein the third member includes an expansion and contraction mechanism,
e) assembled to one another by a third member, wherein the third member includes an expansion and contraction mechanism, the expansion and contraction mechanism including a threaded element,
f) assembled to one another by a third member, wherein the third member includes an expansion and contraction mechanism, the expansion and contraction mechanism including a biasing element, and
g) pivotally assembled to one another by a third member.

16. The method of caring for a toothbrush as recited in claim 11, wherein at least a portion of the sides of the bristles are retained in position by a plurality of spatially arranged supporting surfaces of the bristle restoration pads, wherein the supporting surfaces are spatially arranged between an attachment end of the bristles and a free end of the bristles spatially exposing a majority of the sides of the bristles, further comprising a step of directing a sanitizer towards the sides of the bristles along an entire length of the exposed portion of the sides of the bristles to a sanitizer.

17. The method of caring for a toothbrush as recited in claim 11, the method further comprising a step of:

directing a sanitizer towards sides of the bristles, wherein the sanitizer includes at least one of:

a) an Ultraviolet (UV) light,
b) an Ultraviolet (UV) light emitting element,
c) an Ultraviolet (UV) Light Emitting Diode (LED),
d) a light pipe,
e) a light pipe located to extend between rows of bristles of the toothbrush,
f) a sanitizing strip,
g) a sanitizing strip comprising a carrier,
h) a sanitizing strip comprising a carrier, an adhesive and a sanitizing solution embedded in the carrier,
i) a sanitizing composition comprising an alcohol based solution,
j) a sanitizing composition comprising a chlorine based solution,
k) a sanitizing composition comprising a sodium hypochlorite based solution,
l) A sanitizing composition comprising a glutaraldehyde based solution,
m) a sanitizing composition comprising a hydrogen peroxide based solution,
n) a sanitizing composition comprising an iodophor based solution,
o) A sanitizing composition comprising an ortho-phthalaldehyde based solution,
p) a sanitizing composition comprising a peracetic acid based solution,
q) a sanitizing composition comprising a peroxyacetic acid based solution,
r) a sanitizing composition comprising a phenol based solution, and
s) a sanitizing composition comprising a quaternary ammonium compound based solution.

18. The method of caring for a toothbrush as recited in claim 11, wherein the separating the first toothbrush bristle restoration body and the second toothbrush bristle restoration body and the bringing each of the first toothbrush bristle restoration body and the second toothbrush bristle restoration body of the bristle restoration apparatus together are accomplished in accordance with at least one of:

a rotational motion, and
a linear motion.

19. The method of caring for a toothbrush as recited in claim 11, wherein at least one of the first toothbrush bristle restoration body and the second toothbrush bristle restoration body is at least partially fabricated of one of a translucent material and a transparent material, the toothbrush bristle restoration apparatus further comprising a light emitting circuit, the method further comprising a step of:

emitting light through the one of the translucent material and the transparent material of the at least one of the first toothbrush bristle restoration body and the second toothbrush bristle restoration body, wherein the emitted light is visible externally respective to the first toothbrush bristle restoration body and the second toothbrush bristle restoration body providing illumination external of the toothbrush bristle restoration apparatus.

20. The method of caring for a toothbrush as recited in claim 11, wherein a first bristle restoration pad bristle contacting surface and a second bristle restoration pad bristle contacting surface of the selected toothbrush bristle restoration pad assembly are shaped to accommodate one of the following toothbrush head shapes:

a) a toothbrush having a linear and parallel side portion of the series of bristles,
b) a toothbrush having a round side portion of the series of bristles,
c) a toothbrush having a linear and angled side portion of the series of bristles,
d) a toothbrush having a diamond shaped side portion of the series of bristles, and
e) a toothbrush having an irregular shaped side portion of the series of bristles.

* * * * *